United States Patent [19]

Ohtani et al.

[11] Patent Number: 5,534,654

[45] Date of Patent: Jul. 9, 1996

[54] AROMATIC-SULFONAMIDE-TYPE HYDROXAMIC ACID DERIVATIVE

[75] Inventors: Mitsuaki Ohtani, Nara; Hitoshi Arita, Kawanishi; Kenji Sugita, Kobe; Takaharu Matsuura, Kyoto; Kazuhiro Shirahase, Neyagawa, all of Japan

[73] Assignee: Shionogi & Co., Ltd., Osaka, Japan

[21] Appl. No.: 98,272

[22] PCT Filed: Dec. 7, 1992

[86] PCT No.: PCT/JP92/01593

§ 371 Date: Aug. 3, 1993

§ 102(e) Date: Aug. 3, 1993

[87] PCT Pub. No.: WO91/12075

PCT Pub. Date: Jun. 24, 1993

[30] Foreign Application Priority Data

Dec. 10, 1991 [JP] Japan ..................................... 3-350793

[51] Int. Cl.[6] ........................ A61K 31/18; C07C 259/04; C07C 311/30

[52] U.S. Cl. ................................ 564/90; 564/91; 564/94; 514/604

[58] Field of Search ................................ 548/495; 564/90, 564/91, 94; 514/604

[56] References Cited

FOREIGN PATENT DOCUMENTS 0453960  10/1991  European Pat. Off. .

*Primary Examiner*—David B. Springer
*Attorney, Agent, or Firm*—Wenderoth, Lind & Ponack

[57] ABSTRACT

A novel hydroxamic acid compound of the formula:

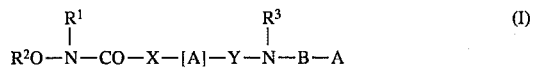

or a pharmaceutically acceptable salt thereof having cell growth inhibition, vascularization inhibition activities and the like.

The compounds of the present invention possess inhibitory activities against the growth of vascular endothelial cells and the expression of lymphocyte adhesive factors and the detransforming activity of cells transformed by ras gene, and inhibit the cell growth and are effective on inflammation and tumor.

3 Claims, No Drawings

AROMATIC-SULFONAMIDE-TYPE HYDROXAMIC ACID DERIVATIVE

TECHNICAL FIELD

The present invention relates to novel hydroxamic acid derivatives which show activities such as cell growth inhibitory activity, vascularization inhibitory activity and the like and are useful for prophylaxis and therapy of various inflammatory diseases, tumors, arteriosclerosis, peptic ulcer, diabetic retinopathy or the like.

BACKGROUND ART

In higher animals, a lot of tissues and organs have individual unique cell growth system, which are controlled by various regulatory mechanisms.

The participation of cell growth factors capable of effecting the positive control of cell growth of various cells has been shown and there have been reports which suggest the existence of relationships between various diseases and an abnormal growth of cells induced by an excessive production of cell growth factors and/or an excessive reaction to them. For example, tumor cells release a certain substance(s) capable of accelerating vascularization to maintain their own growth. It has been revealed that the vascularizing factor has a potent growth accelerating effect on vascular endothelial cells, and such vascularization can be also observed during chronic inflammation, arteriosclerosis and peptic ulcer. Although there are some compounds known to inhibit the vascularization, for example, DS4152 and the like (see, Japanese Patent Publication (KOKAI) No. 63-119500), the activity is not sufficient.

Furthermore, lymphocytes take an important role in case of inflammation, during which an adhesion phenomenon is observed between lymphocytes and vascular wall via adhesive molecules expressed on the vascular endothelial cells. Therefore, it has been considered that inflammation can be prevented by inhibiting the expression of adhesive molecules on the vascular endothelial cells or by directly interfering the adhesive reaction.

On the other hand, the discovery of tumor genes has promoted the development of antitumor agents. The tumor gene can be classified in several groups represented by src, ras, myc gene or the like. However, conventional antitumor agents inhibited the growth of normal cells as well because they had been developed as the result of a research which uses as an index the inhibitory effects against DNA synthesis, RNA synthesis, protein synthesis or the activity of factors participating in the cell growth. Therefore, the development of antitumor agents has been carried out on the basis of a different index directed to substances that inhibit the growth of tumor cells, not normal cells. It was found that when azatyrosine is administered to normal and transformed NIH 3T3 cells, the latter having been transformed by the introduction of ras gene activated by the mutation of No. 61 amino acid glutamine to leucine, the growth of the transformed cells is specifically inhibited. It was also observed that about 85% of transformed cells were converted into flat revertant cells morphologically similar to normal cells after the administration of azatyrosin. It was proposed that, in the revertant cells, the expression of gene participating in the conversion into normal cells is activated [Cancer and Chemotherapy, vol. 17 (3): part II, 500–501, 1990].

As is easily anticipated from the above, if a drug is discovered that does not react on normal cells but specifically does react on and detransform cells transformed by, for example, ras gene, and effects the detransformation, such a drug can provide an excellent antitumor agent. Accordingly, the development of such drugs has been desired.

DISCLOSURE OF THE INVENTION

The present invention provides novel hydroxamic acid derivatives which have three kinds of activities, namely (1) inhibitory activity against the growth of vascular endothelial cells, (2) inhibitory activity against the expression of lymphocyte adhesive factors, and (3) detransforming activity of cells transformed by ras gene, and inhibit the cell growth and are effective on inflammation and tumor.

The present inventors have made an intensive research in view of the circumstances above and have found that the compounds of the general formula as shown below possess inhibitory activities against the growth of endothelial cells, lymphocytes, tumor cells or the like, and vascularization inhibitory, anti-inflammatory and antitumor activities.

Thus, the present invention relates to a compound of the formula (I)

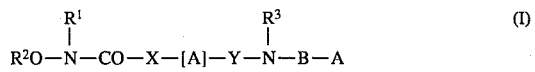

wherein [A] represents each optionally substituted aromatic ring or aromatic heterocyclic ring; A represents hydrogen or each optionally substituted aryl or aromatic heterocyclic ring group; B represents a single bond or a bivalent group of —B$_1$—B$_2$—, wherein B$_1$ represents —CO— or —SO$_2$— and B$_2$ represents alkylene, alkenylene, alkyleneoxy or alkenyleneoxy; X represents optionally substituted alkylene, said alkylene optionally containing a hetero atom(s) selected from O, S or N in the chain and further optionally containing an unsaturated bond(s); Y represents a single bond, a hetero atom or optionally substituted alkylene, said alkylene optionally containing a hetero atom(s) in the chain and optionally containing an unsaturated bond(s); and X and the nitrogen atom adjacent to Y may taken together form a 5 or more membered heterocyclic ring containing nitrogen atom(s) represented by the formula below:

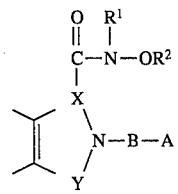

R$^1$, R$^2$ and R$^3$ each independently represents hydrogen or optionally substituted lower alkyl group or aryl group or pharmaceutically acceptable salts thereof.

BEST MODE FOR EFFECTING THE INVENTION

Throughout the present specification, the term aromatic ring means benzene, naphthalene, anthracene and phenanthrene, each of which may have one or more substituents selected from alkyl, hydroxy, alkoxy, aryloxy, acyloxy (alkanoyloxy, aroyloxy, etc.), carboxy, ester (alkoxycarbonyl, aralkoxycarbonyl, etc.), cyano, amino, mono- or di-substituted amino, hydrazino, hydroxyamino, alkoxyamino, halogen (fluorine, chlorine, bromine and iodine), nitro, formyl, acyl (alkanoyl, aroyl, etc.), (thio)carbamoyl, (thio)carbamoyloxy, (thio)ureide, sulfonamide, mono- or di-substituted sulfonamide, sulfonic acid, halogenoalkyl, hydroxyalkyl, alkoxyalkyl, acyloxyalkyl, nitroalkyl, (acyl)aminoalkyl, cyanoalkyl and carboxyalkyl. The alkoxy means a straight chained alkyloxy having 1–6 carbon atoms, for example, methoxy, ethoxy, propoxy, butoxy, pentyloxy, hexyloxy and the like.

The aromatic heterocyclic ring means a 5–6 membered ring containing one or more atoms selected from oxygen, sulfur and nitrogen atoms on the ring, said ring being optionally condensed with a carbon ring or other heterocyclic ring.

Examples include pyrrole, indole, carbazole, imidazole, pyrazole, benzimidazole, pyridine, quinoline, isoquinoline, acridine, phenanthridine, pyridazine, pyrimidine, pyrazine, cinnoline, phthaladine, quinazoline, naphthylidine, quinoxaline, 1, 3, 5-triazine, 1, 2, 4-triazine, 1, 2, 3-triazine, pteridine, isoxazole, benzisoxazole, oxazole, benzoxazole, 1, 2, 3-oxadiazole, 1, 2, 4-oxadiazole, 1, 2, 5-oxadiazole, 1, 3, 4-oxadiazole, benzoxadiazole, isothiazole, benzisothiazole, thiazole, benzthiazole, 1, 2, 3-thiadiazole, 1, 2, 4-thiadiazole, 1, 2, 5-thiadiazole, 1, 3, 4-thiadiazole, benzthiadiazole, furan, benzofuran, thiophene, benzothiophene, and the like. These heterocyclic rings may be substituted by one or more substituents selected from alkyl, hydroxy, alkoxy, carboxy, ester (alkoxycarbonyl, aralkoxycarbonyl, etc.), cyano, amino, mono- or di-substituted amino, hydrazino, hydroxyamino, alkoxyamino, halogen, nitro, formyl, acyl (alkanoyl, aroyl, etc.), (thio)carbamoyl, (thio)carbamoyloxy, (thio)ureide, sulfonamide, mono- or di-substituted sulfonamide, sulfonic acid, halogenoalkyl, hydroxyalkyl, alkoxyalkyl, acyloxyalkyl, nitroalkyl, (acyl)aminoalkyl, cyanoalkyl, carboxyalkyl and the like.

Examples of aryl group include phenyl, naphthyl, anthryl, phenanthryl and the like. These groups may have one or more substituents selected from alkyl, hydroxy, alkoxy, aryloxy, acyloxy (alkanoyloxy, aroyloxy, etc.), carboxy, ester (alkoxycarbonyl, aralkoxycarbonyl, etc.), cyano, amino, mono- or di-substituted amino, hydrazino, hydroxyamino, alkoxyamino, halogen, nitro, formyl, acyl (alkanoyl, aroyl, etc.), (thio)carbamoyl, (thio)carbamoyloxy, (thio)ureide, sulfonamide, mono- or di-substituted sulfonamide, sulfonic acid, halogenoalkyl, hydroxyalkyl, alkoxyalkyl, acyloxyalkyl, nitroalkyl, (acyl)aminoalkyl, cyanoalkyl, carboxyalkyl and the like.

The term aromatic heterocyclic ring group means a 5–6 membered cyclic group containing one or more atoms selected from oxygen, sulfur and nitrogen atoms on the ring, said ring being optionally condensed with a carbon ring or other heterocyclic ring.

Examples include pyrrolyl, indolyl, carbazolyl, imidazolyl, pyrazolyl, benzimidazolyl, pyridyl, quinolyl, isoquinolyl, pyridazinyl, pyrimidinyl, pyrazinyl, cinnolinyl, phthaladinyl, quinazolinyl, naphthylidinyl, quinoxalinyl, phenazinyl, 1, 3, 5-triazinyl, 1, 2, 4-triazinyl, 1, 2, 3-triazinyl, isoxazolyl, benzisoxazolyl, oxazolyl, benzoxazolyl, 1, 2, 3-oxadiazolyl, 1, 2, 4-oxadiazolyl, 1, 2, 5-oxadiazolyl, 1, 3, 4-oxadiazolyl, benzoxadiazolyl, isothiazolyl, benzisothiazolyl, thiazolyl, benzthiazolyl, 1, 2, 3-thiadiazolyl, 1, 2, 4-thiadiazolyl, 1, 2, 5-thiadiazolyl, 1, 3, 4-thiadiazolyl, benzthiadiazolyl, furyl, benzfuryl, thienyl, benzothienyl and the like. These cyclic groups may be substituted by one or more substituents selected from alkyl, hydroxy, alkoxy, carboxy, ester (alkoxycarbonyl, aralkoxycarbonyl, etc.), cyano, amino, mono- or di-substituted amino, hydrazino, hydroxyamino, alkoxyamino, halogen, nitro, formyl, acyl (alkanoyl, aroyl, etc.), (thio) carbamoyl, (thio) carbamoyloxy, (thio) ureide, sulfonamide, mono- or di-substituted sulfonamide, sulfonic acid, halogenoalkyl, hydroxyalkyl, alkoxyalkyl, acyloxyalkyl, nitroalkyl, (acyl) aminoalkyl, cyanoalkyl, carboxyalkyl and the like.

The alkylene in the "alkylene" or "alkyleneoxy" in the definition of $B_2$ means alkylene of 1–8 carbon atoms, preferably alkylene of 1–6 carbon atoms such as methylene, ethylene, propylene, butylene, pentylene, amylene, hexylene, heptylene, octylene and the like.

The alkenylene in the "alkenylene" or "alkenyleneoxy" in the definition of $B_2$ means alkenylene of 2–8 carbon atoms, preferably alkenylene of 2–6 alkenylene having one or more double bonds in the chain. Examples of the alkenylene available are vinylene, 1-propenylene, 2-propenylene, 1-butenylene, 2-butenylene, 3-butenylene, 1, 3-butadienylene, 1-pentenylene, 2-pentenylene, 3-pentenylene, 4-pentenylene, 1, 3-pentadienylene, 1, 4-pentadienylene, 2, 4-pentadienylene, 1-hexenylene, 2-hexenylene, 3-hexenylene, 4-hexenylene, 5-hexenylene, 1, 3-hexadienylene, 1, 4-hexadienylene, 1, 5-hexadienylene, 2, 4-hexadienylene, 2, 5-hexadienylene, 3, 4-hexadienylene, 3, 5-hexadienylene, 1, 3, 5-hexatrienylene, 1-heptenylene, 2-heptenylene, 3-heptenylene, 4-heptenylene, 5-heptenylene, 6-heptenylene, 1, 3-heptadienylene, 1, 4-heptadienylene, 1, 5-heptadienylene, 1, 6-heptadienylene, 2, 4-heptadienylene, 2, 5-heptadienylene, 2, 6-heptadienylene, 3, 5-heptadienylene, 3, 6-heptadienylene, 4, 6-heptadienylene, 1, 3, 5-heptatrienylene, 2, 4, 6-heptatrienylene, 1-octenylene, 2-octenylene, 3-octenylene, 4-octenylene, 5-octenylene, 6-octenylene, 7-octenylene, 1, 3-octadienylene, 1, 4-octadienylene, 1, 5-octadienylene, 1, 6-octadienylene, 1, 7-octadienylene, 2, 4-octadienylene, 2, 5-octadienylene, 2, 6-octadienylene, 2, 7-octadienylene, 3, 5-octadienylene, 3, 6-octadienylene, 3, 7-octadienylene, 4, 6-octadienylene, 4, 7-octadienylene, 5, 7-octadienylene, 1, 3, 5-octatrienylene, 1, 3, 6-octatrienylene, 1, 3, 7-octatrienylene, 1, 4, 6-octatrienylene, 1, 4, 7-octatrienylene, 1, 5, 7-octatrienylene, 2, 4, 6-octatrienylene, 2, 4, 7-octatrienylene, 2, 5, 7-octatrienylene, 1, 3, 5, 7-octatetraenylene and the like.

The lower alkyl means alkyl of 1–8 carbon atoms, preferably alkyl of 1–6 carbon atoms such as methyl, ethyl, propyl, butyl, pentyl, hexyl, heptyl, octyl and the like. Said alkyl may be substituted by one or more substituents selected from alkyl, hydroxy, alkoxy, carboxy, ester (alkoxycarbonyl, aralkoxycarbonyl, etc.), cyano, amino, mono- or di-substituted amino, hydrazino, hydroxyamino, alkoxyamino, halogen, nitro, formyl, acyl (alkanoyl, aroyl, etc.), (thio)carbamoyl, (thio)carbamoyloxy, (thio)ureide, sulfonamide, mono- or di-substituted sulfonamide, sulfonic acid, halogenoalkyl, hydroxyalkyl, alkoxyalkyl, acyloxyalkyl, nitroalkyl, (acyl)aminoalkyl, cyanoalkyl, carboxyalkyl and the like.

The optionally substituted alkylene represented by X means alkylene of 1–15 carbon atoms, preferably alkylene of 2–10 carbon atoms, more preferably alkylene of 2–8 carbon atoms such as methylene, ethylene, propylene, butylene, pentylene, amylene, hexylene, heptylene, octylene, nonylene, decylene, undecylene, dodecylene, tridecylene, tetradecylene, pentadecylene and the like.

Further, the alkylene represented by Y means alkylene of 1–6, preferably 1–4 carbon atoms.

Furthermore, the alkylene represented by X and Y may form alkenylene or alkynylene, containing one or more double bonds and/or one or more triple bonds in the chain. Examples of the alkenylene available are vinylene, 1-propenylene, 2-propenylene, 1-butenylene, 2-butenylene, 3-butenylene, 1, 3-butadienylene, 1-pentenylene, 2-pentenylene, 3-pentenylene, 4-pentenylene, 1, 3-pentadienylene, 1, 4-pentadienylene, 2, 4-pentadienylene, 1-hexenylene, 2-hexenylene, 3-hexenylene, 4-hexenylene, 5-hexenylene, 1, 3-hexadienylene, 1, 4-hexadienylene, 1, 5-hexadienylene, 2, 4-hexadienylene, 2, 5-hexadienylene, 3, 4-hexadienylene, 3, 5-hexadienylene, 1, 3, 5-hexatrienylene, 1-heptenylene, 2-heptenylene, 3-heptenylene, 4-heptenylene, 5-heptenylene, 6-heptenylene, 1, 3-heptadienylene, 1, 4-heptadienylene, 1, 5-heptadienylene, 1, 6-heptadienylene, 2, 4-heptadienylene, 2, 5-heptadienylene, 2, 6-heptadienylene, 3, 5-heptadienylene, 3, 6-heptadienylene, 4, 6-heptadienylene, 1, 3, 5-heptatrienylene, 2, 4, 6-heptatrienylene, 1-octenylene, 2-octenylene, 3-octenylene, 4-octenylene, 5-octenylene, 6-octenylene, 7-octenylene, 1, 3-octadienylene, 1, 4-octadienylene, 1, 5-octadienylene, 1, 6-octadienylene, 1, 7-octadienylene, 2, 4-octadienylene, 2, 5-octadienylene, 2, 6-octadienylene, 2, 7-octadienylene, 3, 5-octadienylene, 3, 6-octadienylene, 3, 7-octadienylene, 4, 6-octadienylene, 4, 7-octadienylene, 5, 7-octadienylene, 1, 3, 5-octatrienylene, 1, 3, 6-octatrienylene, 1, 3, 7-octatrienylene, 1, 4, 6-octatrienylene, 1, 4, 7-octatrienylene, 1, 5, 7-octatrienylene, 2, 4, 6-octatrienylene, 2, 4, 7-octatrienylene, 2, 5, 7-octatrienylene, 1, 3, 5, 7-octatetraenylene, 1-nonenylene, 2-nonenylene, 3-nonenylene, 4-nonenylene, 5-nonenylene, 6-nonenylene, 7-nonenylene, 8-nonenylene, 1, 3-nonadienylene, 1, 4-nonadienylene, 1, 5-nonadienylene, 1, 6-nonadienylene, 1, 7-nonadienylene, 1, 8-nonadienylene, 2, 4-nonadienylene, 2, 5-nonadienylene, 2, 6-nonadienylene, 2, 7-nonadienylene, 2, 8-nonadienylene, 3, 5-nonadienylene, 3, 6-nonadienylene, 3, 7-nonadienylene, 3, 8-nonadienylene, 4, 6-nonadienylene, 4, 7-nonadienylene, 4, 8-nonadienylene, 5, 7-nonadienylene, 5, 8-nonadienylene, 6, 8-nonadienylene, 1, 3, 5-nonatrienylene, 1, 3, 6-nonatrienylene, 1, 3, 7-nonatrienylene, 1, 3, 8-nonatrienylene, 1, 4, 6-nonatrienylene, 1, 4, 7-nonatrienylene, 1, 4, 8-nonatrienylene, 1, 5, 7-nonatrienylene, 1, 5, 8-nonatrienylene, 1, 6, 8-nonatrienylene, 2, 4, 6-nonatrienylene, 2, 4, 7-nonatrienylene, 2, 4, 8-nonatrienylene, 2, 5, 7-nonatrienylene, 2, 5, 8-nonatrienylene, 2, 6, 8-nonatrienylene, 3, 5, 7-nonatrienylene, 3, 5, 8-nonatrienylene, 3, 6, 8-nonatrienylene, 4, 6, 8-nonatrienylene, 1, 3, 5, 7-nonatetraenylene, 2, 4, 6, 8-nonatetraenylene and the like.

Moreover, examples of the alkynylene available are ethynylene, 1-propynylene, 2-propynylene, 1-butynylene, 2-butynylene, 3-butynylene, 1, 3-butadiynylene, 1-pentynylene, 2-pentynylene, 3-pentynylene, 4-pentynylene, 1, 3-pentadiynylene, 1, 4-pentadiynylene, 2, 4-pentadiynylene, 1-hexynylene, 2-hexynylene, 3-hexynylene, 4-hexynylene, 5-hexynylene, 1, 3-hexadiynylene, 1, 4-hexadiynylene, 1, 5-hexadiynylene, 2, 4-hexadiynylene, 2, 5-hexadiynylene, 3, 5-hexadiynylene, 1-heptynylene, 2-heptynylene, 3-heptynylene, 4-heptynylene, 5-heptynylene, 6-heptynylene, 1, 3-heptadiynylene, 1, 4-heptadiynylene, 1, 5-heptadiynylene, 1, 6-heptadiynylene, 2, 4-heptadiynylene, 2, 5-heptadiynylene, 2, 6-heptadiynylene, 3, 5-heptadiynylene, 3, 6-heptadiynylene, 4, 6-heptadiynylene, 1-octynylene, 2-octynylene, 3-octynylene, 4-octynylene, 5-octynylene, 6-octynylene, 7-octynylene, 1, 3-octadiynylene, 1, 4-octadiynylene, 1, 5-octadiynylene, 1, 6-octadiynylene, 1, 7-octadiynylene, 2, 4-octadiynylene, 2, 5-octadiynylene, 2, 6-octadiynylene, 2, 7-octadiynylene, 3, 5-octadiynylene, 3, 6-octadiynylene, 3, 7-octadiynylene, 4, 6-octadiynylene, 4, 7-octadiynylene, 5, 7-octadiynylene, 1, 3, 5-octatriynylene, 1, 3, 6-octatriynylene, 1, 3, 7-octatriynylene, 1, 4, 6-octatriynylene, 1, 4, 7-octatriynylene, 1, 5, 7-octatriynylene, 2, 4, 6-octatriynylene, 2, 4, 7-octatriynylene 2, 5, 7-octatriynylene, 1, 3, 5, 7-octatetraynylene, 1-nonenylene, 2-nonenylene, 3-nonenylene, 4-nonenylene, 5-nonenylene, 6-nonenylene, 7-nonylene, 8-nonylene, 1, 3-nonadiynylene, 1, 4-nonadiynylene, 1, 5-nonadiynylene, 1, 6-nonadiynylene, 1, 7-nonadiynylene, 1, 8-nonadiynylene, 2, 4-nonadiynylene, 2, 5-nonadiynylene, 2, 6-nonadiynylene, 2, 7-nonadiynylene, 2, 8-nonadiynylene, 3, 5-nonadiynylene, 3, 6-nonadiynylene, 3, 7-nonadiynylene, 3, 8-nonadiynylene, 4, 6-nonadiynylene, 4, 7-nonadiynylene, 4, 8-nonadiynylene, 5, 7-nonadiynylene, 5, 8-nonadiynylene, 6, 8-nonadiynylene, 1, 3, 5-nonatriynylene, 1, 3, 6-nonatriynylene, 1, 3, 7-nonatriynylene, 1, 3, 8-nonatriynylene, 1, 4, 6-nonatriynylene, 1, 4, 7-nonatriynylene, 1, 4, 8-nonatriynylene, 1, 5, 7-nonatriynylene, 1, 5, 8-nonatriynylene, 1, 6, 8-nonatriynylene, 2, 4, 6-nonatriynylene, 2, 4, 7-nonatriynylene, 2, 4, 8-nonatriynylene, 2, 5, 7-nonatriynylene, 2, 5, 8-nonatriynylene, 2, 6, 8-nonatriynylene, 3, 5, 7-nonatriynylene, 3, 5, 8-nonatriynylene, 3, 6, 8-nonatriynylene, 4, 6, 8-nonatriynylene, 1, 3, 5, 7-nonatetraynylene, 2, 4, 6, 8-nonatetraynylene, and the like.

Further, any hetero atom(s) may exist at an optional position(s) of said alkylene chain. In such cases, —CH$_2$— may be changed to —O—, —S— or —NR—; and —CH= and =CH— may be changed to —N= and =N—.

Furthermore, said alkylene may be substituted by one or more of substituents which are identically or differently selected from the group consisting of alkyl, alkenyl, alkynyl, halogen, hydroxy, alkoxy, aryloxy, acyloxy (alkanoyloxy, aroyloxy, etc.), carboxy, ester (alkoxycarbonyl, aralkoxycarbonyl, etc.), cyano, amino, mono- or di-substituted amino, hydroxyamino, alkoxyamino, halogen, nitro, formyl, acyl (alkanoyl, aroyl, etc.), (thio)carbamoyl, (thio) carbamoyloxy, (thio)ureide, sulfonamide, mono- or di-substituted sulfonamide, sulfonic acid and the like. In this case, examples of alkenyl or alkynyl are similar to those illustrated in the definition of alkenylene and alkynylene above.

Examples of the heterocyclic ring of 5 or more members formed by X and Y together with the adjacent nitrogen atom are pyrrole, pyrroline, imidazole, pyrazole, 2, 3-dihydroimidazole, 2, 3-dihydropyrazole, 2, 3-dihydrooxazole, 1, 5-dihydroisoxazole, 2, 3-dihydroisoxazole, 2, 3-dihydrothiazole, 1, 2-dihydropyridazine, 3, 4-dihydropyrimidine, 1, 2-dihydropyrimidine, 3, 4-dihydropyrazine, 1, 2-dihydropyrazine, 1, 2-dihydropyridine and the like. In this case, the group X may be substituted at an optional position by the group:

—CO—N(R$^1$)—OR$^2$.

The present invention includes all the salts that can be formed with a compound of the formula (I). In general, the compound (I) can form a salt with an organic or inorganic acid or an organic or inorganic base. For example, the inorganic base includes alkali metal (sodium, potassium, etc.), alkali earth metal (calcium, magnesium, etc.) and the like, and the organic base includes trimethylamine, triethylamine, pyridine, picoline, N, N-dibenzylethylenediamine, ethanolamine, diethanolamine, tris-hydroxymethyl aminomethane, dicyclohexylamine and the like. The inorganic acid includes illustratively hydrochloric acid, hydrobromic acid, sulfuric acid, nitric acid, phosphoric acid and the like. Examples of the organic acids include formic acid, acetic acid, trifluoroacetic acid, oxalic acid, tartaric acid, fumaric acid, maleic acid, methanesulfonic acid, benzenesulfonic acid, p-toluenesulfonic acid and the like. The basic or acidic amino acid includes illustratively arginine, lysine, ornithine, aspartic acid, glutamic acid and the like. In particular, the salts with inorganic acids or those with inorganic bases are preferred.

The above-mentioned examples are by no means restrictive and the compounds of the present invention may form pharmacologically acceptable esters and other derivatives. As far as the formed salts, esters and derivatives are substantially non-toxic to warm-blooded animal and convertible into the compound of the present invention in living bodies, they all fall within the scope of the present invention.

The present invention relates to the compound of the formula (Ia)

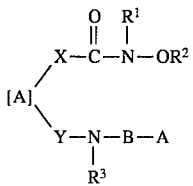
(Ia)

wherein [A], A, B, $R^1$, $R^2$, $R^3$, X and Y each has the same significance as defined above; or a 5 or more membered heterocyclic ring containing nitrogen atom(s) of the formula (Ib)

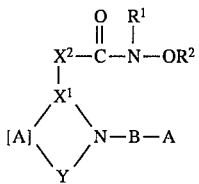
(Ib)

wherein $X^1-X^2$ has the same significance as X, $X^1$ represents the ring forming moiety, $X^2$ represents the moiety outside the ring, and [A], A, B, $R^1$, $R^2$ and Y each has the same significance as defined above, which is formed when X and Y are combined together with the nitrogen atom.

In the case of the compound of the formula (Ib), the group X can be substituted at an optional position by the group:

—CO—N ($R^1$)—$OR^2$.

The process for preparing the compounds of the present invention will be hereinafter explained.

The compounds (I) of the present invention can be prepared by reacting the compound (IIa) or the compound (IIb) of the following formulae

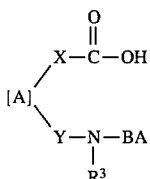
(IIa)

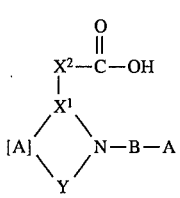
(IIb)

wherein [A], A, B, $R^3$, X, $X^1-X^2$ and Y each has the same significance as defined above with a carboxylic acid activator to give a reactive derivative and allowing the latter to react with a hydroxylamine.

The carboxylic acid activators usable in the reaction with the compound (II) illustratively include thionyl chloride, phosphorus oxychloride, phosphorus pentachloride, alkyl chloroformates (e.g. methyl chloroformate, ethyl chloroformate, etc.), oxalyl chloride, carbodiimides (e.g. N, N-dicyclohexylcarbodiimide (DCC), etc.), hydroxyimides (e.g. N-hydroxybenzotriazole, N-hydroxysuccinimide) and the like. This reaction is generally carried out in the presence of halogenohydrocarbons (e.g. methylene chloride, chloroform, etc.), ethers (e.g. tetrahydrofuran, dioxane, dimethyl ether, diethyl ether, isopropyl ether), N, N-dimethylformamide or a mixture thereof. The reaction is effected at temperature of 0°–50° C., preferably around room temperature over a period of 0.5–10 hours, preferably 1–3 hours.

The acid anhydride, acid halide or active ester obtained by the reaction with the carboxylic acid activator is allowed to react with a hydroxylamine. This reaction is carried out under anhydrous or hydrous conditions in the presence of a deoxidizer such as pyridine, triethylamine, potassium carbonate, sodium carbonate, potassium hydrogencarbonate, sodium hydrogencarbonate or the like in a solvent such as methylene chloride, tetrahydrofuran, dioxane, N, N-dimethylformamide, acetone or the like. The present reaction is effected at temperature of 0°–50° C., preferably around room temperature over a period of 0.1–10 hours, preferably 0.5–2 hours.

The hydroxylamine includes hydroxylamine, N-methylhydroxyamine, O-methylhydroxyamine, and their hydrochloride and sulfate.

The resulting compounds (I) can be isolated by conventional purifying means such as recrystallization, chromatography or the like.

The starting compound (II) can be prepared according to the following processes.

(a) Process A (Synthesis of IIa)

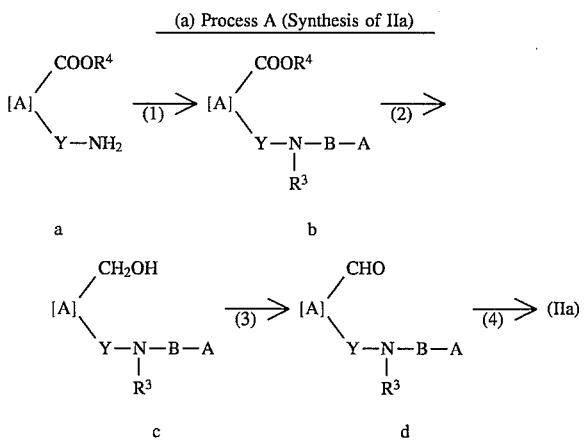

wherein [A], A, B, $R^3$ and Y each has the same significance as defined above, and $R^4$ means hydrogen, optionally substituted lower alkyl or aryl group.

(1) In this reaction, a compound a is allowed to react with an acid halide (substituted sulfonic acid halide or substituted carboxylic acid halide) in the presence of a base in a solvent (e.g. tetrahydrofuran, etc.) for sulfonylation or carbonylation to give a compound b. This reaction is effected at temperature of 0°–50° C., preferably around room temperature over a period of 0.1–20 hours, preferably about 1–5 hours.

The base usable illustratively includes sodium hydrogencarbonate, potassium hydroxide, sodium carbonate, sodium acetate, triethylamine, pyridine and the like.

The sulfonic acid halide includes benzenesulfonylene chloride and benzenesulfonylene bromide, and the substituted sulfonic acid halide includes methoxybenzenesulfonylene chloride, halogenobenzenesulfonylene chloride, hydroxybenzenesulfonylene chloride, aminobenzenesulfonylene chloride and sulfonic acid derivatives thereof having a desirous substituent such as naphthyl derivative or the like. The carboxylic acid halide includes benzoyl chloride, benzyloxycarbonyl chloride, oxalyl chloride and carboxylic acid derivatives thereof having a desirous substituent.

(2) In this reaction, a compound b is reduced in the presence of a reducing agent in an organic solvent to give a compound c.

The reaction is effected at temperature of 0°–50° C., preferably around room temperature over a period of 10 hours, preferably 1–3 hours.

The solvent usable includes tetrahydrofuran, diethyl ether, methanol, ethanol and the like.

The reducing agent usable is any one of those ordinarily used in the reducing reaction, including lithium aluminum hydride, sodium bis (2-methoxyethoxy) aluminum hydride, diisobutylaluminum hydride, sodium borohydride, lithium borohydride and the like.

(3) In this reaction, a compound c is subjected to an oxidation in the presence of an oxidizing agent, for example, in an appropriate organic solvent to give a compound d.

The reaction is effected at temperature of 0°–50° C., preferably around room temperature over a period of 0.5–5 hours, preferably 1–3 hours.

The organic solvent usable includes methylene chloride, acetone and the like, and the methylene chloride is preferred in particular.

The oxidizing agent includes oxalyl chloridedimethyl sulfoxide, sulfur trioxide-pyridine complex, chromic acid-pyridine complex and dimethyl sulfoxide, and the pyridinium chlorochromate is preferred in particular.

(4) This reaction is well known as Wittig reaction. Thus, a compound d is allowed to react with a phosphonium salt of the formula:

$(Ph)_3P^+R^7 COOR^8 Hal$ wherein Hal means halogen, $R^7$ means an optionally substituted alkylene similar to X as defined above except that the alkylene of $R^7$ has one carbon fewer than that of X, said alkylene may contain a hetero atom(s) such as O, S or N or an unsaturated bond(s) in the chain, and $R^8$ means hydrogen or a lower alkyl in the presence of a strong base in an inert solvent at temperature of 0°–50° C., preferably around room temperature for activation. When $R^8$ is other than hydrogen, the objective compound (IIa) is obtained by conventional hydrolysis.

The inert solvent usable illustratively includes toluene, tetrahydrofuran, dimethyl sulfoxide, t-butanol and the like.

Examples of the strong base are potassium tert-butoxide, lithium diisopropylamide, sodium hydride, n-butyllithium and the like, and the potassium tert-butoxide is preferred.

(b) Process B (Synthesis of IIa having alkynylene)

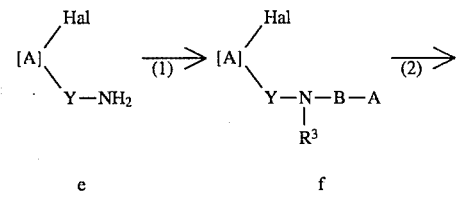

e           f

-continued
(b) Process B (Synthesis of IIa having alkynylene)

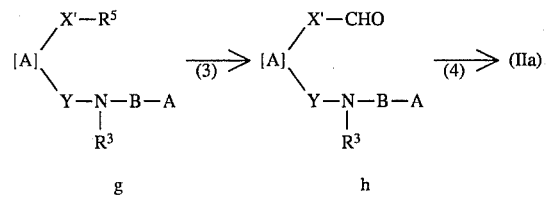

g           h wherein [A], A, B, $R^3$ and Y each has the same significance as defined above, Hal means halogen, X' means ethynylene-$X^3$ ($X^3$ is a single bond or an optionally substituted alkylene, said alkylene may contain a hetero atom(s) such as O, S or N, or an unsaturated bond(s) in the chain and forms a part of X by binding to the ethynylene directly bound to [A]), and $R^5$ means —$COOR^4$ ($R^4$ has the same significance as defined above), —$CH_2OR^6$ ($R^6$ is an alcohol protecting group) or a functional group convertible into an aldehyde such as —CN or the like.

(1) The compound e is subjected to sulfonylation or carbonylation in the same manner as above to give a compound f.

(2) The compound g is prepared by refluxing a mixture of a compound f, palladium bis-triphenylphosphine dichloride, copper iodide and a terminal acetylenic compound in the presence of a base in an organic solvent for 8 to 48 hours, preferably 10 to 30 hours with heating.

The organic solvent usable includes benzene, toluene, ether, tetrahydrofuran, pyridine, triethylamine and the like.

The base usable includes triethylamine, N-methylmorpholine, dicyclohexylamine, pyridine, trimethylamine, diethylamine, n-butylamine, diisopropylamine and the like.

(3) The compound h is prepared by reducing the group $R^5$ in the form of ester, nitrile or the like of a compound g with lithium aluminum hydride or a related reducing agent thereof, or oxidizing the primary alcohol generated by removing the group $R^6$ in the form of an alcohol protecting group under the same conditions as in process A (3) above.

(4) The compound h is subjected to the Wittig reaction under the same conditions as in Process A (4) above to give a compound (IIa).

(c) Process C (Synthesis of IIb)

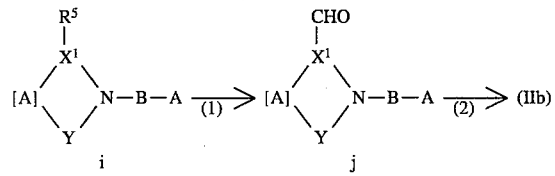

i           j wherein [A], A, B, $X^1$, Y and $R^5$ each has the same significance as defined above.

(1) When, as a starting material, a cyclic compound i is used, it is allowed to react in the same manner as in the Process B (3) above to give a compound j.

(2) The compound j is subjected to the Wittig reaction under the same conditions as in the Process A (4) above to give a compound (IIb).

When a commercially available compound j is used, the step (1) can be abridged.

The compounds of the present invention, namely the hydroxamic acid derivatives include optically active compound because of the presence of an asymmetric center. Accordingly, the compounds (I) of the present invention means inclusively the both of the optically active compounds and racemic compounds.

The compounds of the present invention can be orally or parenterally administered. In case of oral administration, a compound of the present invention may be formulated into ordinary formulations in the form of solid such as tablets, powders, granules, capsules and the like; solutions; oily suspensions; liquid formulations such as syrups, elixirs and the like. In case of parenteral administration, a compound of the present invention may be formulated into aqueous or oily suspension for injection. In preparing the formulations, conventional excipients, binders, lubricants, aqueous solvents, oily solvents, emulsifiers, suspending agents or the like may be used, and other additives, such as preservatives, stabilizers or the like may also be included.

Although appropriate daily dosage of the compound of the present invention varies depending upon the administration route, age, body weight and conditions of the patient, and the kind of disease to be treated, it can generally be between 0.05–1000 mg, preferably 10–500 mg on oral administration, and 0.01–300 mg, preferably 0.05–100 mg on parenteral administration, in 1–5 divisions.

The following Examples are provided to further illustrate the present invention and are not to be construed as limiting thereof.

The abbreviations used in the examples have the following meanings: Me=methyl; Et=ethyl; Ph=phenyl; THF=tetrahydrofuran; and DMF=N, N-Dimethylformamide.

EXAMPLE 1

(6E)-7-(2-Phenylsulfonylaminophenyl) heptenohydroxamic Acid (I-1) and (6Z)-7-(2-phenylsulfonylaminophenyl) heptenohydroxamic Acid (I-2)

layer is washed with water, dried, filtered and concentrated to yield a mixture of compounds (IIa-1) and (IIa-2). When the mixture is separated and purified by column chromatography, 0.860 g (2.39 mmol, yield 40%) of compound (IIa-1) and 0.675 g (1.88 mmol, yield 31%) of compound (IIa-2) are obtained as a pure product.

Compound (IIa-1): m.p.=116°–119° C. $^1$HNMR (CDCl$_3$) δ: 1.30–1.55 (m, 2H); 1.55–1.78 (m, 2H); 2.10 (dt, J=6.7, 6.7 Hz, 2H); 2.39 (t, J=7.0 Hz, 2H); 5.90 (dt, J=15.7, 6.5 Hz, 1H); 6.12 (d, J=15.7 Hz, 1H); 6.82 (s, 1H); 7.06–7.62 (m, 7H); 7.66–7.84 (m, 2H). IR (Nujol): 3400–2200, 3270, 1702, 1650. Elementary analysis (%) for $C_{19}H_{21}NO_4S$. Calc.: C,63.48; H,5.90; N,3.90; S,8.92. Found: C,63.20; H,5.92; N,3.84; S,8.99.

Compound (IIa-2): m.p.=82° C. $^1$HNMR (CDCl$_3$) δ: 1.15–1.65 (m, 4H); 1.92 (dt, J=7.4, 7.4 Hz, 2H); 2.28 (t,J=7.2 Hz, 2H); 5.77 (dt, J=11.3, 6.9 Hz, 1H); 5.90 (d, J=11.3 Hz, 1H); 6.62 (s, 1H); 6.93–7.30 (m, 3H); 7.35–7.62 (m, 4H); 7.68–7.82 (m, 2H). IR (Nujol): 3520–2400, 3310, 3140, 1712. Elementary analysis (%) for $C_{19}H_{21}NO_4S$. Calc.: C,63.48; H,5.90; N,3.90; S,8.92. Found: C,63.38; H,5.91; N,3.85; S,8.62.

(2) To a 4 ml solution of 359 mg (1.0 mmol) of compound (IIa-1) in DMF are added 230 mg (2.0 mmol) of N-hydroxysuccinimide and 412 mg (2.0 mmol) of N,N-dicyclohexylcarbodiimide. After stirring for 4 hr at room temperature, 208 mg (3 mmol) of hydroxylamine hydrochloride and 418 μl (3 mmol) of triethylamine are added and the mixture is further stirred overnight. The reaction mixture is partitioned between ethyl acetate and hydrochloric acid. The organic layer is washed with water (×2) and a saturated saline (×1), dried, filtered and concentrated. Purification by column

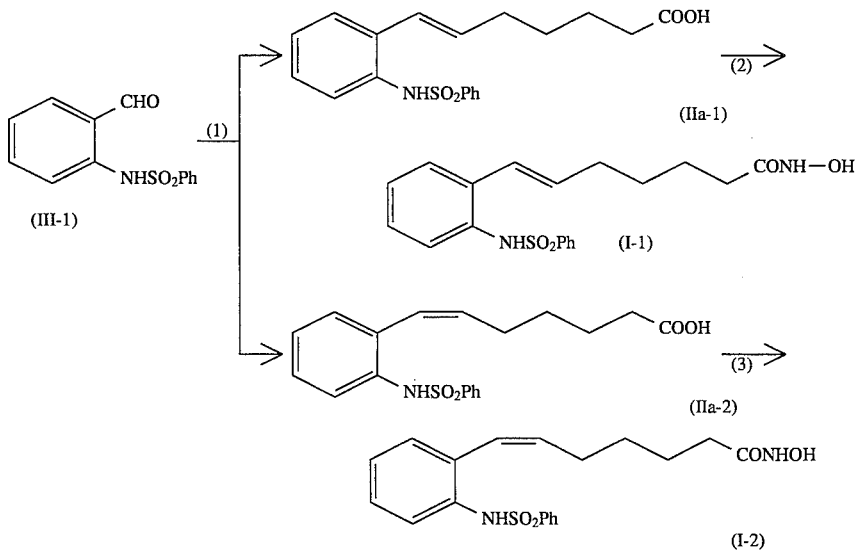

(1) To a suspension of 9.60 g (21.0 mmol) of 5-carboxypentyltriphenylenephosphonium bromide in 80 ml of THF is added 4.58 g (40.8 mmol) of potassium tert-butylate at 0° C. After stirring at room temperature for 1 hr, the mixture is cooled again to 0° C. To the mixture is added a solution of 1.57 g (6.0 mmol) of compound (III-1) in 20 ml of THF. After stirring for 1.5 hr at 0° C., the reaction solution is partitioned between toluene and water and the aqueous layer is washed with toluene. The aqueous layer is partitioned between methylene dichloride and 2N HCl and the organic chromatography on silica gel provides 160 mg (0.427 mmol; yield, 43%) of the objective compound (I-1).

$^1$HNMR (DMSO) δ: 1.14–1.40 (m, 2H); 1.40–1.60 (m, 2H); 1.85–2.10 (m, 4H); 6.02 (dt, J=15.8, 6.6 Hz, 1H); 6.39(d, J=15.8 Hz, 1H); 6.90–7.03 (m, 1H); 7.03–7.22 (m, 2H); 7.37–7.70 (m, 6H); 8.68 (s, 1H); 9.69 (brs, 1H); 10.37 (s, 1H). IR (Nujol): 3700-2080, 1640. Elementary analysis (%) for $C_{19}H_{22}N_2O_4S$•0.4$H_2O$. Calc.: C,59.78; H,6.03; N,7.34; S,8.40. Found: C,59.83; H,5.87; N,7.33; S,7.99.

(3) Compound (IIa-2) is reacted in a similar manner as the process (2) above to yield the objective compound (I-2) (yield: 42.6%).

$^1$HNMR (DMSO) δ: 1.12–1.56 (m, 4H); 1.80–2.05 (m, 4H); 5.49 (dt, J=11.6, 7.1 Hz, 1H); 6.31(d, J=11.6 Hz, 1H); 7.00–7.27 (m, 4H); 7.43–7.74 (m, 5H); 8.67 (m, 1H);9.59 (m, 1H); 10.33 (m, 1H). IR (Nujol): 3480–2440, 3270, 3195, 1630, 1575, 1535. Elementary analysis (%) for $C_{19}H_{22}N_2O_4S$. Calc.: C,60.93; H,5.93; N,7.48; S,8.56. Found: C,60.75; H,5.90; N,7.46; S,8.45.

EXAMPLE 2

(5E)-6-(2-Phenylsulfonylaminophenyl) hexenohydroxamic Acid (I-3)

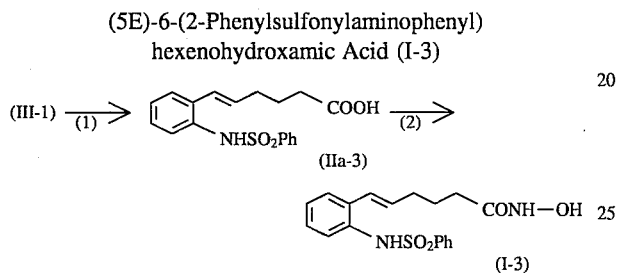

(1) To a suspension of 13.3 g (30 mmol) of 4-carboxybutyltriphenylenephsophonium bromide in 100 ml of THF is added 6.6 g (58.8 mmol) of potassium tert-butoxide at 0° C. in an atmosphere of nitrogen. After stirring for 40 min at room temperature, the mixture is cooled to −20° C. To the mixture is added gradually 10 ml of a solution of 2.24 g (8.57 mmol) of compound (III-1) in THF over a period of more than 15 min. After the mixture is stirred for 30 min at −15° C., it is warmed up to 0° C. over 2 hr while stirring. The reaction mixture is partitioned between toluene and water and the organic layer is washed with water. Aqueous layers are combined and washed with toluene. The aqueous layer is partitioned between methylene chloride and 2N HCl. The organic layer is washed with water, dried and concentrated. Purification by column chromatography on silica gel and recrystallization provides 2.13 g (6.17 mmol; yield, 72.0%) of the objective compound (IIa-3).

M.p.=130°–132° C. $^1$HNMR (CDCl$_3$) δ: 1.76 (quint, J=7.1 Hz, 2H); 2.18 (dt, J=6.8, 7.1 Hz, 2H); 2.39 (t, J=7.1 Hz, 2H); 5.89 (dt, J=15.5,6.8 Hz, 1H); 6.15 (d, J=15.5 Hz, 1H); 6.83 (s, 1H); 7.02–7.65 (m, 7H); 7.65–7.85 (m, 2H). IR (Nujol): 3400–2200, 3300, 1708, 1578. Elementary analysis (%) for $C_{18}H_{19}NO_4S$. Calc.: C,62.58; H,5.56; N,4.06; S,9.28. Found: C,62.35; H,5.52; N,4.11; S,9.34.

(2) Compound (IIa-3) is reacted in a manner analogous to that set forth in Example 1 (2) to give the objective compound (I-3) (yield, 67%).

$^1$HNMR (DMSO) δ: 1.42–1.70 (m, 2H); 1.82–2.13 (m, 4H); 6.02 (dt, J=15.8, 6.6 Hz, 1H); 6.40(d, J=15.8 Hz, 1H); 6.88–7.04 (m, 1H); 7.04–7.23 (m, 2H); 7.36–7.72 (m, 6H); 8.72 (brs, 1H); 9.79 (brs, 1H); 10.37 (brs, 1H). IR (CHCl$_3$): 3480–2600, 3350, 1665.

Mass analysis: LSIMS m/z=361 [M+H]+, 721[2M+H]+. HRLSIMS: for $C_{18}H_{21}N_2O_4S$. Calc.: 361.1221. Found: 361.1226.

EXAMPLE 3

(2E)(4E)-5-(2-Phenylsulfonylaminophenyl) pentadienohydroxamic Acid (I-4), (2E)(4E)-N-methyl-5-(2-phenylsulfonylaminophenyl) pentadienohydroxamic Acid (I-5) and (2E) (4E)-O-methyl-5-(2-phenylsulfonylaminophenyl) pentadienohydroxamic Acid (I-6)

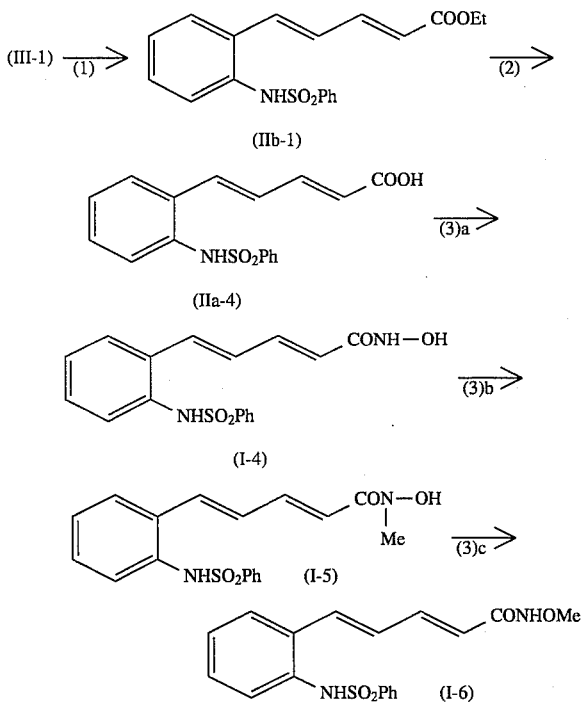

(1) To a suspension of 14.15 g (31.1 mmol) of 4-ethoxycarbonylene-2-propenylenephsophonium bromide in 200 ml of THF is added 3.38 g (30.1 mmol) of potassium tert-butoxide at 0° C. in an atmosphere of nitrogen. After stirring for 1 hr at room temperature, the mixture is cooled again to 0° C. To the mixture is added gradually 50 ml of a solution of 2.62 g (10.0 mmol) of compound (III-1) in THF over a period of more than 10 min. After the mixture is stirred for about 1 hr at room temperature, the reaction mixture is partitioned between ethyl acetate and 2N HCl. The organic layer is washed with water and a saturated saline, dried over sodium sulfate, filtered and concentrated under reduced pressure. Purification by column chromatography on silica gel and recrystallization from ether/hexane provides 2.65 g (7.41 mmol; yield, 74%) of the objective compound (IIb-1).

M.p.=120.5°–121.5° C. $^1$HNMR (CDCl$_3$) δ: 1.33 (t, J=7.0 Hz, 3H); 4.24 (q, J=7.0 Hz, 2H); 5.93 (d, J=15.2 Hz, 1H); 6.57 (brs, 1H); 6.62 (dd, J=15.2 Hz, 10.2 Hz, 1H); 6.77 (d, J=15.2 Hz, 1H); 7.13–7.35 (m, 4H); 7.35–7.63 (m, 4H); 7.63–7.80 (m, 2H). IR (KBr): 3245, 2990, 1700, 1622, 1600, 1569, 1338, 1242, 1175, 1162, 1138, 1090, 1005, 589, 555. Elementary analysis (%) for $C_{19}H_{19}NO_4S$. Calc.: C,63.85; H,5.36; N, 3.92; S,8.97. Found: C,63.79; H,5.33; N, 3.90; S,8.88.

(2) To a 30 ml solution of 2.60 g (7.27 mmol) of compound (IIb-1) in methanol is added 21.8 ml (21.8 mmol) of 1N sodium hydroxide solution and the mixture is stirred for about 3.5 hr. The reaction mixture is partitioned between ethyl acetate and water. The aqueous layer is partitioned between ethyl acetate and hydrochloric acid and the organic layer is washed with water and a saturated saline, dried over magnesium sulfate, filtered and concentrated. Recrystallization from an ethyl acetate/ether/hexane solvent system provides 2.07 g (6.29 mmol; yield, 87%) of the objective compound (IIa-4).

M.p.=241.5°–243.5° C. $^1$HNMR (DMSO) δ: 5.95 (d, J=14.6 Hz, 1H); 6.77–7.17 (m, 4H); 7.17–7.35 (m, 2H); 7.41–7.75 (m, 6H); 9.88 (brs, 1H); 12.30 (brs,1H). IR (KBr): 3680–2000, 3260, 1676, 1620, 1600, 1330, 1314, 1280, 1168, 1155, 997, 752, 719, 591. Elementary analysis (%) for $C_{17}H_{15}NO_4S$. Calc.: C,61.99; H,4.59; N,4.25; S,9.73. Found: C,61.74; H,4.69; N,3.95; S,9.44.

(3) (a) To an 8 ml suspension of 645 mg (1.96 mmol) of compound (IIa-4) in methylene chloride is added 0.60 ml (6.88 mmol) of oxalyl chloride and one drop of DMF. The mixture is stirred for 30 min at room temperature and then for 1 hr at 40° C. and concentrated under reduced pressure to obtain acid chloride. In an another vessel, a suspension of 695 mg (10.0 mmol) of hydroxylamine in 12 ml of THF is prepared, which is combined with 8.0 ml of saturated $NaHCO_3$ solution and stirred for 5 min at room temperature. To the solution is added the previously prepared 8.0 ml of a solution of acid chloride in THF and stirred vigorously for 30 min at room temperature. The reaction mixture is partitioned between ethyl acetate and 2N HCl. The organic layer is washed with water and a saturated saline, concentrated under reduced pressure and allowed to crystallize to obtain 400 mg (1.16 mmol; yield, 59%) of the objective compound (I-4).

$^1$HNMR (DMSO) δ: 5.94 (d, J=14,4 Hz, 1H); 6.73–7.08 (m, 4H); 7.14–7.30 (m, 2H); 7.43–7.74 (m, 6H); 8.99 (brs, 1H); 9.87 (brs, 1H); 10.74 (brs, 1H). IR (Nujol): 3420–2760, 3300, 3140, 1640, 1595, 1550. Elementary analysis (%) for $C_{17}H_{16}N_2O_4S·0.2H_2O$. Calc.: C,58.66; H,4.76; N,8.05; S,9.21. Found: C,58.61; H,4.78; N,7.94; S,9.28.

(3)(b) Compound (IIa-4) is reacted with N-methylhydroxylamine hydrochloride and treated in a manner similar to that set forth in the process (a) above to yield the objective compound (I-5) (yield: 89%).

M.p.=192.5°–193.5° C. (decomp.). $^1$HNMR (DMSO) δ: 3.19 (s, 3H); 6.63–7.12 (m, 4H); 6.71 (d, J=14.4 Hz, 1H); 7.12–7.30 (m, 2H); 7.40–7.75 (m, 6H); 9.87 (s, 1H); 10.01 (s, 1H). IR (KBr): 3340, 3060, 2810, 1639, 1594, 1321, 1160, 999, 591, 554. Elementary analysis (%) for $C_{18}H_{18}N_2O_4S$. Calc.: C,60.32; H,5.06; N, 7.82; S,8.95. Found: C,60.17; H,5.10; N, 7.55; S,8.72.

(3)(c) Compound (IIa-4) is reacted with O-methylhydroxylamine hydrochloride and treated in a manner similar to that described in the process (a) above to yield the objective compound (I-6) (yield: 54%).

M.p.=174°–175.5° C. $^1$HNMR (DMSO) δ: 3.65 (s, 3H); 5.77–6.04 (m, 1H); 6.75–6.94 (m, 2H); 6.94–7.15 (m, 2H);7.15–7.30 (m, 2H); 7.40–7.77 (m, 6H); 9.87 (s, 1H); 11.24 (s, 1H). IR (KBr): 3680–2320, 3330, 1662, 1620, 1502, 1485, 1448, 1330, 1160, 1092, 1060, 998, 755, 688, 588, 552. Elementary analysis (%) for $C_{18}H_{18}N_2O_4S$. Calc.: C,60.32; H,5.06; N,7.82; S,8.95. Found: C,60.17; H,5.14; N,7.87; S,8.98.

EXAMPLE 4

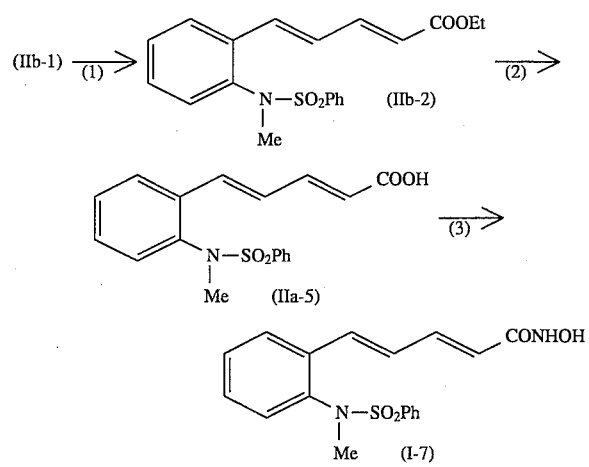

(2E)(4E)-5-[2-(N-Methylphenylsulfonylamino)phenyl]-2,4-pentadienohydroxamic Acid (I-7)

(1) To a solution of 1.4 g (3.92 mmol) of compound (IIb-1) in 10 ml ethyl acetate is added an ether solution of diazomethane prepared separately. When the yellowish color is no more disappeared, the mixture is concentrated under reduced pressure at temperature below room temperature. Purification of the residue using Lobar column provides 1.15 g (3.10 mmol; yield, 79%) of the objective compound (IIb-2).

M.p.=107°–109° C. $^1$HNMR (CDCl$_3$) δ: 1.34 (d, J=7.0 Hz, 3H); 3.18 (s, 3H); 4.25 (q, J=7.0 Hz, 2H); 5.99 (d, J=15.2 Hz, 1H); 6.71 (dd, J=7.8,1.2 Hz, 1H); 6.86 (dd, J=15.2,10.8 Hz, 1H); 7.13–7.77 (m, 1OH). IR (Nujol): 1705, 1622, 1544. Elementary analysis (%) for $C_{20}H_{21}NO_4S$. Calc.: C,64.66, H,5.71, N,3.77, S,8.63. Found: C,64.61, H,5.69, N,3.79, S,8.51.

(2) To a solution of 320 mg (0.86 mmol) of compound (IIb-2) in a mixture of 4 ml of DMSO and 1 ml of THF is added 1.72 ml (1.72 mmol) of 1N potassium hydroxide solution and the mixture is stirred for 2 hr. The reaction mixture is partitioned between methyl ethyl ketone and 1N HCl. The organic layer is washed with water and a saturated saline, dried, filtered and concentrated. The residue is dissolved in 5 ml of ethyl acetate and the solution is filtered with Milipore and concentrated. Recrystallization from ether provides 228 mg (0.66 mmol; yield, 77%) of the objective compound (IIa-5).

M.p.=188°–190° C. $^1$HNMR (DMSO) δ: 3.14 (s, 3H); 6.04 (d, J=15.0 Hz, 1H); 6.73 (dd, J=7.8,1.2 Hz, 1H); 7.02–7.46 (m, 5H); 7.76–7.90 (m, 6H); 12.34 (brs, 1H). IR (Nujol): 3340–2000, 1678, 1618, 1592. Elementary analysis (%) for $C_{18}H_{17}NO_4S$. Calc.: C,63.00; H,5.00; N,4.08; S,9.37. Found: C,62.76; H,4.99; N,4.09; S,9.38.

(3) Compound (IIa-5) is reacted in a manner analogous to that set forth in Example 3 (3)(a) to give the objective compound (I-7) (yield, 71%).

$^1$HNMR (CDCl$_3$) δ: 3.15 (s, 3H); 5.88–6.20 (brm, 1H); 6.66–6.95 (m, 2H); 7.05–7.87 (m, 1OH). IR (Nujol): 3680–2000, 3180, 1648, 1610. Elementary analysis (%) for $C_{18}H_{18}N_2O_4S·0.2C_4H_{10}·0.2H_2O$. Calc.: C,59.92; H,5.46; N,7.43; S,8.51. Found: C,59.95; H,5.52; N,7.47; S,8.31. Mass analysis: LSIMS m/z=359 [M+H]$^+$, 717 [2M+H]$^+$.

HRLSIMS: for $C_{18}H_{19}N_2O_4S$. Calc.: 359.1065. Found: 359.1066.

EXAMPLE 5

(2E)(4E)-5-(2-Phenylsulfonylaminophenyl)-2-cyanopentadienohydroxamic Acid (I-8)

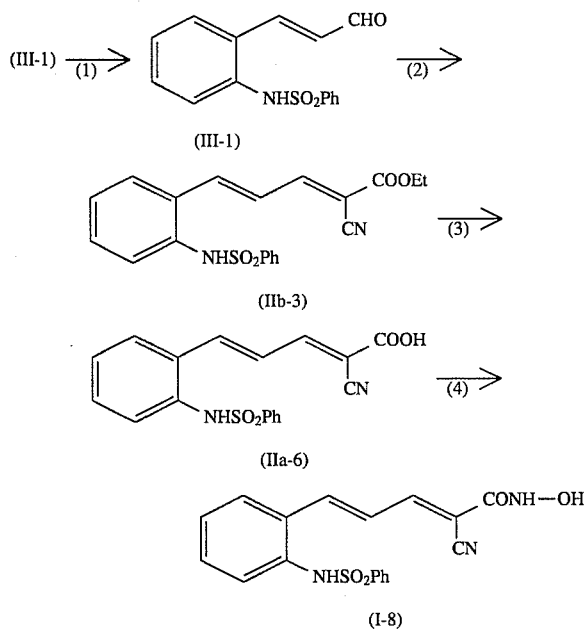

(1) To a 100 ml solution of 2.09 g (8 mmol) of compound (III-1) in benzene is added 2.92 g (9.59 mmol) of triphenylenephosphoranylidene acetaldehyde and the mixture is refluxed for 1 hr. The reaction mixture is purified by column chromatography on silica gel and crystallized from ether to yield 1.96 g (6.82 mmol; yield, 85%) of the objective compound (III'-1).

M.p.=135°–136° C. $^1$HNMR (CDCl$_3$) δ: 6.55 (dd, J=15.9, 7.6 Hz, 1H); 6.81 (brs, 1H); 7.04–7.18 (m, 1H); 7.20–7.80 (m, 9H); 9.52 (d, J=7.6 Hz, 1H). IR (KBr): 3260, 2830, 2750, 1672, 1622, 1599. Elementary analysis (%) for $C_{15}H_{13}NO_3S$. Calc.: C,62.70; H,4.56; N,4.87; S,11.16. Found: C,62.47; H,4.65; N,4.80; S,10.87.

(2) To a 12 ml solution of 1.87 g (6.51 mmol) of compound (III'-1) in dioxane are added 0.700 ml (6.58 mmol) of ethyl cyanoacetate and 48 µl (0.49 mmol) of piperidine under ice-cooling and the mixture is stirred for 8.5 hr at room temperature. The mixture is concentrated and crystallized from toluene to yield a crude product (IIb-3). Recrystallization from ethyl acetate/toluene provides 1.84 g (4.81 mmol; yield, 74%) of the purified objective compound (IIb-3).

M.p.=176°–178° C. $^1$HNMR (CDCl$_3$) δ: 1.39 (t, J=7.0 Hz, 3H); 4.36 (q, J=7.0 Hz, 2H); 6.59 (brs, 1H); 6.92–7.80 (m, 11H); 7.87 (d, J=11.2 Hz, 1H). IR (KBr): 3230, 3130, 2980, 2220, 1718, 1610, 1588, 1568, 1328, 1252, 1165, 1090, 754, 738, 551. Elementary analysis (%) for $C_{20}H_{18}N_2O_4S$. Calc.: C,62.81; H,4.74; N,7.33; S,8.38. Found: C,63.11; H,4.92; N,7.19; S,8.15.

(3) Compound (IIb-3) is reacted in a manner analogous to that described in Example 3 (2) to give the objective compound (IIa-6) (yield, 73%).

M.p.=241°–244° C. $^1$HNMR (DMSO) δ: 6.88–7.10 (m, 2H); 7.23–7.44 (m, 2H); 7.44–7.72 (m, 6H); 7.72–7.92 (m, 2H); 10.00 (brs, 1H). IR (KBR): 3700–2680, 3270, 2220, 1725, 1608, 1582, 1567, 1317, 1195, 1152, 1088, 752, 733. Elementary analysis (%) for $C_{18}H_{14}N_2O_4S \cdot 0.2H_2O$. Calc.: C,60.39; H,4.05; N,7.83; S,8.96. Found: C,60.34; H,4.01; N,7.82; S,8.76.

(4) Compound (IIa-6) (0.304 g, 8.58 mmol) is reacted in nearly the same manner as that described in Example 3 (3)(a) except that, in the final purification process, the product is washed several times with ether to yield 0.156 g (4.23 mmol; yield, 49%) of the compound (I-8) in almost pure form.

M.p.=150°–180° C. (decomp.). $^1$HNMR (DMSO) δ: 6.83–7.10 (m, 2H); 7.17–7.89 (m, 10H); 9.32 (brs, 1H); 9.99 (brs, 1H); 11.27 (brs, 1H). IR (KBr): 3680–2280, 3270, 2220, 1635, 1612, 1580, 1449, 1328, 1158, 1091, 758, 738, 688, 588, 551. Elementary analysis (%) for $C_{18}H_{15}N_3O_4S \cdot 0.2H_2O$. Calc.: C,57.96; H,4.16; N,11.27; S,8.60. Found: C,58.07; H,4.15; N,11.09; S,8.48.

EXAMPLE 6

(2E)(4E)(6E)-7-(2-Phenylsulfonylaminophenyl)-heptatrienohydroxamic Acid (I-9)

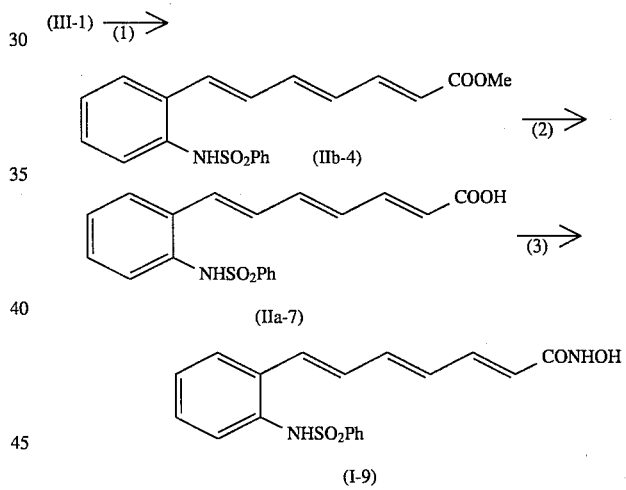

(1) To a 30 ml solution of 1.76 ml (12.6 mmol) of diisopropylamine in THF is added n-butyllithium (1.6M solution in hexane; 7.90 ml; 12.6 mmol) at −20° C. in an atmosphere of nitrogen. After stirring for 20 min at 0° C., the mixture is cooled to −78° C. To the mixture is added dropwise 20 ml solution of 2.68 g (11.4 mmol) of methyl (2E,4E)-6-dimethoxyphosphonylene-2,4-hexadienoate in THF over 20 min. The mixture is stirred for 30 min while maintaining the temperature at −78° C. Thereafter, to the mixture is added dropwise and gradually a 10 ml solution of 0.998 g (3.82 mmol) of compound (III-1) in THF over 15 min at −50° C. The reaction mixture is warmed up to room temperature over about 1.5 hr, then ammonium chloride solution and ethyl acetate are added thereto. The organic layer is washed with a saturated saline, dried, filtered and concentrated. Purification by column chromatography on silica gel and recrystallization from chloroform/methanol provides 0.733 g (1.99 mmol; yield, 52%) of the objective compound (IIb-4).

M.p.=189.5°–191° C. ¹HNMR (CDCl₃) (400 MHz) δ: 3.77 (s, 3H); 5.93 (d, J=15.3 Hz, 1H); 6.38 (dd, J=14.4,11.2 Hz, 1H); 6.51(dd, J=14.4,10.5 Hz, 1H); 6.54 (s, 1H); 6.55 (d, J=14.4 Hz, 1H); 6.63 (dd, J=14.4, 10.5 Hz, 1H); 7.17–7.26 (m, 3H); 7.33 (dd, J=15.3, 11.2 Hz, 1H); 7.40–7.49 (m,3H); 7.52–7.58 (m, 1H); 7.69–7.76 (m, 2H). IR (Nujol): 3260, 1710, 1626, 1608, 1330, 1222, 1162, 1138, 1090, 1008, 760, 739, 722, 602, 555. Elementary analysis (%) for $C_{20}H_{19}NO_4S \cdot 0.2H_2O$. Calc.: C,64.40; H,5.24; N,3.75; S,8.59. Found: C,64.56; H,5.06; N,3.77; S,8.54.

(2) To a 5.0 ml suspension of 0.500 g (1.35 mmol) of compound (IIb-4) in methanol is added 2.7 ml (2.7 mmol) of 1N potassium hydroxide solution and the mixture is stirred overnight at room temperature. When the starting materials still remain in the mixture, the stirring is continued for another 4.5 hr at 40° C. after the addition of 2.0 ml of DMSO and 1.35 ml (1.35 mmol) of potassium hydroxide. The reaction solution is partitioned between ethyl acetate and water and the organic layer is washed with water. The aqueous layers are combined and partitioned between 2N HCl and ethyl acetate. The organic layer is washed with water (×3) and a saturated saline (×1), dried, filtered and concentrated. Recrystallization from ethyl acetate/methanol provides 0.333 g (0.938 mmol; yield, 69%) of the objective compound (IIa-7).

M.p.=233.0°–234.5° C. (decomp.). ¹HNMR (DMSO) δ: 5.93 (d, J=15.2 Hz, 1H); 6.51 (dd, J=14.2, 11.2 Hz, 1H); 6.60–7.00 (m, 4H);7.10–7.40 (m, 3H); 7.46–7.72 (m, 6H); 9.88 (brs, 1H); 12.24 (brs, 1H). IR (Nujol): 3255, 1688, 1678, 1622, 1607, 1592, 1330, 1275, 1160, 1155, 1001, 756, 734. Elementary analysis (%) for $C_{19}H_{17}NO_4S$. Calc.: C,64.21; H,4.82; N,3.94; S,9.02. Found: C,64.13; H,4.85; N,4.02; S,8.84.

(3) Compound (IIa-7) is reacted in nearly the same manner as that described in Example 3 (3) (a) except that, in the final purification process, the product is washed 6–8 times with ether to yield the objective compound (I-9) (yield, 60%).

M.p.=172.5°–175.5° C. (decomp.). ¹HNMR (DMSO) δ: 5.92 (d, J=15.1 Hz, 1H); 6.37–7.02 (m, 5H); 7.06–7.40 (m, 3H); 7.46–7.80 (m, 6H); 8.98 (brs, 1H); 9.85 (brs, 1H); 10.68 (brs, 1H). IR (Nujol): 3285, 1653, 1622, 1607, 1598, 1568, 1146, 1087, 1042, 755, 739. Elementary analysis (%) for $C_{19}H_{18}N_2O_4S$. Calc.: C,61.61; H,4.90; N,7.56; S,8.65. Found: C,61.56; H,5.02; N,7.34; S,8.44.

EXAMPLE 7

(2E)(4E)-5-(3-Phenylsulfonylaminophenyl) pentadienohydroxamic Acid (I-10)

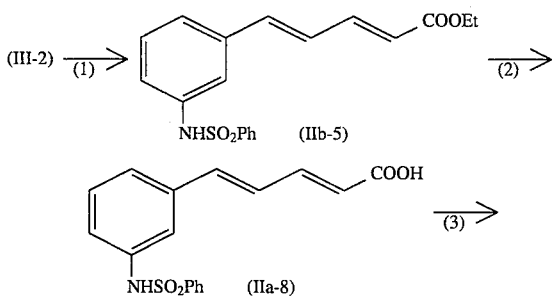

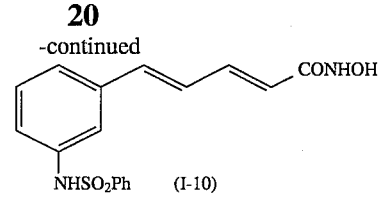

(1) Compound (III-2) is reacted in an analogous manner to that described in Example 3 (1) to obtain a crude product as a mixture of cis- and trans-isomers. It is subjected to chromatography over silica gel to remove reagents and to Lobar column chromatography (×2) to separate the objective compound (IIb-5) in trans form (yield, 21%).

M.p.=105°–106° C. ¹HNMR (CDCl₃) δ: 1.32 (t, J=7.2 Hz, 3H); 4.23 (q, J=7.2 Hz, 2H); 5.99 (d, J=15.2 Hz, 1H); 6.68–6.92 (m, 3H); 6.92–7.09 (m, 1H); 7.13–7.30 (m, 3H); 7.30–7.62 (m, 4H); 7.72–7.86 (m, 2H). IR (KBr): 3220, 2980, 1682, 1628, 1581, 1340, 1330, 1248, 1180, 1157, 989, 685, 581, 550. Elementary analysis (%) for $C_{19}H_{19}NO_4S \cdot 0.1H_2O$. Calc.: C,63.53; H,5.39; N,3.90; S,8.92. Found: C,63.45; H,5.25; N,3.96; S,8.91.

(2) To a 30 ml solution of 291 mg (0.813 mmol) of compound (IIb-5) in DMSO is added 1.64 ml (1.64 mmol) of 1 N sodium hydroxide solution and the mixture is stirred for 2 hr at room temperature. First, the mixture is partitioned between ethyl acetate and water and the aqueous layer is then partitioned between ethyl acetate and 2N HCl. The organic layer is washed with water (×3) and a saturated saline (×1), dried, filtered and concentrated under reduced pressure. Crystallization provides 228 mg (0.693 mmol; yield, 85%) of the compound (IIa-8).

M.p.=188°–190° C. ¹HNMR (DMSO) δ: 6.04 (d, J=15.2 Hz, 1H); 6.87–7.10 (m, 3H); 7.16–7.41 (m, 4H); 7.48–7.68 (m, 3H); 7.72–7.85 (m, 2H); 10.38 (brs, 1H); 12.25 (brs,1H). IR (KBr): 3680–2000, 3239, 1678, 1610, 1530, 1328, 1309, 1270, 1152, 1155, 1091, 998, 685, 581, 549. Elementary analysis (%) for $C_{17}H_{15}NO_4S$. Calc.: C,61.99; H,4.59; N,4.25; S,9.73. Found: C,61.89; H,4.69; N,4.17; S,9.57.

(3) Compound (IIa-8) is reacted in a manner analogous to that set forth in Example 3 (3) (a) to give the objective compound (I-10) (yield, 86%).

M.p.=94°–111° C. (decomp.). ¹HNMR (DMSO) δ: 6.01 (d, J=14.8 Hz, 1H); 6.75–6.95 (m, 2H); 6.95–7.10 (m, 1H); 7.10–7.35 (m, 4H); 7.46–7.69 (m, 3H); 7.69–7.87 (m, 2H); 8.98 (brs, 1H); 10.35 (s, 1H); 10.74 (s, 1H). IR (KBr): 3680–2000, 1642, 1612, 1580. Elementary analysis (%) for $C_{17}H_{16}N_2O_4S \cdot 0.1H_2O \cdot 0.25C_4H_{10}O$. Calc.: C,59.28; H,5.17; N,7.68; S,8.79. Found: C,59.21; H,5.18; N,7.90; S,8.79. Mass analysis: LSIMS m/z=345 [M+H]+, 689 [2M+H]+. HRLSIMS: for $C_{17}H_{17}N_2O_4S$. Calc.: 345.0908. Found: 345.0911.

EXAMPLE 8

(2E)(4E)-5-[3-(N-Methylphenylsulfonylaminophenyl) pentadienohydroxamic Acid (I-11)

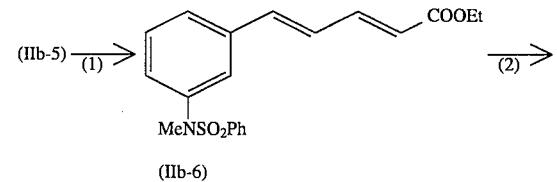

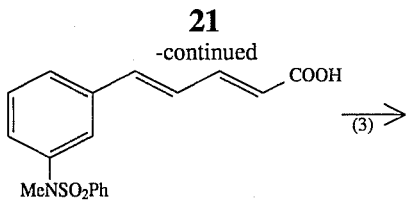

(IIa-9)

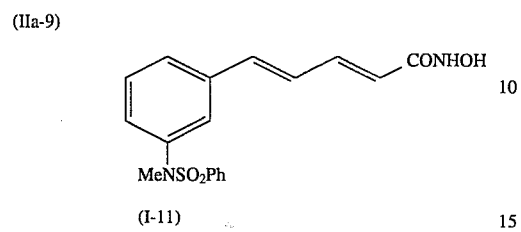

(I-11)

(1) Compound (IIb-5) is reacted in a manner analogous to that set forth in Example 4 (1) and purified by chromatography on silica gel to give the objective compound (IIb-6) (yield, 85%).

M.p.=103°–105° C. $^1$HNMR (CDCl$_3$) 1.32 (t, J=7.2 Hz, 3H); 3.19 (S, 3H); 4.23 (q, J=7.2 Hz, 2H); 5.99 (d, J=15.2 Hz, 1H); 6.66–6.91 (m, 2H); 6.91–7.06 (m, 1H); 7.14–7.68 (m, 9H). IR (KBr): 2980, 1700, 1620, 1577, 1345, 1331, 1309, 1241, 1176, 1165, 1132, 1009, 830, 729, 688, 590, 562. Elementary analysis (%) for C$_{20}$H$_{21}$NO$_4$S. Calc.: C,64.67; H,5.70; N,3.77; S,8.63. Found: C,64.74; H,5.80; N,3.74; S,8.36.

(2) Compound (IIb-6) is subjected to hydrolysis in a manner analogous to that set forth in Example 7 (2) to give the compound (IIa-9) (yield, 70%).

M.p.=165°–169° C. $^1$HNMR (DMSO) δ: 3.16 (s, 3H); 6.02 (d, J=15.0 Hz, 1H); 6.92–7.17 (m, 3H); 7.20–7.43 (m, 3H); 7.43–7.80 (m, 6H); 12.31 (brs, 1H). IR (KBr): 3680–2000, 3000, 1683, 1612, 1578, 1445, 1349, 1308, 1272, 1256, 1168, 1151, 995, 729, 689, 588, 561. Elementary analysis (%) for C$_{18}$H$_{17}$NO$_4$S. Calc.: C,62.96; H,4.99; N,4.08; S,9.34. Found: C,62.69; H,5.12; N,4.03; S,9.05.

(3) Compound (IIa-9) is reacted in a manner analogous to that set forth in Example 3 (3) (a) to give the objective compound (I-11) (yield, 87%). $^1$HNMR (DMSO) δ: 3.15 (s, 3H); 6.01 (d, J=14.8 Hz, 1H); 6.80–7.42 (m, 6H); 7.42–7.83 (m, 6H); 9.00 (s, 1H); 10.78 (s, 1H). IR (KBr): 3700–2000, 1645, 1612. Mass analysis: LSIMS m/z=359 [M+H]+, 717 [2M+H]+. HRLSIMS: for C$_{18}$H$_{19}$N$_2$O$_4$S. Calc.: 359.1065. Found: 359.1072.

EXAMPLE 9

(2E)(4E)-5-(4-Phenylsulfonylaminophenyl)pentadienohydroxamic Acid (I-12)

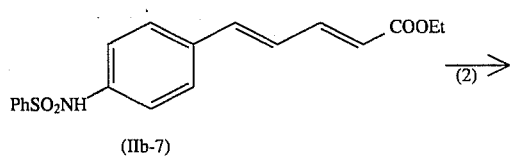

(IIb-7)

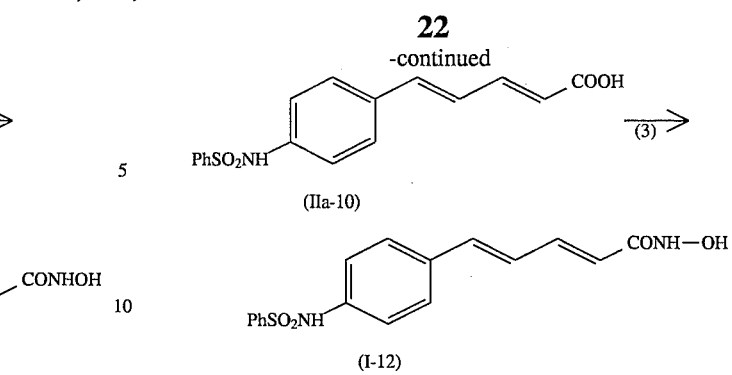

(1) To a 50 ml suspension of 7.08 g (15.5 mmol) of 4-ethoxycarbonylene-2-propenylenetriphenylenephosphonium bromide in THF is added 1.68 g (15.0 mmol) of potassium tert-butoxide at 0° C. in an atmosphere of nitrogen and the mixture is stirred for 30 min at room temperature and then cooled again to 0° C. To the mixture is added dropwise a 15 ml solution of 1.31 g (5.01 mmol) of compound (III-3) in THF over 5 min followed by stirring for 30 min at 0° C. The reaction is carried out for 3 hr at room temperature and overnight under heating to reflux. The reaction mixture is then partitioned between ethyl acetate and 2N HCl. The organic layer is washed with water and a saturated saline, dried, filtered and concentrated. Purification by column chromatography on silica gel and recrystallization from ether/hexane/ethyl acetate provides 0.343 g (0.960 mmol; yield, 19%) of the compound (IIb-7).

M.p.=166°–169° C. $^1$HNMR (CDCl$_3$) δ: 1.31 (t, J=7.2 Hz, 3H); 4.22 (q, J=7.2 Hz, 2 H); 5.96 (d, J=15.2 Hz, 1H); 6.66–6.86 (m, 2H); 6.95 (brs, 1H); 7.02–7.12 (m, 2H); 7.29–7.61 (m, 6H); 7.76–7.86 (m, 2H). IR (KBr): 3210, 1682, 1623, 1602, 1510, 1470, 1370, 1344, 1332, 1310, 1252, 1155, 1142, 1088, 998, 918, 844, 575. Elementary analysis (%) for C$_{19}$H$_{19}$NO$_4$S•0.1H$_2$O. Calc.: C,63.52; H,5.39; N, 3.80; S,8.92. Found: C,63.41; H,5.51; N, 3.80; S,8.97.

(2) Compound (IIb-7) is hydrolyzed in a manner analogous to that set forth in Example 6 (2) using sodium hydroxide solution to yield the compound (IIa-10) (yield, 92%).

M.p.=261°–270° C. (decomp.). $^1$HNMR (DMSO) δ: 5.94 (d, J=15.2 Hz, 1H); 6.84–7.06 (m, 2H); 7.06–7.20 (m, 2H); 7.20–7.37 (m, 1H); 7.37–7.49 (m, 2H); 7.49–7.68 (m, 3H); 7.74–7.86 (m, 2H). IR (KBr): 3680–2000, 3280, 1670, 1618, 1600, 1508. Mass analysis: LSIMS m/z=330 [M+H]+, 659 [2M+H]+. HRLSIMS: for C$_{17}$H$_{16}$NO$_4$S. Calc.: 330.0799. Found: 330.0797.

(3) Compound (IIa-10) is treated in a manner analogous to that set forth in Example 3 (3) (a) and further washed with ether to yield the objective compound (I-12) (yield, 49%).

M.p.=171°–175° C. (decomp.). $^1$HNMR (DMSO) δ: 5.94 (d, J=15.0 Hz, 1H); 6.74–7.28 (m, 5H); 7.35–7.49 (m, 2H); 7.49–7.67 (m, 3H); 7.72–7.84 (m, 2H); 8.95 (brs, 1H); 10.20–10.90 (m, 2H). IR (KBr): 3280, 3140, 2930, 2860, 1645, 1610, 1598, 1508. Elementary analysis (%) for C$_{17}$H$_{16}$N$_2$O$_4$S•0.1H$_2$O. Calc.: C,58.98; H,4.72; N,8.09; S,9.26. Found: C,58.91; H,4.71; N,8.12; S,9.04.

EXAMPLE 10

(2E)(4E)-5-(4,5-Dimethoxy-2-phenylsulfonylaminophenyl)pentadienohydroxamic Acid (I-13) and (2E)(4E)-5-(4,5-dihydroxy-2-phenylsulfonylaminophenyl)pentadienohydroxamic Acid (I-14)

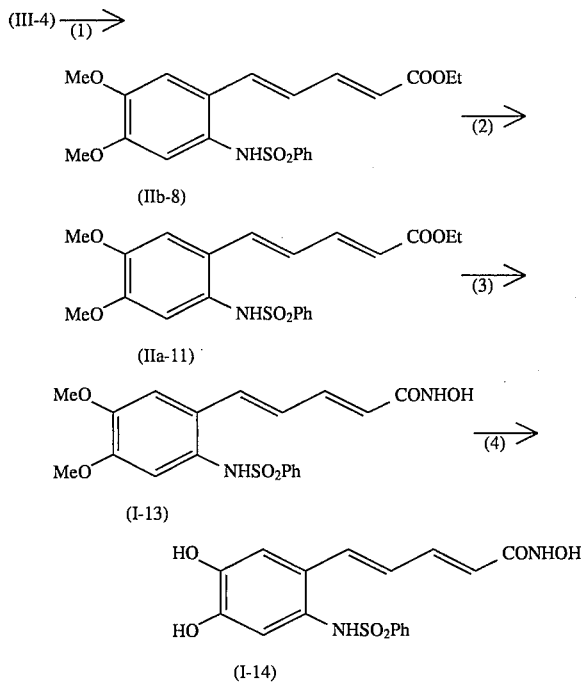

(1) Compound (III-4) is reacted in a manner analogous to that set forth in Example 3 (1) to yield the objective compound (IIb-8) (yield, 74%).

M.p.=199°–201° C. $^1$HNMR (CDCl$_3$) δ: 1.33 (t, J=7.2 Hz, 3H); 3.76 (s, 3H); 3.90 (s,3H); 4.24 (q, J=7.2 Hz, 2H); 5.89 (d, J=15.2 Hz, 1H); 6.43 (s, 1H); 6.43–6.73 (m, 2H); 6.65 (s, 1H);6.93 (s, 1H); 7.16 (dd, J=15.2 Hz, 10.2 Hz, 1H); 7.38–7.62 (m, 3H); 7.65–7.78 (m, 2H). IR (Nujol): 3280, 3200, 1702, 1692, 1622, 1602, 1519. Elementary analysis (%) for $C_{21}H_{23}NO_6S \cdot 0.2H_2O$. Calc.: C,59.89; H,5.61; N,3.33; S,7.61. Found: C,59.79; H,5.49; N,3.45; S,7.37.

(2) To a 10 ml solution of 2.09 g (5.01 mmol) of compound (IIb-8) in DMSO is added 10.0 ml (10.0 mmol) of 1N potassium hydroxide and the mixture is stirred for 2 hr at room temperature and for 1 hr at 45° C. The reaction mixture is partitioned between methyl ethyl ketone and 2N HCl. The organic layer is washed with water (×3) and a saturated saline (×1). Each aqueous layer is again extracted with ethyl acetate. The organic layers are combined, dried, filtered and concentrated. The crude crystals, when washed with ether, gives 1.90 g (4.88 mmol; yield, 98%) of the objective compound (IIa-11).

M.p.=237°–240° C. $^1$HNMR (DMSO) δ: 3.55 (s, 3H); 3.79 (s, 3H); 5.87 (d, J=15.0 Hz,1H); 6.40 (s, 1H); 6.75–6.97 (m, 2H); 7.06 (ddd, J=15.0, 8.0, 3.0 Hz, 1H); 7.16 (s, 1H); 7.45–7.74 (m, 5H); 9.68 (brs, 1H); 12.20 (brs, 1H). IR (Nujol): 3275, 1682, 1622, 1600, 1520. Elementary analysis (%) for $C_{19}H_{19}NO_6S$. Calc.: C,58.59; H,4.93; N,3.60; S,8.23. Found: C,58.56; H,5.20; N,3.53; S,7.93.

(3) To an 8 ml suspension of 779 mg (2.00 mmol) of compound (IIa-11) in methylene chloride is added oxalyl chloride alone. A drop of DMF is added only when the evolution of gas is not observed. The reaction is carried out in an almost the same manner as that set forth in Example 3 (3) (a) to yield 524 mg (1.30 mmol, yield, 65%) of the objective compound (I-13).

M.p.=218°–220° C. $^1$HNMR (DMSO) δ: 3.55 (s, 3H); 3.79 (s, 3H); 5.89 (d, J=14.0 Hz, 1H); 6.39 (s, 1H); 6.66–7.09 (m, 3H); 7.17 (s, 1H); 7.45–7.73 (m, 5H); 8.96 (brs, 1H); 9.65 (brs,1H); 10.71 (brs, 1H). IR (Nujol): 3305, 3120, 1638, 1594, 1516. Elementary analysis (%) for $C_{19}H_{20}N_2O_6S$. Calc.: C,56.42; H,4.99; N,6.93; S,7.93. Found: C,56.18; H,5.12; N,6.90; S,7.68.

(4) To a 30 ml suspension of 202 mg (0.500 mol) of compound (I-13) in methylene chloride is added 95 μl (1.00 mmol) of boron tribromide at room temperature in an atmosphere of nitrogen and the mixture is stirred for overnight. The reaction mixture is partitioned between ethyl acetate and water. The organic layer is washed with water (×2) and a saturated saline (×1), dried, filtered and concentrated. The resultant crude product, when washed with ether, gives 0.123 g (0.327 mmol; yield, 65%) of the objective compound (I-14). $^1$HNMR (DMSO) δ: 5.83 (d, J=14.6 Hz, 1H); 6.33–6.74 (m, 3H); 6.76–7.01 (m, 2H); 7.37–7.71 (m, 5H); 8.60–9.75 (m, 1H); 9.05 (s, 1H); 9.48 (s, 1H); 9.52 (s, 1H); 10.62 (s, 1H). IR (Nujol): 3450, 3315, 3120, 1640, 1622, 1595, 1515. Elementary analysis (%) for $C_{17}H_{16}N_2O_6S \cdot 0.5H_2O$. Calc.: C,52.97; H,4.45; N,7.27; S,8.32. Found: C,52.75; H,4.40; N,6.95; S,8.27.

EXAMPLE 11

(2E)-(1-Phenylsulfonylindol-2-yl)propenohydroxamic Acid (I-15)

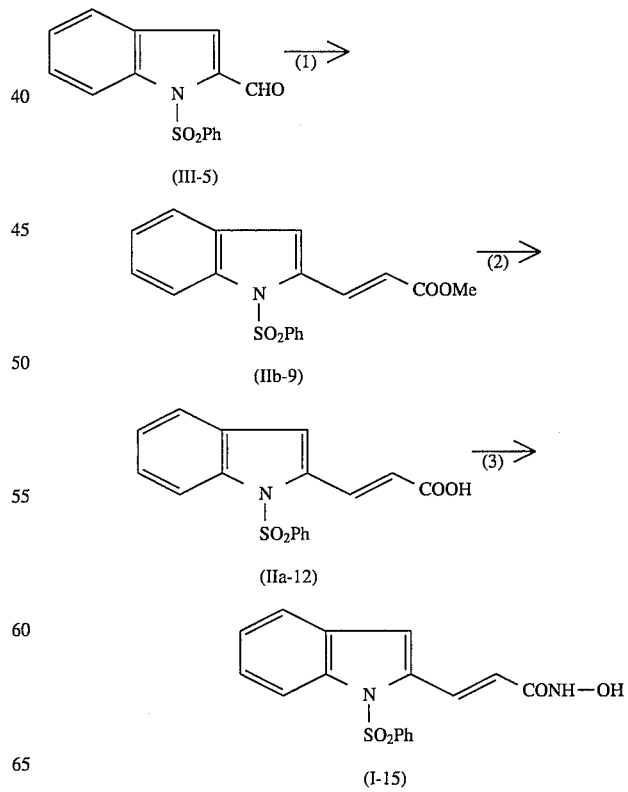

(1) To a 50 ml solution of 1.75 ml (10.8 mmol) of trimethyl phosphonoacetate in THF is added at once 0.420 g (10.5 mmol) of 60% (in oil) sodium hydride at 0° C. in an atmosphere of nitrogen. After stirring for 1 hr at room temperature, a 12 ml solution of 1.03 g (3.62 mmol) of compound (III-5) in THF is added to the mixture gradually. After stirring for 60 min at room temperature, the reaction mixture is partitioned between ethyl acetate and 2N HCl. The organic layer is washed with water and a saturated saline, dried, filtered and concentrated. The residue, when purified by chromatography on silica gel and recrystallized from methylene chloride/ether/hexane, gives 0.872 g (2.55 mol; yield, 71%) of the objective compound (IIb-9).

M.p.=140°–142° C. $^1$HNMR (CDCl$_3$) δ: 3.85 (s, 3H); 6.38 (d, J=16.0 Hz, 1H); 6.98 (s, 1H); 7.21–7.57 (m, 6H); 7.70–7.80 (m, 2H); 8.23 (dd, J=8.4,1.0 Hz, 1H); 8.39 (dd, J=16.0,1.0 Hz, 1H). IR (KBr): 3060, 2950, 1709, 1625, 1580, 1542, 1369, 1332, 1222, 1208, 1167, 738, 725, 585, 568. Elementary analysis (%) for C$_{18}$H$_{15}$NO$_4$S. Calc.: C,63.33; H,4.43; N,4.10; S,9.39. Found: C,63.32; H,4.52; N,4.10; S,9.46.

(2) Compound (IIb-9) is reacted in a manner analogous to that set forth in Example 6 (2) using sodium hydroxide aqueous solution to yield the objective compound (IIa-12) (yield, 40%).

M.p.=214°–218° C. $^1$HNMR (DMSO) δ: 6.60 (d, J=15.8 Hz, 1H); 7.23–7.80 (m, 9H); 8.12 (d, J=8.4 Hz, 1H); 8.22 (dd, J=15.8 Hz, 0.7 Hz, 1H); 12.70 (brs, 1H). IR (KBr): 3660–2000, 1681, 1620, 1542, 1448, 1418, 1378, 1330, 1270, 1225, 1191, 1172, 1145, 758, 585, 565. Elementary analysis (%) for C$_{17}$H$_{13}$NO$_4$S. Calc.: C,62.37; H,4.00; N,4.28; S,9.79. Found: C,62.46; H,4.14; N,4.38; S,9.51.

(3) Compound (IIa-12) is reacted in a manner analogous to that set forth in Example 3 (3) (a) to yield the objective compound (I-15) (yield, 93%).

M.p.=179°–184° C. (decomp.). $^1$HNMR (DMSO) δ: 6.47 (d, J=15.8 Hz, 1H); 7.22 (brs, 1H); 7.24–7.80 (m, 8H); 7.95–8.16 (m, 2H); 9.19 (brs, 1H); 10.91 (brs, 1H). IR (KBr): 3680–2400, 3370, 3120, 2860, 1658, 1618, 1445, 1358, 1170, 1145, 1086, 755, 728, 581, 568. Elementary analysis (%) for C$_{17}$H$_{14}$N$_2$O$_4$S. Calc.: C,59.64; H,4.12; N,8.18; S,9.36. Found: C,59.37; H,4.18; N,7.92; S,9.11.

EXAMPLE 12

(2E)(4Z)-5-(1-phenylsulfonylindol-2-yl)pentadienohydroxamic Acid (I-16) and (2E)(4E)-5-(1-phenylsulfonylindol-2-yl)pentadienohydroxamic Acid (I-17)

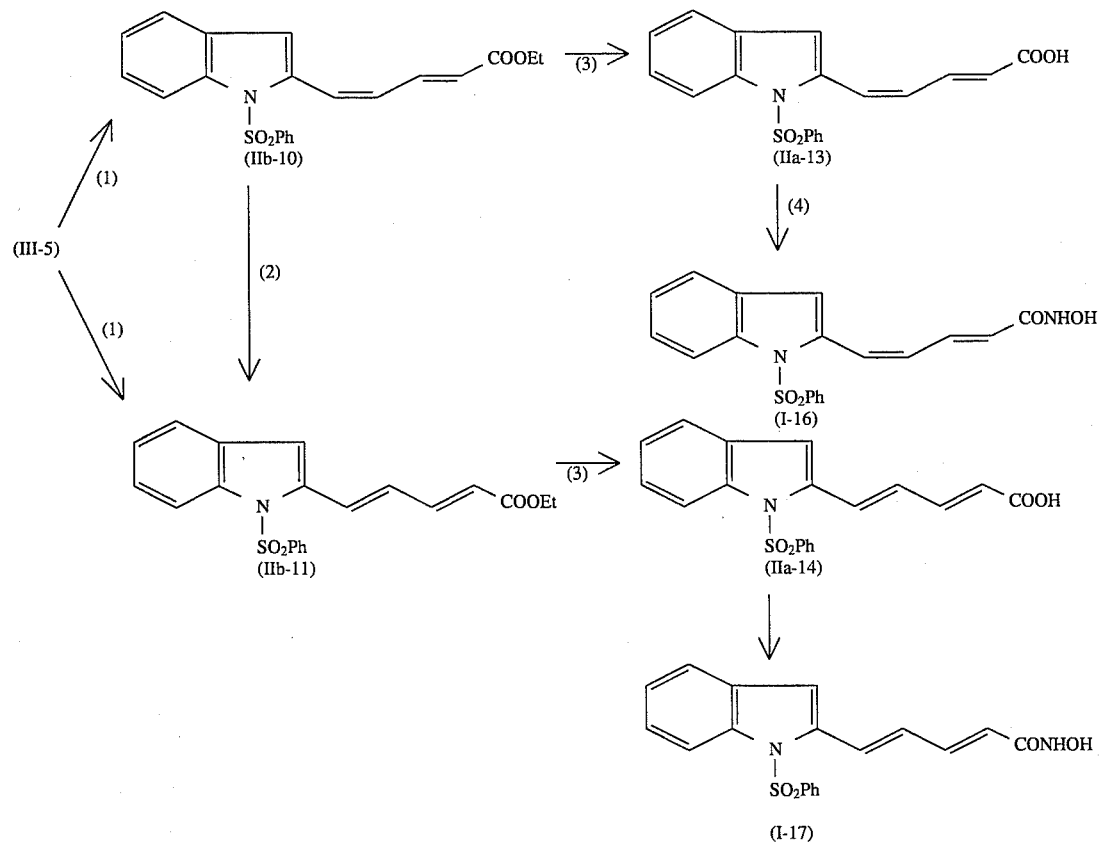

(1) Compound (III-5) is reacted in a manner analogous to that set forth in Example 3 (1) to obtain a reaction mixture containing cis-isomer (IIb-10) and trans-isomer (IIb-11). The resultant mixture is subjected to chromatography on silica gel to remove side products originated from reagents and then to Lobar column chromatography to separate the cis-isomer (IIb-10) and trans-isomer (IIb-11) from each other.

Compound (IIb-10): yield, 57%.

M.p.=108°–111° C. $^1$HNMR (CDCl$_3$) δ: 1.28 (t, J=7.0 Hz, 3H); 4.20 (q, J=7.0 Hz, 2H); 6.12 (d, J=15.2 Hz, 1H); 6.54 (t, J=11.5 Hz, 1H); 6.67 (s, 1H); 7.13–7.77 (m, 10H); 8.21 (d, J=8.6 Hz, 1H). IR (KBr): 2970, 1708, 1620, 1580, 1445, 1367, 1263, 1250, 1171, 1141, 1088, 1040, 1032, 721, 689, 598, 562. Elementary analysis (%) for $C_{21}H_{19}NO_4S$. Calc.: C,66.13; H,5.02; N,3.67; S,8.40. Found: C,65.98; H,5.03; N,3.86; S,8.14.

Compound (IIb-11): yield, 6%.

M.p.=120°–122° C. $^1$HNMR (CDCl$_3$) δ: 1.34 (t, J=7.2 Hz, 3H); 4.26 (q, J=7.2 Hz, 2H); 6.01 (d, J=15.2 Hz, 1H); 6.81 (ddd, J=15.5,11.1,0.7 Hz, 1H); 6.92 (s, 1H); 7.17–7.66 (m, 8H); 7.66–7.78 (m, 2H); 8.21 (d, J=8.2 Hz, 1H). IR (KBr): 3060, 2980, 1701, 1628, 1541, 1445, 1368, 1308, 1242, 1181, 1170, 1151, 1131, 745, 588, 564. Elementary analysis (%) for $C_{21}H_{19}NO_4S \cdot 0.2H_2O$. Calc.: C,65.51; H,5.08; N,3.64; S,8.33. Found: C,65.51; H,5.06; N,3.68; S,8.44.

(2) To an 8 ml solution of 0.593 g (1.55 mmol) of compound (IIb-10) in methylene chloride is added 0.121 g (0.475 mmol) of iodine and the mixture is stirred for 2 days at room temperature. The reaction mixture is partitioned between ethyl acetate and sodium thiosulfate solution. The organic layer is washed with a saturated saline, dried, filtered and concentrated. The crude product, when purified by chromatography on silica gel and Lobar column chromatography, gives 0.194 g (0.509 mmol; yield, 33%) of the objective compound (IIb-11).

(3) Compounds (IIb-10) and (IIb-11) each are subjected to hydrolysis in a manner analogous to that described in Example 7 (2) to give the objective compounds (IIa-13) (yield, 68%) and (IIa-14) (yield, 43%).

Compound (IIa-13):

M.p.=196°–199° C. $^1$HNMR (DMSO) δ: 6.21 (d, J=15.2 Hz, 1H); 6.74 (t, J=11.7 Hz, 1H); 6.86 (s, 1H); 7.15 (d, J=11.4 Hz, 1H); 7.23–7.78 (m, 9H); 8.12(d, J=8.2 Hz, 1H); 12.43 (brs, 1H). IR (KBr): 3680–2000, 1678, 1615, 1580, 1371, 1278, 1174, 1039, 721, 590, 568, 551. Elementary analysis (%) for $C_{19}H_{15}NO_4S$. Calc.: C,63.92; H,4.35; N,3.92; S,8.98. Found: C,63.92; H,4.60; N,3.88; S,8.93.

Compound (IIa-14):

M.p.=202°–210° C. (decomp.). $^1$HNMR (DMSO) δ: 6.07 (d, J=15.0 Hz, 1H); 7.11 (dd, J=15.2, 11.2 Hz, 1H); 7.22–7.64 (m, 9H); 7.68–7.87 (m, 2H); 8.11 (d, J=8.0 Hz, 1H). IR (KBr): 3700–2000, 1688, 1612, 1582, 1448, 1378, 1308, 1265, 1182, 1170, 1152, 1090, 745, 588, 570, 560. Mass analysis: LSIMS m/z=354 [M+H]+, 707 [2M+H]+. HRSIMS: for $C_{19}H_{16}NO_4S$. Calc.: 354.0799. Found: 354.0799.

(4) Compounds (IIa-13) and (IIa-14) each are reacted in a manner analogous to that set forth in Example 7 (3) to obtain the objective compounds (I-16) (yield, 95%) and (I-17) (yield, 81%), respectively.

Compound (I-16):

M.p.=152°–156° C. (decomp.). $^1$HNMR (DMSO) δ: 6.17 (d, J=15.0 Hz, 1H); 6.69 (t, J=11.6 Hz, 1H); 6.82 (s, 1H); 7.06 (d, J=11.2 Hz, 1H); 7.20–7.75 (m, 9H); 8.11(d, J=8.2 Hz, 1H); 9.02 (brs, 1H);10.82 (brs, 1H). IR (Nujol): 3330, 1626, 1590, 1558. Mass analysis: LSIMS m/z=369 [M+H]+, 737 [2M+H]+. HRLSIMS: for $C_{19}H_{17}N_2O_4S$. Calc.: 369.0908. Found: 369.0909.

Compound (I-17):

M.p.=149°–158° C. (decomp.). $^1$HNMR (DMSO) δ: 6.07 (d, J=15.0 Hz, 1H); 7.10 (dd, J=15.2, 11.0 Hz, 1H); 7.20–7.72 (m, 10H); 7.72–7.90 (m, 2H); 9.04 (brs, 1H); 10.81 (brs, 1H). IR (KBr): 3680–2100, 1632, 1600, 1535, 1448, 1379, 1171, 1091, 1050, 989, 748, 588, 568, 556. Elementary analysis (%) for $C_{19}H_{16}N_2O_4S \cdot 0.3H_2O$. Calc.: C,61.05; H,4.48; N,7.49; S,8.58. Found: C,61.15; H,4.60; N,7.28; S,8.36.

EXAMPLE 13

(2E)-5-[3-(Phenylsulfonylamino)phenyl]pent-2-en-4-ynohydroxamic Acid (I-18)

(III-6) —(1)→

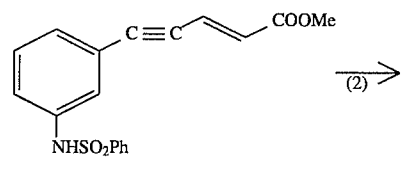

(IIb-12)

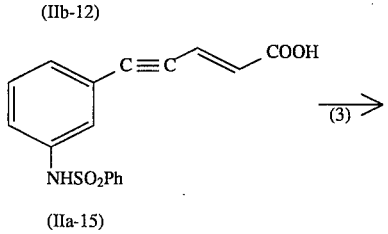

(IIa-15)

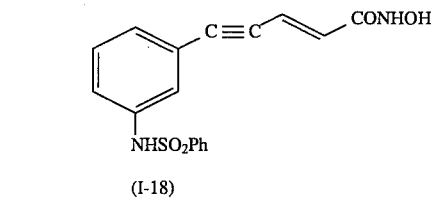

(I-18)

(1) Compound (III-6) is reacted in a manner analogous to that set forth in Example 11 (1) to obtain the objective compound (IIb-12) (yield, 81%).

M.p.=134°–137° C. $^1$HNMR (CDCl$_3$) δ: 3.79 (s, 3H); 6.30 (d, J=16.0 Hz, 1H); 6.93 (brs, 1H); 6.95 (d, J=16.0 z, 1H); 7.04–7.32 (m, 4H); 7.37–7.64 (m, 3H); 7.71–7.86 (m, 2H). IR (KBr): 3230,2190, 1692, 1613, 1599, 1578, 1468, 1445, 1330, 1291, 1175, 1155, 1089, 952, 681, 582, 516. Elementary analysis (%) for $C_{18}H_{15}NO_4S \cdot 0.5H_2O$. Calc.: C,61.70; H,4.60; N,4.00; S,9.15. Found: C,61.87; H,4.47; N,3.98; S,9.09.

(2) Compound (IIb-12) is hydrolyzed in a manner analogous to that set forth in Example 7 (2) to obtain the objective compound (IIa-15) (yield, 77%).

M.p.=187°–188° C. $^1$HNMR (DMSO) δ: 6.34 (d, J=15.9 Hz, 1H); 6.90 (d, J=15.9 Hz, 1H); 7.07–7.40 (m, 4H);7.47–7.70 (m, 3H); 7.70–7.85 (m, 2H); 10.55 (brs, 1H); 12.76 (brs, 1H). IR (KBr): 3660–2020, 3250, 2190, 1680, 1610, 1578, 1500. Elementary analysis (%) for $C_{17}H_{13}NO_4S \cdot 0.2H_2O$. Calc.: C,61.70; H,4.08; N,4.23; S,9.69. Found: C,61.95; H,4.22; N,4.12; S,9.44.

(3) Compound (IIa-15) is reacted in a manner analogous to that set forth in Example 3 (3) (a) to obtain the objective compound (I-18) (yield, 100%).

$^1$HNMR (DMSO) δ: 6.33 (d, J=15.5 Hz, 1H); 6.74 (d, J=15.5 Hz, 1H); 7.05–7.37 (m, 4H);7.48–7.70 (m, 3H); 7.70–7.85 (m, 2H); 9.26 (brs, 1H); 10.2–11.1 (m,2H). IR (KBr): 3680–2000, 2198, 1648, 1612, 1578. Mass analysis: LSIMS m/z=343 [M+H]+, 685 [2M+H]+. HRLSIMS: for $C_{17}H_{15}N_2O_4S$. Calc.: 343.0752. Found: 343.0755.

EXAMPLE 14

(2E)-5-[3-(N-Methylphenylsulfonylamino)phenyl]
pent-2-en-4-ynohydroxamic Acid (I-19)

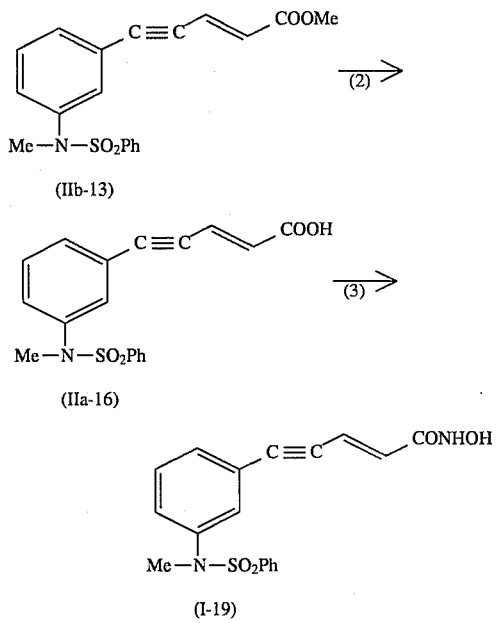

(1) To a 10.0 ml solution of 0.538 g (1.58 mmol) of compound (IIb-12) in acetone are added 1.09 g (7.89 mmol) of potassium carbonate and 0.450 ml (4.75 mmol) of dimethyl sulfate and the mixture is refluxed for 1 hr. The reaction mixture is filtered to remove potassium carbonate and the filtrate is partitioned between ethyl acetate and 2N HCl. The organic layer is washed with water and a saturated saline, dried, filtered and concentrated. Recrystallization from ether/methylene chloride gives 0.442 g (1.24 mmol; yield, 79%) of the objective compound (IIb-13).

M.p.=91°–92° C. $^1$HNMR (CDCl$_3$) δ: 3.17 (s, 3H); 3.79 (s, 3H); 6.30 (d, J=15.8 Hz, 1H); 6.95 (d, J=15.8 Hz, 1H); 7.10–7.67 (m, 9H). IR (KBr): 3060, 2945, 2190, 1711, 1620, 1588, 1570, 1445, 1358,1352, 1318, 1170, 1153, 1088, 762, 729,689,582, 565. Elementary analysis (%) for $C_{19}H_{17}NO_4S \cdot 0.2H_2O$. Calc.: C,63.57; H,4.89; N,3.90; S,8.93. Found: C,63.73; H,4.80; N,3.88; S,8.82.

(2) Compound (IIb-13) is hydrolyzed in a manner analogous to that set forth in Example 7 (2) to obtain the objective compound (IIa-16) (yield, 86%).

M.p.=160°–162° C. $^1$HNMR (DMSO) δ: 3.15 (s, 3H); 6.35 (d, J=15.8 Hz, 1H); 6.90 (d, J=15.8 Hz, 1H); 7.16–7.30 (m, 2H); 7.35–7.79 (m, 7H). IR (KBr): 3640–2040, 2195, 1700, 1612, 1572. Elementary analysis (%) for $C_{18}H_{15}NO_4S$. Calc.: C,63.33; H,4.43; N,4.10; S,9.39. Found: C,63.07; H,4.43; N,4.12; S,9.31.

(3) Compound (IIa-16) is reacted in a manner analogous to that set forth in Example 3 (3) (a) to obtain the objective compound (I-19) (yield, 100%) as a powder.

$^1$HNMR (DMSO) δ: 3.15 (s, 3H); 6.34 (d, J=15.7 Hz, 1H); 6.74 (d,J=15.7 Hz, 1H); 7.14–7.29 (m, 2H); 7.33–7.78 (m, 7H); 9.24 (brs, 1H); 10.90 (brs, 1H). IR (KBr): 3680–2040, 2190, 1650, 1611, 1570. Mass analysis: LSIMS m/z= 357 [M+H]+, 713 [2M+H]+. HRLSIMS: for $C_{18}H_{17}N_2O_4S$. Calc.: 357.0908. Found: 357.0910.

EXAMPLE 15

(2E)(4E)-5-(3'-Phenylsulfonylamino-2'-naphthyl)pentadienohydroxamic Acid (I-20)

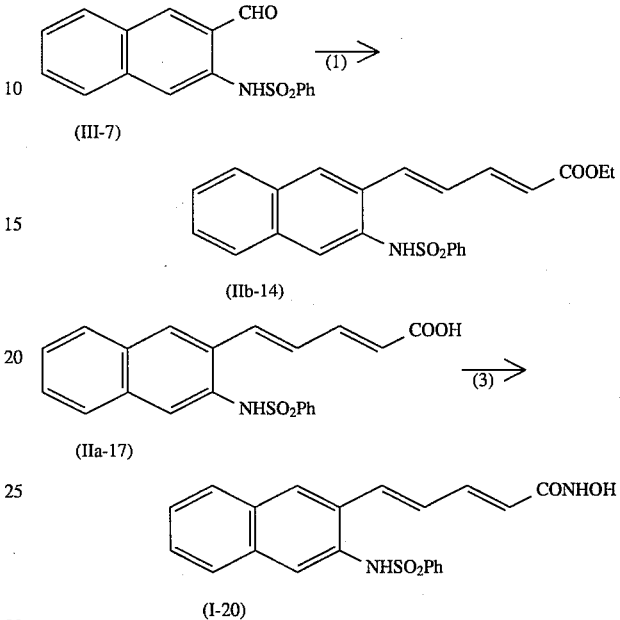

(1) Compound (III-7) is subjected to the Wittig reaction in a manner similar to that set forth in Example 3 (1). The resultant crude product, when purified by Lobar column chromatography and recrystallized from ethyl acetate/hexane, gives the objective compound (IIb-14) (yield, 74%).

M.p.=155°–156° C. $^1$HNMR (CDCl$_3$) δ: 1.34 (t, J=7.0 Hz, 3H); 4.26 (q, J=7.0 Hz, 2H); 5.97 (d, J=15.2 Hz, 1H); 6.63 (s, 1H); 6.74 (dd, J=15.2 Hz, J=10.0 Hz, 1H); 6.86 (d, J=15.2 Hz); 7.22–7.59 (m, 6H); 7.68–7.83 (m, 5H); 7.93 (s, 1H). IR (Nujol): 3280, 1687. Elementary analysis (%) for $C_{23}H_{21}NO_4S$. Calc.: C,67.79; H,5.19; N,3.44; S,7.87. Found: C,68.02; H,5.31; N,3.51; S,7.68.

(2) Compound (IIb-14) is hydrolyzed with potassium hydroxide in a manner analogous to that set forth in Example 7 (2) to obtain a crude product. Recrystallization from ethyl acetate/ether gives the objective compound (IIa-17) (yield, 99%).

M.p.=254°–256° C. (dcomp.). $^1$HNMR (DMSO) δ: 5.97 (d, J=14.8 Hz, 1H); 6.97–7.22 (m, 3H); 7.43–7.95 (m, 10H); 8.24 (s, 1H); 9.97–10.13 (m, 1H); 12.13–12.45 (m, 1H). IR (Nujol): 3250, 1680, 1614. Elementary analysis (%) for $C_{21}H_{17}NO_4S \cdot 0.25H_2O$. Calc.: C,65.70; H,4.59; N,3.65; S,8.35. Found: C,65.77; H,4.70; N,3.65; S,8.26.

(3) Compound (IIa-17) is reacted in a manner analogous to that set forth in Example 3 (3) (a) to obtain a crude crystalline product. Recrystallization from ethyl acetate/ether gives the objective compound (I-20) (yield, 46%).

M.p.=197°–199° C. (dcomp.). $^1$HNMR (DMSO) δ: 5.92–6.04 (m, 1H); 6.94–7.13 (m, 3H); 7.42–7.92 (m, 10H); 8.24 (s, 1H); 9.00 (s, 1H); 9.97–10.10 (m, 1H); 10.75 (s, 1H). IR (Nujol): 3300, 3140, 1639, 1592. Elementary analysis (%) for $C_{21}H_{18}N_2O_4S \cdot 0.4H_2O$. Calc.: C,62.80; H,4.72; N,6.97; S,7.98. Found: C,62.85; H,4.78; N,6.99; S,7.71.

EXAMPLE 16

(2E)(4Z)-5-[3'-(N-Methylphenylsulfonylamino)-2'-naphthyl]-pentadieno-hydroxamic Acid (I-21)

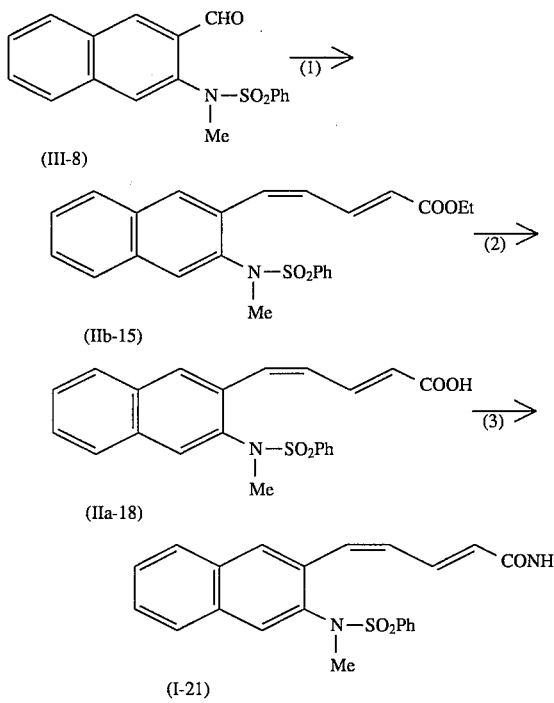

(1) Compound (III-8) is subjected to the Wittig reaction in a manner similar to that set forth in Example 3 (1). The resultant product, when purified by Lobar column chromatography, gives the objective compound (IIb-15) as a foam (yield, 92%).

$^1$HNMR (CDCl$_3$) δ: 1.27 (t, J=7.0 Hz, 3H); 3.21 (s, 3H); 4.18 (q, J=7.0 Hz, 2H); 6.10 (d, J=15.6 Hz, 1H); 6.52 (t, J=11.8 Hz); 7.12–7.22 (m, 2H); 7.48–7.92 (m, 11H). IR (Nujol): 1707, 1630, 1620, 1350. Elementary analysis (%) for C$_{24}$H$_{23}$NO$_4$S. Calc.: C,68.39; H,5.50; N,3.32 S,7.61. Found: C,68.26; H,5.57; N,3.40; S,7.37.

(2) Compound (IIb-15) is hydrolyzed with potassium hydroxide in a manner analogous to that set forth in Example 7 (2) to obtain a crude product. The crude product is purified by column chromatography on silica gel and washed with ether to give the objective compound (IIa-18) as a foam (yield, 57%).

$^1$HNMR (CDCl$_3$) δ: 3.21 (s, 3H); 6.83 (d, J=15.8 Hz, 1H); 6.54 (t, J=11.6 Hz, 1H); 7.11–7.22(m, 2H); 7.43–7.90 (m, 11H). IR (Nujol): 1684, 1618, 1350, 1160. Elementary analysis (%) for C$_{22}$H$_{19}$NO$_4$S•0.3C$_4$H$_{10}$O. Calc.: C,67.03; H,5.33; N,3.37; S,7.71. Found: C,67.23; H,5.29; N,3.46; S,7.59.

(3) Compound (IIa-18) is reacted in a manner analogous to that set forth in Example 3 (3) (a) to obtain a crude product. The crude product is triturated with a mixture of ether and hexane to give the objective compound (I-21) (yield, 91%).

M.p.=107° C. (dcomp.). $^1$HNMR (CDCl$_3$) δ: 3.20 (s, 3H); 5.88–6.04 (m, 1H); 6.36–6.52 (m, 1H); 7.08–7.20 (m, 2H);7.43–7.90 (m, 11H). IR (Nujol): 3330, 3190, 1655, 1616, 1346. Elementary analysis (%) for C$_{22}$H$_{20}$N$_2$O$_4$S•0.25H$_2$O•0.30C$_4$H$_{10}$O. Calc.: C,64.03; H,5.44; N,6.44; S,7.37. Found: C,64.06; H,5.42; N,6.30; S,7.30.

EXAMPLE 17

(2E)(4Z)-5-[2-(N-Methylphenylsulfonylaminomethyl)phenyl]pentadienohydroxamic Acid (I-22)
and
(2E)(4E)-5-[2-(N-methylphenylsulfonylaminomethyl)phenyl]pentadienohydroxamic Acid (I-23)

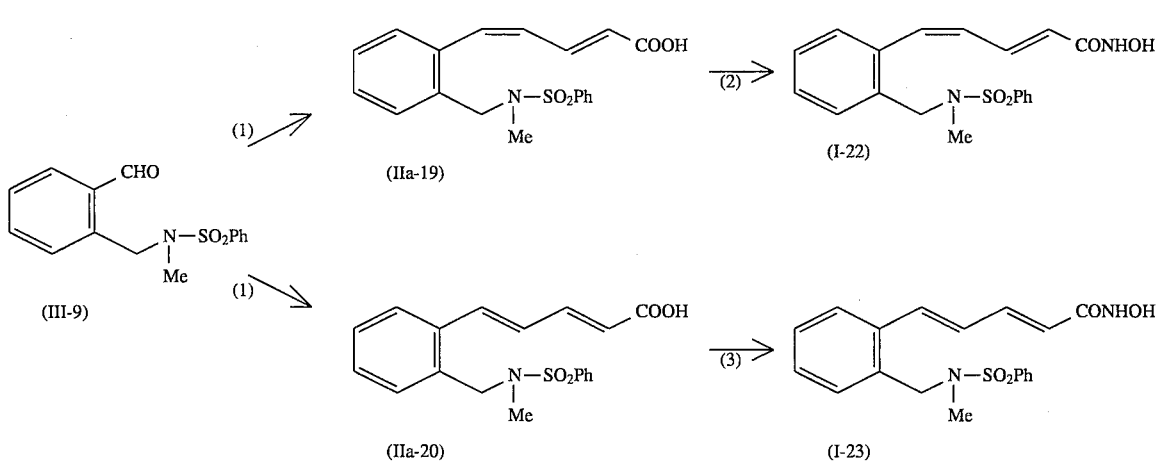

(1) Compound (III-9) is subjected to the Wittig reaction in a manner similar to that set forth in Example 3 (1). The resultant product as a mixture of cis- and trans-isomers is roughly purified by chromatography on silica gel. The resultant mixture is hydrolyzed with potassium hydroxide in a manner similar to that set forth in Example 7 (2) to give a crude product, which is chromatographed on silica gel to remove nonpolar substances. Recrystallization from ethyl acetate/hexane gives trans-isomer (IIa-20) as a crystal, which is easier to crystalize, leaving cis-isomer (IIa-19) in the mother liquid. The mother liquid, when purified by Lobar column, then dissolving in benzene and concentration again, gives the cis-isomer (IIa-19) as a foam.
Compound (IIa-19): yield, 24%.

¹HNMR (CDCl₃) δ: 2.53 (s, 3H); 4.13 (s, 2H); 6.02 (d, J=15,2 Hz, 1H); 6.49 (t, J=11.4 Hz, 1H); 7.15 (d, J=11.4 Hz, 1H); 7.21–7.38 (m, 4H); 7.47–7.68 (m,4H); 7.79–7.89 (m, 2H). IR (KBr): 3410, 1685, 1620. Elementary analysis (%) for C₁₉H₁₉NO₄S·0.4H₂O·0.5C₆H₆. Calc.: C,65.46; H,5.69; N,3.47; S,7.94. Found: C,65.46; H,5.65; N,3.49; S,7.91. Compound (IIa-20): yield, 39%.

M.p.=181°–183° C. ¹HNMR (CDCl₃) δ: 2.55 (s, 3H); 4.22 (s, 2H); 6.02 (d, J=15.2 Hz, 1H); 6.84 (dd, J=15.2 Hz, 11.2 Hz, 1H); 7.22–7.69 (m, 9H); 7.84–7.93 (m, 2H). IR (Nujol): 1680, 1616, 1160, 926. Elementary analysis (%) for C₁₉H₁₉NO₄S. Calc.: C,63.85; H,5.36; N,3.92; S,8.97. Found: C,63.74; H,5.46; N,3.86; S,8.71.

(2) Compound (IIa-19) is reacted in a manner analogous to that set forth in Example 3 (3) (a) to obtain a crude product. The crude product is triturated with ether and hexane to give the objective compound (I-22) (yield, 62%).

M.p.=66° C. (decomp.). ¹HNMR (DMSO) δ: 2.48 (s, 3H); 4.12 (s, 2H); 6.05 (d, J=15.0 Hz, 1H); 6.49 (t, J=11.2 Hz, 1H); 6.98 (d, J=11.2 Hz, 1H); 7.10–7.44 (m,5H); 7.62–7.92 (m, 5H); 8.98 (brs, 1H); 10.77 (brs, 1H). IR (Nujol): 3310, 3190, 1650, 1618, 1160. Elementary analysis (%) for C₁₉H₂₀N₂O₄S·0.2H₂O·0.3C₄H₁₀O. Calc.: C,60.92; H,5.92; N,7.03; S,8.05. Found: C,60.91; H,5.83; N,6.94; S,7.92.

(3) Compound (IIa-20) is reacted in a manner analogous to that set forth in Example 3 (3) (a) to obtain a crude product. The crude product is triturated with ether to give the objective compound (I-23) (yield, 75%) as a powder.

M.p.=82° C. (dcomp.). ¹HNMR (DMSO) δ: 2.46 (s, 3H); 4.23 (s, 2H); 6.05 (d, J=15.2 Hz, 1H); 7.03 (dd, J=15.2 Hz, J=11.2 Hz, 1H); 7.15–7.52 (m, 5H); 7.64–7.96 (m, 6H); 9.00 (brs, 1H); 10.77 (brs, 1H). IR (Nujol): 3320, 3180, 1649, 1613, 1162. Elementary analysis (%) for C₁₉H₂₀N₂O₄S·0.75H₂O·0.25C₄H₁₀O. Calc.: C,59.39; H,5.98; N,6.93; S,7.93. Found: C,59.58; H,5.71; N,6.89; S,7.69.

EXAMPLE 18

(2E)-3-[3-(Phenylsulfonylamino)phenyl]propenohydroxamic Acid (I-24)

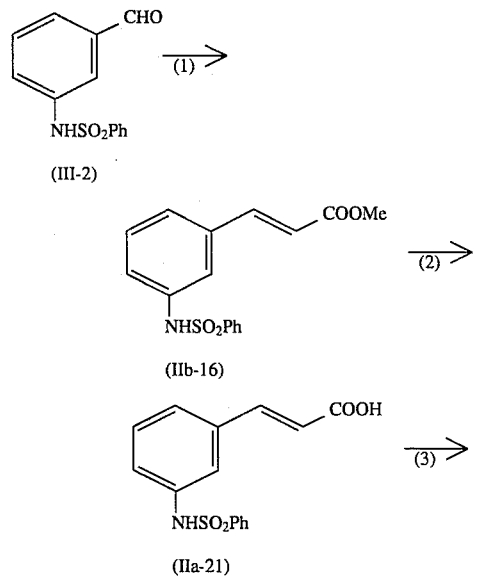

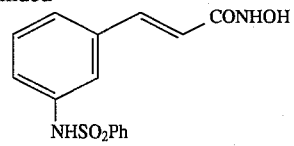

1) Compound (III-2) is subjected to the Wittig reaction in a manner similar to that set forth in Example 11 (1) to obtain a crude product. Recrystallization from ethyl acetate/ether/hexane gives the objective compound (IIb-16) (yield, 91%).

M.p.=144°–146° C. ¹HNMR (CDCl₃) δ: 3.81 (s, 3H); 6.37 (d, J=16.0 Hz, 1H); 6.85 (s, 1H); 7.08–7.30 (m, 4H); 7.40–7.58 (m, 3H); 7.58 (d, J=16.0 Hz, 1H); 7.75–7.83 (m, 2H). IR (Nujol): 3230, 1698, 1637, 1607, 1588. Elementary analysis (%) for C₁₆H₁₅NO₄S. Calc.: C,60.55; H,4.76; N,4.41; S,10.10. Found: C,60.48; H,4.87; N,4.39; S,10.00.

(2) Compound (IIb-16) is hydrolyzed with potassium hydroxide in a manner analogous to that set forth in Example 7 (2) to obtain a crude product. The crude product is recrystallized from ethyl acetate/ether/methylene chloride to give the objective compound (IIa-21) (yield, 100%).

M.p.=178°–179° C. ¹HNMR (DMSO) δ: 6.35 (d, J=16.0 Hz, 1H); 7.08–7.16 (m, 1H); 7.24–7.68 (m, 7H); 7.75–7.84 (m, 2H); 10.45 (brs, 1H); 12.48 (brs, 1H). IR (Nujol): 3270, 1675, 1628. Elementary analysis (%) for C₁₅H₁₃NO₄S·0.1H₂O·0.2C₄H₁₀O. Calc.: C,59.31; H,4.79; N,4.38; S,10.02. Found: C,59.24; H,4.70; N,4.33; S,9.92.

(3) Compound (IIa-21) is reacted in a manner analogous to that set forth in Example 3 (3) (a) to obtain a crude product. The crude product is recrystallized from ethyl acetate/methylene chloride to give the objective compound (I-24) (yield, 80%).

M.p.=85°–88° C. ¹HNMR (DMSO) δ: 6.36 (d, J=15.6 Hz, 1H); 7.02–7.11 (m, 1H); 7.07–7.40 (m, 4H); 7.50–7.70 (m, 3H); 7.76–7.83 (m, 2H); 9.09 (s, 1H); 10.46 (s, 1H); 10.83 (s, 1H). IR (Nujol): 3335, 3130, 1655, 1627, 1604, 1509. Elementary analysis (%) for C₁₅H₁₄N₂O₄S·0.4H₂O. Calc.: C,55.34; H,4.58; N,8.61; S,9.85. Found: C,55.42; H,4.41; N,8.48; S,9.78.

EXAMPLE 19

(2E)-5-[2-(N-Methylphenylsulfonylamino)phenyl]pent-2-en-4-ynohydroxamic Acid (I-25)

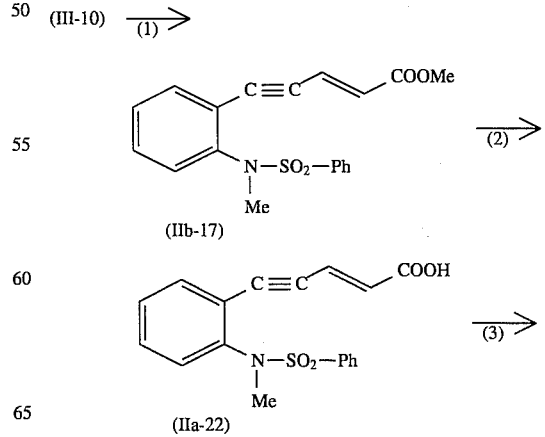

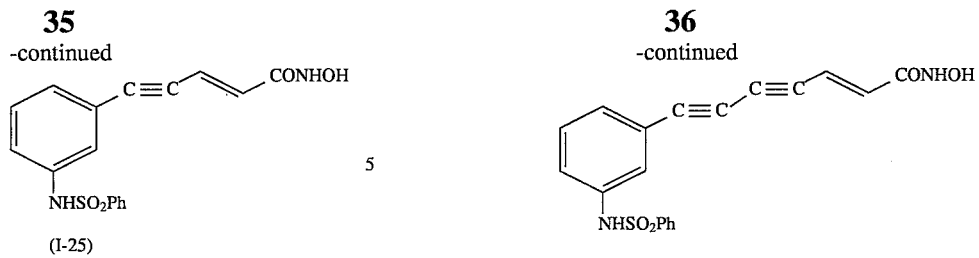

(I-25)

(1) Compound (III-10) is reacted in a manner similar to that set forth in Example 11 (1) to obtain the compound (IIb-17) (yield, 61%).

M.p.=67°–69° C. $^1$HNMR (CDCl$_3$) δ: 3.29 (s, 3H); 3.79 (s, 3H); 6.06 (d, J=15.9 Hz, 1H); 6.68 (d, J=15.9 Hz, 1H); 7.26–7.63 (m, 7H); 7.70–7.82 (m, 2H). IR (KBr): 3070, 2950, 2195, 1718, 1705, 1620. Elementary analysis (%) for C$_{19}$H$_{17}$NO$_4$S. Calc.: C,64.21; H,4.82; N,3.94; S,9.02. Found: C,64.20; H,4.79; N,4.05; S,8.98.

(2) Compound (IIb-17) is reacted in a manner analogous to that set forth in Example 7 (2) to obtain the compound (IIa-22) (yield, 77%).

M.p.=157°–158° C. $^1$HNMR (DMSO) δ: 3.21 (s, 3H); 6.13 (d, J=16.0 Hz, 1H); 6.67 (d, J=16.0 Hz, 1H); 7.17–7.26 (m, 1H); 7.36–7.76 (m, 6H); 12.80 (brs, 1H). IR (KBr): 3680–2220, 2200, 1690, 1612, 1592. Elementary analysis (%) for C$_{18}$H$_{15}$NO$_4$S. Calc.: C,63.33; H,4.33; N,4.10; S,9.39. Found: C,63.14; H,4.55; N,4.38; S,9.21.

(3) Compound (IIa-22) is reacted in a manner analogous to that set forth in Example 3 (3) (a) to obtain the objective compound (I-25) as a foam (yield, 90%). $^1$HNMR (DMSO) δ: 3.22 (s, 3H); 6.20 (d, J=15.6 Hz, 1H); 6.53 (d, J=15.6 Hz, 1H); 7.15–7.25 (m, 1H); 7.34–7.76 (m, 6H); 9.04–9.48 (brm, 1H); 10.90 (brs, 1H). IR (KBr): 3700–2000, 2100, 1650, 1612.

EXAMPLE 20

(2E)-7-[3-(Phenylsulfonylamino)phenyl]hept-2-en-4,6-diynohydroxamic Acid (I-26).

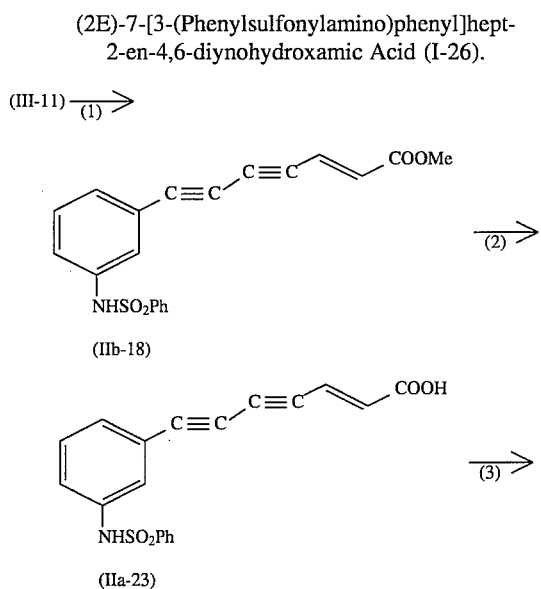

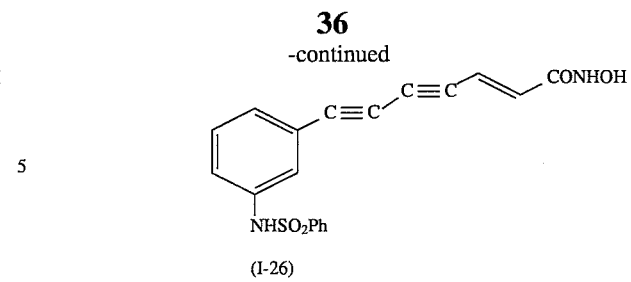

(I-26)

(1) Compound (III-11) is reacted in a manner similar to that set forth in Example 11 (1) to obtain the objective compound (IIb-18).

M.p.=136°–144° C. $^1$HNMR (CDCl$_3$) δ: 3.79 (s, 3H); 6.37 (d, J=15.7 Hz, 1H); 6.84 (d, J=15.7 Hz, 1H); 7.03(brs, 1H); 7.08–7.30 (m, 4H); 7.40–7.65 (m, 3H); 7.72–7.85 (m, 2H). IR (KBr): 3220, 3060, 2940, 2210, 1725, 1718, 1611, 1600, 1577. Elementary analysis (%) for C$_{20}$H$_{15}$NO$_4$S•0.1H$_2$O. Calc.: C,65.42; H,4.17; N,3.81. Found: C,65.29; H,4.19; N,3.92.

(2) Compound (IIb-18) is reacted in a manner analogous to that set forth in Example 7 (2) to obtain the objective compound (IIa-23) (yield, 85%).

M.p.=189°–195° C. $^1$HNMR (CD$_3$OD): 6.38 (d, J=16.0 Hz, 1H); 6.84 (d, J=16.0 Hz, 1H); 7.10–7.32 (m, 4H); 7.42–7.65 (m, 3H); 7.71–7.84 (m, 2H). IR (KBr): 3640–2000, 2200, 1681, 1607, 1578.

(3) Compound (IIa-23) is reacted in a manner analogous to that set forth in Example 3 (3) (a) to obtain the objective compound (I-26) (yield, 81%). &&

M.p.=167°–173° C. (decomp.). $^1$HNMR (DMSO) δ: 6.45 (d, J=15.6 Hz, 1H); 6.70 (d, J=15.6 Hz, 1H); 7.10–7.42 (m, 4H); 7.46–7.70 (m, 3H); 7.70–7.88 (m, 2H); 9.15–9.52 (brm, 1H); 10.20–11.20 (brm, 2H). IR (KBr): 3670–2000, 3310, 2210, 1635, 1598, 1575, 1535. Elementary analysis (%) for C$_{19}$H$_{14}$N$_2$O$_4$S•0.65H$_2$O. Calc.: C,60.36; H,4.08; N,7.41; S,8.48. Found: C,60.65; H,3.97; N,7.17; S,8.19.

EXAMPLE 21

(2E)-3-[4,5-Dimethoxy-2-(phenylsulfonylamino)phenyl] propenohydroxamic Acid (I-27) and
(2E)-3-[4,5-dihydroxy-2-(phenylsulfonylamino)phenyl]propenohydroxamic Acid (I-28)

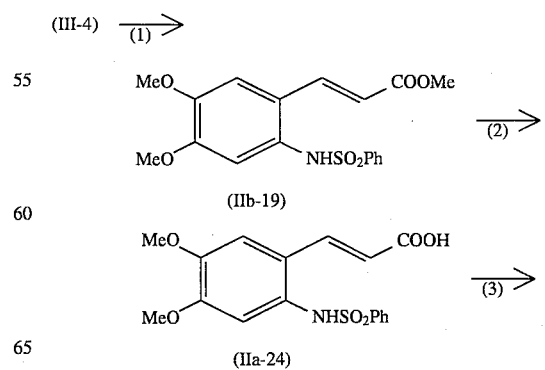

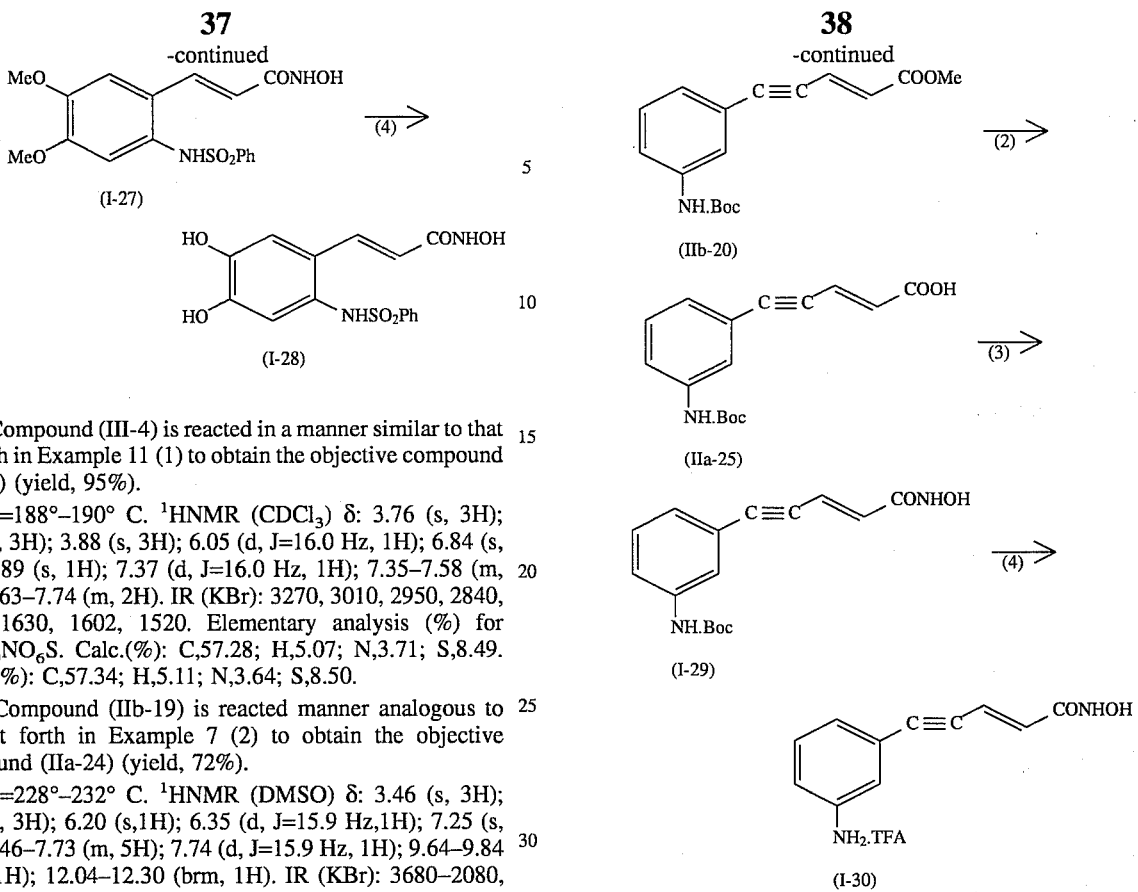

(1) Compound (III-4) is reacted in a manner similar to that set forth in Example 11 (1) to obtain the objective compound (IIb-19) (yield, 95%).

M.p.=188°–190° C. $^1$HNMR (CDCl$_3$) δ: 3.76 (s, 3H); 3.84 (s, 3H); 3.88 (s, 3H); 6.05 (d, J=16.0 Hz, 1H); 6.84 (s, 1H); 6.89 (s, 1H); 7.37 (d, J=16.0 Hz, 1H); 7.35–7.58 (m, 3H); 7.63–7.74 (m, 2H). IR (KBr): 3270, 3010, 2950, 2840, 1705, 1630, 1602, 1520. Elementary analysis (%) for C$_{18}$H$_{19}$NO$_6$S. Calc.(%): C,57.28; H,5.07; N,3.71; S,8.49. Found(%): C,57.34; H,5.11; N,3.64; S,8.50.

(2) Compound (IIb-19) is reacted manner analogous to that set forth in Example 7 (2) to obtain the objective compound (IIa-24) (yield, 72%).

M.p.=228°–232° C. $^1$HNMR (DMSO) δ: 3.46 (s, 3H); 3.79 (s, 3H); 6.20 (s,1H); 6.35 (d, J=15.9 Hz,1H); 7.25 (s, 1H); 7.46–7.73 (m, 5H); 7.74 (d, J=15.9 Hz, 1H); 9.64–9.84 (brm, 1H); 12.04–12.30 (brm, 1H). IR (KBr): 3680–2080, 3290, 2960, 1678, 1622, 1601, 1517. Elementary analysis (%) for C$_{17}$H$_{17}$NO$_6$S. Calc.(%): C,56.19; H,4.72; N,3.85; S,8.82. Found(%): C,55.93; H,4.78; N,3.81; S,8.63.

(3) Compound (IIa-24) is reacted in a manner analogous to that set forth in Example 3 (3) (a) to obtain the objective compound (I-27) (yield, 22%).

M.p.=183°–186° C. $^1$HNMR (DMSO) δ: 3.44 (s, 3H); 3.77 (s, 3H); 6.18 (s, 1H); 6.23 (d, J=16.0 Hz, 1H); 7.05 (s, 1H); 7.45–7.75 (m, 6H); 8.97 (brs, 1H); 9.75 (brs, 1H); 10.57 (brs, 1H). IR (KBr): 3700–2000, 3280, 3010, 1650, 1600, 1570, 1518. Mass analysis: LSIMS m/z=379 [M+H], 757 [2M+H]. HSIMS: for C$_{17}$H$_{19}$N$_2$O$_6$S. Calc.: 379.0962. Found: 379.0950.

(4) Compound (I-27) is reacted in a manner analogous to that set forth in Example 10 (4) to obtain the objective compound (I-29) (yield, 43%).

$^1$HNMR (DMSO) δ: 5.96 (d, J=15.6 Hz, 1H); 6.24 (s, 1H); 6.89 (s, 1H); 7.24–7.67 (m, 6H); 8.91 (brs, 1H); 9.25 (brs, 1H); 9.48 (brs, 1H); 9.58 (brs, 1H); 10.56 (brs, 1H). IR (KBr): 3680–2000, 1652, 1610, 1518. Mass analysis: LSIMS m/z=351 [M+H], 373 [M+Na], 701 [2M+H], 723 [2M+Na]. HSIMS: for C$_{15}$H$_{15}$N$_2$O$_6$S. Calc.: 351.0649. Found: 351.0641.

EXAMPLE 22

(2E)-5-[3-(t-Butoxycarbonylamino)phenyl)pent-2-en-4-ynohydroxamic Acid (I-29) and (2E)-5-(3-aminophenyl)pent-en-4-ynohydroxamic Acid Trifluoroacetate (I-30)

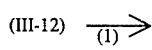

(1) Compound (III-12) is reacted in a manner similar to that set forth in Example 11 (1) to obtain the objective compound (IIb-20) (yield, 74%).

M.p.=111°–112° C. $^1$HNMR (CDCl$_3$) δ: 1.52 (s, 9H); 3.79 (s, 3H); 6.30 (d, J=15.8 Hz, 1H); 6.51 (brs, 1H); 6.97 (d, J=15.8 Hz, 1H); 7.15 (dt, J=7.0, 1.6 Hz, 1H); 7.20 (m, 2H); 7.56–7.63 (brm, 1H). $^{13}$CNMR (CDCl$_3$) δ: 28.31; 51.89, ;80.93; 86.25; 98.25; 119.44; 121.58; 122.84; 125.36; 126.56; 129.08; 129.64; 138.60; 152.56; 166.40. IR (Nujol): 3355, 2195, 1725, 1702, 1619, 1601, 1538. Elementary analysis (%) for C$_{17}$H$_{19}$NO$_4$. Calc.(%): C,67.76; H,6.36; N,4.65. Found(%): C,67.67; H,6.39; N,4.72.

(2) Compound (IIb-20) is hydrolyzed in a manner analogous to that set forth in Example 7 (2) to obtain the objective compound (IIa-25) (yield, 98%).

M.p.=180°–181° C. $^1$HNMR (CDCl$_3$) δ: 1.53 (s, 9H); 6.31 (d, J=15.8 Hz, 1H); 6.63 (brs, 1H); 7.06 (d, J=15.8 Hz, 1H); 7.16 (dt, J=6.8, 1.6 Hz, 1H); 7.21–7.38 (m, 2H); 7.54–7.63 (brm, 1H). IR (Nujol): 3340, 2200, 1720, 1698, 1618, 1582, 1541. Elementary analysis (%) for C$_{16}$H$_{17}$NO$_4$. Calc.(%): C,66.89; H,5.96; N,4.88. Found(%): C,66.92; H,6.08; N,4.87.

(3) Compound (IIa-25) is reacted in a manner analogous to that set forth in Example 3 (3) (a) to obtain the objective compound (I-29) (yield, 78%).

M.p.=157° C. (decomp.). $^1$HNMR (DMSO) δ: 1.48 (s, 1H); 6.34 (d, J=15.8 Hz, 1H); 6.76 (d, J=15.8 Hz, 1H); 7.05–7.16 (brm, 1H); 7.30 (t, J=7.8 Hz, 1H); 7.41–7.53 (brm, 1H); 7.65 (brs, 1H); 9.21 (brs, 1H); 9.52 (brs, 1H); 10.88 (brs, 1H). IR (Nujol): $3340, 3220, 3060, 2200, 1718, 1698, 1630, 1585, 1542. Elementary analysis (%) for C$_{16}$H$_{18}$N$_2$O$_4$. Calc.(%): C,63.56; H,6.00; N,9.27. Found(%): C,63.49; H,6.15; N,9.18.

(4) Compound (I-29) (120 mg, 400 μmol) is suspended in 2 ml of methylene chloride in an atmosphere of nitrogen and 153 μl (2 mmol) of trifluoroacetic acid is added to the suspension at room temperature. After stirring for 2.5 hr at room temperature, the reaction mixture is concentrated under reduced pressure to remove completely the solvent and the excess of trifluoroacetic acid. The residue is crystallized from ether and the crystalline products are washed with water to give 106 mg (335 μM; yield, 84%) of the objective compound (I-30).

M.p.=127° C. (decomp.). $^1$HNMR (DMSO) δ: 6.31 (d, J=15.6 Hz, 1H); 6.74 (d, J=15.6 Hz, 1H); 6.80–6.96 (m, 3H); 7.11–7.25 (m, 1H). IR (Nujol): 3395, 2200, 1681, 1647, 1621, 1202, 1129 cm$^{-1}$. Elementary analysis (%) for $C_{13}H_{11}N_2O_4F_3$. Calc.(%): C,49.38; H,3.51; N,8.86. Found(%): C,49.47; H,3.97; N,8.73.

EXAMPLE 23

(2E)-5-[3-(4-Nitrophenylsulfonylamino)phenyl]pent-2-en-4-ynohydroxamic Acid (I-31)

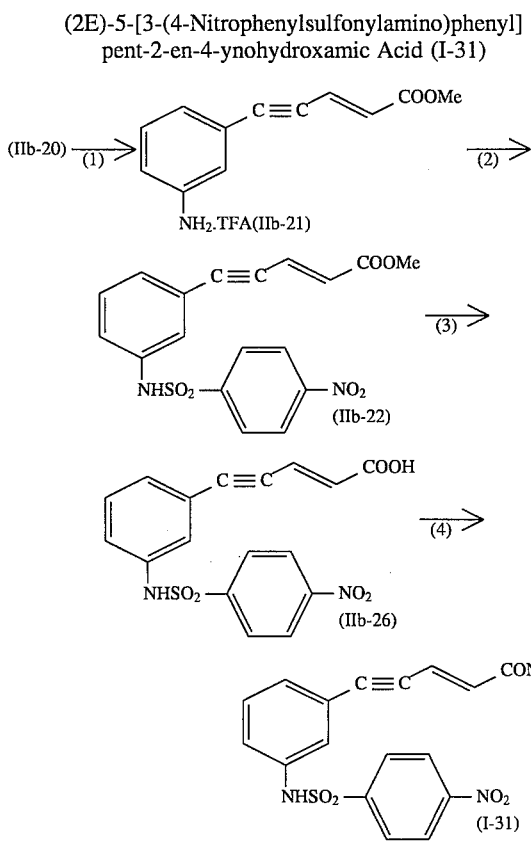

(1) Compound (IIb-20) is reacted in a manner similar to that set forth in Example 22 (4) to obtain the objective compound (IIb-21) (yield, 97%).

M.p.=114° C. (decomp.). $^1$HNMR (CD$_3$OD) δ: 3.77 (s, 3H); 6.37 (d, J=15.8 Hz, 1H); 6.99 (d, J=15.8 Hz, 1H); 7.23 (dt, J=7.4, 1.9 Hz, 1H); 7.28–7.49 (m, 3H). IR (Nujol): 2620, 2195, 1721, 1670, 1617, 1596, 1518 cm$^{-1}$. Elementary analysis (%) for $C_{14}H_{12}NO_4F_3 \cdot 0.1H_2O$. Calc.(%): C,53.04; H,3.88; N,4.42; F,17.98. Found(%): C,53.01; H,3.92; N,4.48; F,17.98.

(2) To a 5.0 ml solution of 0.200 g (0.634 mmol) of compound (IIb-21) in dioxane are added 4.04 ml (2.53 mmol) of 0.627 mol/l NaHCO$_3$ solution and 0.281 g (1.27 mmol) of p-nitrobenzenesulfonyl chloride. After stirring for 60 min at room temperature, the reaction mixture is partitioned between ethyl acetate and 2N HCl. The organic layer is washed with water and a saturated saline, dried, filtered and concentrated. The crude product, when purified by chromatography on silica gel and recrystallized from ether/hexane, gives 0.169 g (0.437 mmol; yield, 69%) of the objective compound (IIb-22).

M.p.=155°–156° C. $^1$HNMR (CDCl$_3$) δ: 3.80 (s, 3H); 6.32 (d, J=15.8 Hz, 1H); 6.80 (brs, 1H); 6.94 (d, J=15.8 Hz, 1H); 7.05–7.18 (m, 1H); 7.18–7.36 (m, 3H); 7.90–8.02 (m, 2H); 8.25–8.68 (m, 2H). IR (KBr): 3680–2000, 3270, 3110, 2950, 2200, 1700, 1619, 1603, 1578, 1532. Elementary analysis (%) for $C_{18}H_{14}N_2O_6S$. Calc.(%): C,55.95; H,3.65; N,7.25; S,8.30. Found(%): C,55.98; H,3.67; N,7.18; S,8.22.

(3) Compound (IIb-22) is hydrolyzed in a manner analogous to that set forth in Example 7 (2) to obtain the objective compound (IIa-26) (yield, 96%).

M.p.=208°–209° C. $^1$HNMR (DMSO) δ: 6.34 (d, J=15.8 Hz, 1H); 6.89 (d, J=15.8 Hz, 1H); 7.12–7.40 (m, 4H); 7.95–8.05 (m, 2H); 8.34–8.45 (m, 2H). IR (KBr): 3680–2000, 3280, 3090, 2195, 1692, 1615, 1578, 1539. Elementary analysis (%) for $C_{17}H_{12}N_2O_6S$. Calc.(%): C,54.84; H,3.25; N,7.52; S,8.61. Found(%): C,54.62; H,3.30; N,7.33; S,8.43.

(4) Compound (IIa-26) is reacted in a manner analogous to that set forth in Example 3 (3) (a) to obtain the objective compound (I-31) (yield, 63%).

$^1$HNMR (DMSO) δ: 6.33 (d, J=15.8 Hz, 1H); 6.73 (d, J=15.8 Hz, 1H); 7.05–7.40 (m, 4H); 7.95–8.05 (m, 2H); 8.33–8.43 (m, 2H); 9.24 (brs, 1H); 10.60–11.05 (brm, 2H). IR (KBr): 3680–2000, 2195, 1645, 1610, 1575, 1528. Elementary analysis (%) for $C_{18}H_{15}N_3O_6S$. Calc.(%): C,53.86; H,3.77; N,10.47; S,7.99. Found(%): C,53.85; H,3.98; N,10.34; S,7.73.

EXAMPLE 24

(2E)-5-[3-(p-Tolylsulfonylamino)phenyl]pent-2-en-4-ynohydroxamic Acid (I-32)

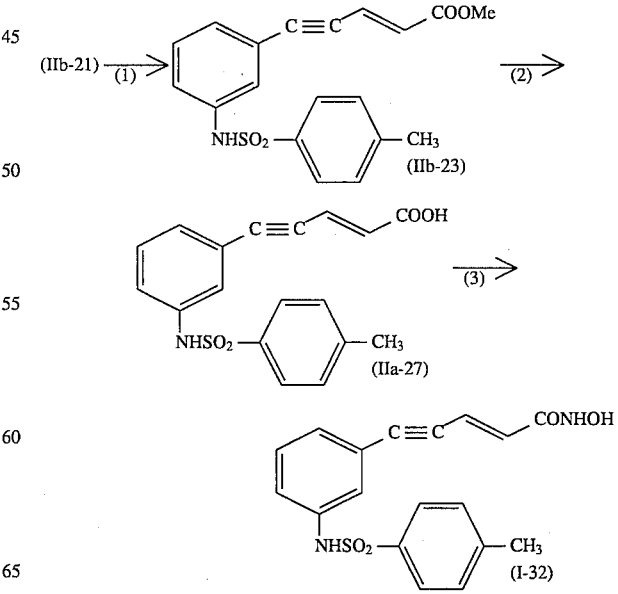

(1) Compound (IIb-21) is reacted in a manner similar to that set forth in Example 23 (2) using p-toluenesulfonyl chloride to obtain the objective compound (IIb-23) (yield, 75%).

M.p.=144°–145° C. $^1$HNMR (CDCl$_3$) δ: 2.39 (s, 3H); 3.79 (s, 3H); 6.31 (d, J=15.8Hz, 1H); 6.74 (brs, 1H ); 6.95 (d, J= 15.8 Hz, 1H); 7.03–7.33 (m, 6H); 7.62–7.72 (m, 2H). IR (KBr): 3630–2000, 3250, 2950, 2200, 1698, 1620, 1598, 1578. Elementary analysis (%) for C$_{19}$H$_{17}$NO$_4$S. Calc.(%): C,64.21; H,4.82; N,3.94; S,9.02. Found(%): C,64.17; H,4.90; N,4.06; S,8.97.

(2) Compound (IIb-23) is hydrolyzed in a manner analogous to that set forth in Example 7 (2) to obtain the objective compound (IIa-27) (yield, 88%).

M.p.=219°–220° C. $^1$HNMR (DMSO) δ: 2.33 (s, 3H); 6.33 (d, J=15.8 Hz, 1H ); 6.89 (d, J=15.8 Hz, 1H); 7.12–7.43 (m, 6H); 7.60–7.72 (m, 2H); 10.44 (brs, 1H). IR (KBr): 3660–2000, 3235, 2190, 1688, 1615, 1578. Elementary analysis (%) for C$_{18}$H$_{15}$NO$_4$S. Calc.(%): C,63.33; H,4.43; N,4.10; S,9.39. Found(%): C,63.08; H,4.65; N,4.04; S,9.17.

(3) Compound (IIa-27) is treated in a manner analogous to that set forth in Example 3 (3) (a) to obtain the objective compound (I-32) (yield, 92%).

$^1$HNMR (DMSO) δ: 2.34 (s, 3H); 6.33 (d, J=15.7 Hz, 1H); 6.73 (d, J=15.7 Hz, 1H); 7.10–7.43 (m, 6H); 7.58–7.70 (m, 2H); 9.23 (brs, 1H); 10.10–11.20 (brm, 1H).

EXAMPLE 25

(2E)-5-[3-(Methylsulfonylamino)phenyl]pent-2-en-4-ynohydroxamic Acid (I-33)

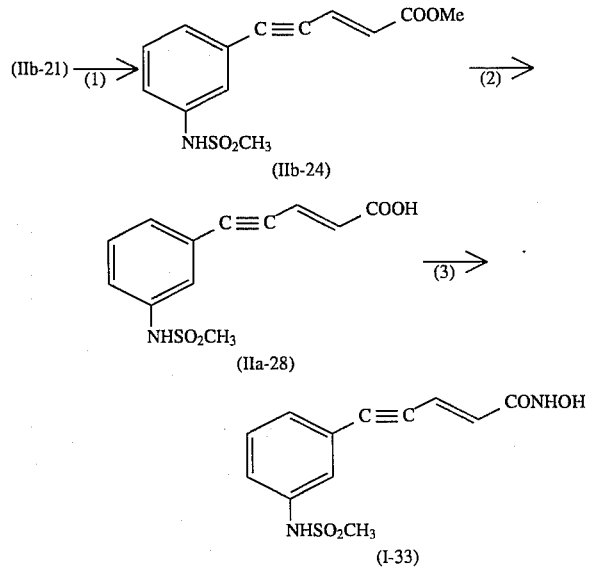

(1) Compound (IIb-21) is reacted in a manner similar to that set forth in Example 23 (2) using methanesulfonyl chloride to obtain the objective compound (IIb-24) (yield, 83%).

M.p.=140°–141° C. $^1$HNMR (CDCl$_3$) δ: 3.05 (s, 3H); 3.80 (s, 3H); 6.34 (d, J=15.8 Hz, 1H); 6.76 (brs, 1H); 6.97 (d, J=15.8 Hz, 1H); 7.20–7.40 (m, 4H). IR (KBr): 3270, 3035, 2199, 1702, 1617, 1578. Elementary analysis (%) for C$_{13}$H$_{13}$NO$_4$S. Calc.(%): C,55.90; H,4.69; N,5.01. Found(%): C,56.14; H,4.82; N,4.84.

(2) Compound (IIb-24) is hydrolyzed in a manner analogous to that set forth in Example 7 (2) to obtain the objective compound (IIa-28) (yield, 88%).

M.p.=236°–238° C. $^1$HNMR (DMSO) δ: 3.03 (s, 3H); 6.36 (d, J=15.8 Hz, 1H); 6.92 (d, J=15.8 Hz, 1H); 7.22–7.47 (m, 4H); 9.96 (brs, 1H). IR (KBr): 3700–2100, 3235, 3010, 2930, 2195, 1708, 1685, 1618, 1575. Elementary analysis (%) for C$_{12}$H$_{11}$NO$_4$S•0.2H$_2$O. Calc.(%): C,53.60; H,4.27; N,5.21. Found(%): C,53.80; H,4.28; N,5.11.

(3) Compound (IIa-28) is treated in a manner analogous to that set forth in Example 3 (3) (a) to obtain the objective compound (I-33) (yield, 75%).

M.p.=147°–153° C (decomp.). $^1$HNMR (DMSO) δ: 3.03 (s, 3H); 6.35 (d, J=15.8 Hz, 1H); 6.76 (d, J=15.8 Hz, 1H); 7.20–7.46 (m, 4H); 9.04–9.46 (brm, 1H); 9.68–11.20 (brm, 1H). Elementary analysis (%) for C$_{12}$H$_{12}$N$_2$O$_4$S. Calc.(%): C,51.42; H,4.31; N,9.99; S,11.44. Found(%): C,51.21; H,4.41; N,9.76; S,11.14.

EXAMPLE 26

(2E)-5-[3-(Hexylsulfonylamino)phenyl]pent-2-en-4-ynohydroxamic Acid (I-34)

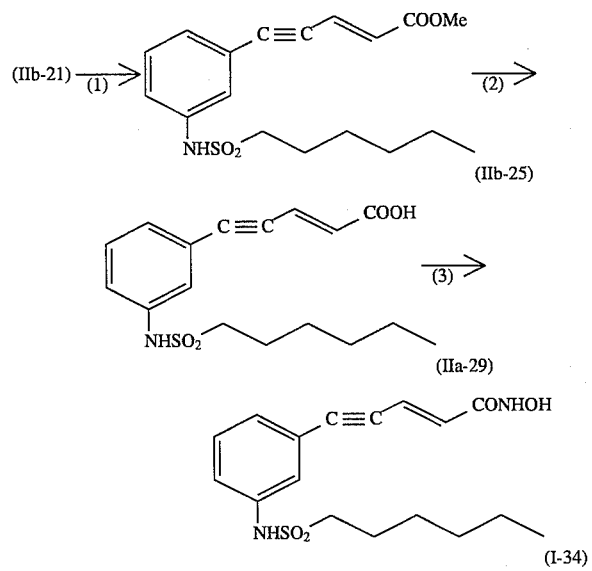

(1) Compound (IIb-21) is reacted in a manner similar to that set forth in Example 23 (2) using 1-hexanesulfonyl chloride to obtain the objective compound (IIb-25) (yield, 37%).

M.p.=91°–92° C. $^1$HNMR (CDCl$_3$) δ: 0.86 (t, J=6.4 Hz, 3H); 1.14–1.48 (m, 6H); 1.70–1.93 (m, 2H); 3.04–3.16 (m, 2H); 3.80 (s, 3H); 6.33 (d, J=15.9 Hz, 1H); 6.67 brs,1H); 6.97 (d, J=15.9 Hz, 1H); 7.17–7.42 (m,4H). IR (KBr): 3230, 2955, 2925, 2860, 2200, 1721, 1714, 1621, 1578. Elementary analysis (%) for C$_{18}$H$_{23}$NO$_4$S. Calc.(%): C,61.87; H,6.63; N,4.01; S,9.17. Found(%): C,61.65; H,6.55; N,4.05; S,9.05.

(2) Compound (IIb-25) is hydrolyzed in a manner analogous to that set forth in Example 7 (2) to obtain the objective compound (IIa-29) (yield, 99%).

M.p.=195°–198° C. $^1$HNMR (DMSO) δ: 0.82 (t, J=6.5 Hz, 3H); 1.07–1.43 (m, 6H); 1.52–1.75 (m, 2H); 3.04–3.17 (m, 2H); 6.35 (d, J=15.8 Hz, 1H); 6.92 (d, J=15.8 Hz, 1H); 7.20–7.47 (m, 4H); 9.99 (brs, 1H). IR (KBr): 3700–2000, 3240, 2955, 2920, 2860, 2190, 1708, 1685, 1616, 1575. Elementary analysis (%) for $C_{17}H_{21}NO_4S$. Calc.(%): C,60.88; H,6.31; N,4.18; S,9.56. Found(%): C,60.90; H,6.25; N,4.26; S,9.37.

(3) Compound (IIa-29) is treated in a manner analogous to that set forth in Example 3 (3) (a) to obtain the objective compound (I-34) (yield, 88%).

M.p.=146°–147° C. (decomp.). $^1$HNMR (DMSO) δ: 0.82 (t, J=6.7 Hz, 3H); 1.07–1.43 (m, 6H); 1.52–1.75 (m, 2H); 3.00–3.20 (m, 2H); 6.35 (d, J=15.8 Hz, 1H); 6.76 (d, J=15.8 Hz, 1H); 7.15–7.47 (m, 4H); 9.23 (brs, 1H); 9.99 (brs, 1H); 10.89(brs, 1H). IR (KBr): 3680–2200, 3300, 3235, 2920, 2850, 2190, 1649, 1612, 1577. Elementary analysis (%) for $C_{17}H_{22}N_2O_4S$. Calc.(%): C,58.27; H,6.33; N,7.99; S,9.15. Found(%): C,58.14; H,6.43; N,7.97; S,9.00.

EXAMPLE 27

(2E)-5-[3-(p-Bromophenylsulfonylamino)phenyl]pent-2-en-4-ynohydroxamic Acid (I-35)

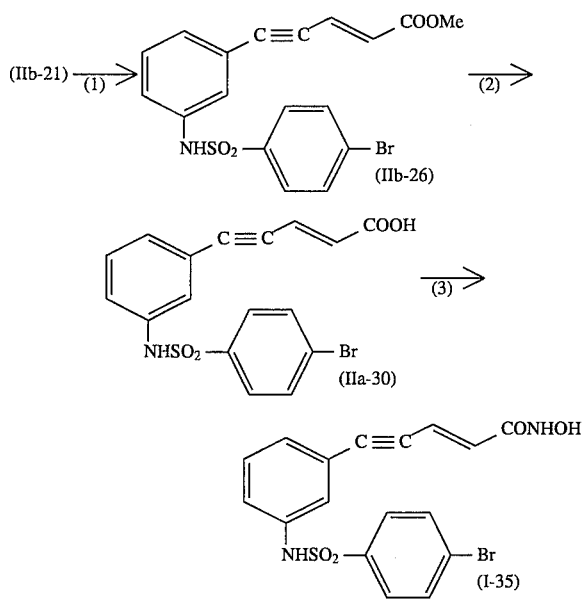

(1) To a 4 ml solution of 200 mg (634 μmol) of compound (IIb-21) in methylene chloride are added 352 μl (634 μmol× 4.0) of triethylamine and 162 mg (634 μmol) of p-bromobenzenesulfonyl chloride at 0° C. in an atmosphere of nitrogen and the mixture is stirred overnight at room temperature. The reaction mixture is partitioned between ethyl acetate and 2N HCl. The organic layer is washed with water, dried, filtered and concentrated to obtain a crude product. Purification by Lobar column chromatography and recrystallization from ether/hexane gives 68 mg (162 μmol; yield, 25%) of the objective compound (IIb-26).

M.p.=146°–147° C. $^1$HNMR (CDCl$_3$) δ: 3.79 (s, 3H); 6.32 (d, J=15.8 Hz, 1H); 6.78 (s, 1H); 6.95 (d, J=15.8 Hz, 1H); 7.03–7.15 (m, 1H); 7.19–7.30 (m, 3H); 7.55–7.69 (m, 4H). IR (Nujol): 3250, 2200, 1697, 1623, 1208, 1160, 953, 601, 551 cm$^{-1}$. Elementary analysis (%) for $C_{18}H_{14}NO_4SBr$. Calc.(%): C,51.44; H,3.36; N,3.33. Found(%): C,51.16; H,3.54; N,3.33.

(2) Compound (IIb-26) is hydrolyzed in a manner analogous to that set forth in Example 7 (2) to obtain the objective compound (IIa-30) (yield, 88%).

M.p.=214°–216° C. $^1$HNMR (CD$_3$OD) δ: 6.29 (d, J=15.8 Hz, 1H); 6.94 (d, J=15.8 Hz,1 H); 7.09–7.32 (m, 4H); 7.66 (brs, 4H). IR (Nujol): 3250, 2190, 1709, 1681, 1614, 1575 cm$^{-1}$.

(3) Compound (IIa-30) is treated in a manner analogous to that set forth in Example 3 (3) (a) to obtain the objective compound (I-35) (yield, 91%).

M.p.=86°–89° C. $^1$HNMR (CD$_3$OD) δ: 6.30 (d, J=15.6 Hz, 1H); 6.85 (d, J=15.6 Hz, 1H); 7.07–7.30 (m, 4H); 7.66 (brs, 4H). IR (Nujol): 3240, 2200, 1645, 1614, 1574, 1155 cm$^{-1}$.

EXAMPLE 28

(2E)-5-[3-(4-Methoxyphenylsulfonylamino)phenyl]pent-2-en-4-ynohydroxamic Acid (I-36)

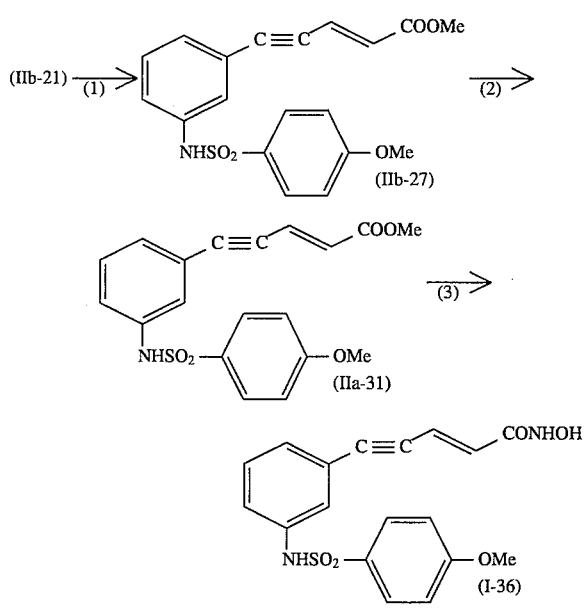

(1) Compound (IIb-21) is treated in a manner similar to that set forth in Example 23 (2) using p-methoxybenzenesulfonyl chloride to obtain the objective compound (IIb-27) (yield, 78%).

M.p.=122°–124° C. $^1$HNMR (CD$_3$OD) δ: 3.79 (s, 3H); 3.83 (s, 3H); 6.31 (d, J=16.0 Hz, 1H); 6.78 (s, 1H); 6.88–7.00 (m, 3H); 7.06–7.15 (m, 1H); 7.18–7.28 (m, 3H); 7.68–7.77 (m, 2H). IR (Nujol): 3260, 2200, 1697, 1622, 1597, 1579, 1497, 1265, 1155 cm$^{-1}$. Elementary analysis (%) for $C_{19}H_{17}NO_5S$. Calc.(%): C,61.44; H,4.61; N,3.77; S,8.63. Found(%): C,61.47; H,4.69; N,3.71; S,8.60.

(2) Compound (IIb-27) is hydrolyzed in a manner analogous to that set forth in Example 7 (2) to obtain the objective compound (IIa-31) (yield, 92%).

M.p.=208°–210° C. $^1$HNMR (CD$_3$OD) δ: 3.82 (s, 3H); 6.28 (d, J=15.8 Hz, 1H); 6.90–7.04 (m, 3H); 7.09–7.30 (m, 4H); 7.65–7.74 (m, 2H). IR (Nujol): 3240, 2190, 1690, 1613, 1596, 1580, 1155 cm$^{-1}$. Elementary analysis (%) for $C_{18}H_{15}NO_5S$. Calc.(%): C,60.50; H,4.23; N,3.92; S,8.97. Found(%): C,60.34; H,4.41; N,3.95; S,8.98.

(3) Compound (IIa-31) is reacted in a manner analogous to that set forth in Example 3 (3) (a) to obtain the objective compound (I-36) (yield, 81%).

M.p.=151° C. (decomp.). ¹HNMR (DMSO) δ: 3.80 (s, 3H); 6.33 (d, J=15.8 Hz, 1H); 6.73 (d, J=15.8 Hz, 1H); 7.02–7.36 (m, 6H); 7.66–7.75 (m, 2H); 9.22 (brs, 1H); 10.40 (brs, 1H); 10.82 (brs, 1H). IR (Nujol): 3330, 3280, 3170, 2200, 1650, 1617, 1597, 1581, 1499, 1145, 1127 cm⁻¹. Elementary analysis (%) for $C_{18}H_{16}N_2O_5S \cdot 0.2H_2O$. Calc.(%): C,57.50; H,4.40; N,7.45; S,8.53. Found(%): C,57.50; H,4.62; N,7.37; S,8.33.

EXAMPLE 29

(2E)-5-[3-(2-Naphthylsulfonylamino)phenyl]pent-2-en-4-ynohydroxamic Acid (I-37)

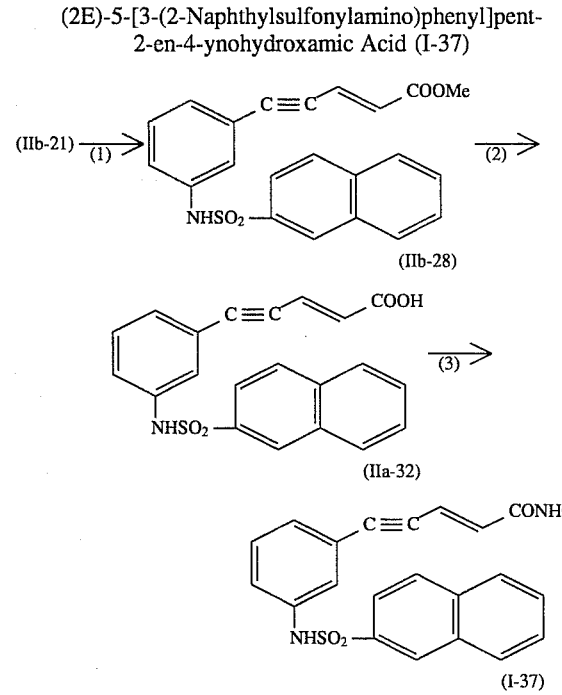

(1) Compound (IIb-21) is reacted in a manner similar to that set forth in Example 23 (2) using 2-naphthylsulfonyl chloride to obtain the objective compound (IIb-28) (yield, 58%).

M.p.=156°–158° C. ¹HNMR (CDCl₃) δ: 3.78 (s, 3H); 6.28 (d, J=15.8 Hz, 1H); 6.92 (d, J=15.8 Hz, 1H); 6.98 (s, 1H); 7.09–7.18 (m, 4H); 7.54–7.95 (m, 6H); 8.39 (d, J=1.8 Hz, 1H). IR (Nujol): 3240, 2200, 1695, 1617, 1157 cm⁻¹. Elementary analysis (%) for $C_{22}H_{17}NO_4S$. Calc.(%): C,67.50; H,4.38; N,3.58; S,8.19. Found(%): C,67.27; H,4.57; N,3.53; S,8.14.

(2) Compound (IIb-28) is hydrolyzed in a manner analogous to that set forth in Example 7 (2) to obtain the objective compound (IIa-32) (yield, 89%).

M.p.=204°–207° C. ¹HNMR (CD₃OD) δ: 6.25 (d, J=15.8 Hz, 1H); 6.91 (d, J=15.8 Hz, 1H); 7.10–7.28 (m, 4H); 7.53–7.79 (m, 3H); 7.88–8.02 (m, 3H); 8.35 (d, J=1.6 Hz, 1H). IR (Nujol): 3250, 2200, 1688, 1617, 1583, 1157 cm⁻¹. Elementary analysis (%) for $C_{21}H_{15}NO_4S \cdot 0.2H_2O$. Calc. (%): C,66.20; H,4.07; N,3.68; S,8.41. Found(%): C,66.51; H,4.40; N,3.58; S,8.49.

(3) Compound (IIa-32) is reacted in a manner analogous to that set forth in Example 3 (3) (a) to obtain the objective compound (I-37) (yield, 78%).

M.p.=91°–93° C. ¹HNMR (DMSO) δ: 6.32 (d, J=15.8 Hz, 1H); 6.72 (d, J=15.8 Hz, 1H); 7.08–7.34 (m, 4H); 7.58–7.86 (m, 3H); 7.86–8.22 (m, 3H); 8.47 (s, 1H); 9.14 (brs, 1H); 10.79 (brs, 2H). IR (Nujol): 3240, 2200, 1648, 1614, 1578, 1155, 1131 cm⁻¹. Elementary analysis (%) for $C_{21}H_{16}N_2O_4S \cdot 0.5H_2O$. Calc. (%): C,62.83; H,4.27; N,6.98; S,7.99. Found(%): C,63.03; H,4.61; N,6.58; S,7.68.

EXAMPLE 30

(2E)-5-[3-(4-Fluorophenylsulfonylamino)phenyl]pent-2-en-4-ynohydroxamic Acid (I-38)

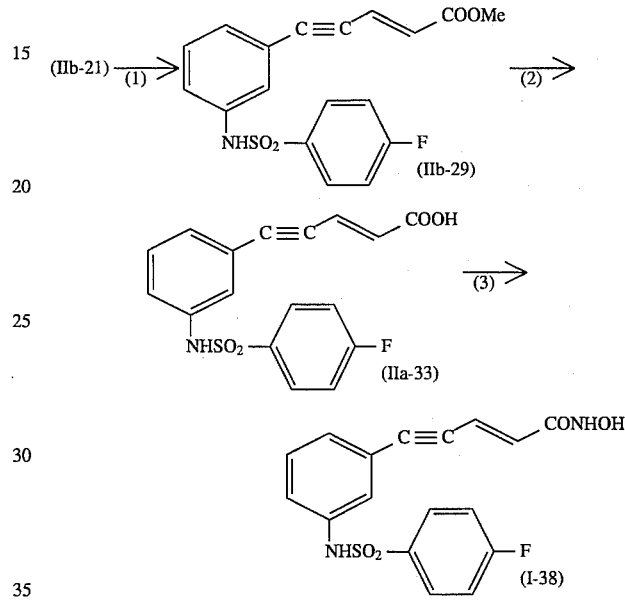

(1) Compound (IIb-21) is reacted in a manner similar to that set forth in Example 23 (2) using p-fluorobenzenesulfonyl chloride to obtain the objective compound (IIb-29) (yield, 81%).

M.p.=147°–149° C. ¹HNMR (CDCl₃) δ: 3.79 (s, 3H); 6.31 (d, J=15.8 Hz, 1H); 6.80 (s, 1H); 6.95 (d, J=15.8 Hz, 1H); 7.07–7.19 (m, 6H); 7.72–7.84 (m, 2H). IR (Nujol): 3310, 3220, 2190, 1717, 1710, 1694, 1617, 1588, 1174, 1167, 1155 cm⁻¹. Elementary analysis (%) for $C_{18}H_{14}NO_4SF$. Calc.(%): C,60.16; H,3.93; N,3.90; S,8.92; F,5.29. Found(%): C,60.17; H,4.01; N,3.85; S,9.21; F,5.31.

(2) Compound (IIb-29) is hydrolyzed in a manner analogous to that set forth in Example 7 (2) to obtain the objective compound (IIa-33) (yield, 97%).

M.p.=185°–186° C. ¹HNMR (CD₃OD) δ: 6.28 (d, J=15.8 Hz, 1H); 6.93 (d, J=15.8 Hz, 1H); 7.10–7.32 (m, 6H); 7.75–7.88 (m, 2H). IR (Nujol): 3250, 2190, 1708, 1680, 1614, 1599, 1165, 1148 cm⁻¹. Elementary analysis (%) for $C_{17}H_{12}NO_4SF$. Calc.(%): C,59.13; H,3.50; N,4.06; S,9.28; F,5.50. Found(%): C,59.11; H,3.63; N,3.97; S,9.39; F,5.46.

(3) Compound (IIa-33) is reacted in a manner analogous to that set forth in Example 3 (3) (a) to obtain the objective compound (I-38) (yield, 96%).

M.p.=74° C. (decomp.). ¹HNMR (DMSO) δ: 6.33 (d, J=15.6 Hz, 1H); 6.74 (d, J=15.6 Hz, 1H); 7.09–7.52 (m, 6H); 7.76–7.92 (m, 2H); 9.24 (brs, 1H); 10.60 (brs, 1H); 10.84 (brs, 1H). IR (Nujol): 3240, 2200, 1647, 1614, 1592, 1163, 1152, 1090 cm⁻¹.

EXAMPLE 31

(2E)-5-(3-Benzoylaminophenyl)pent-2-en-4-ynohydroxamic Acid (I-39)

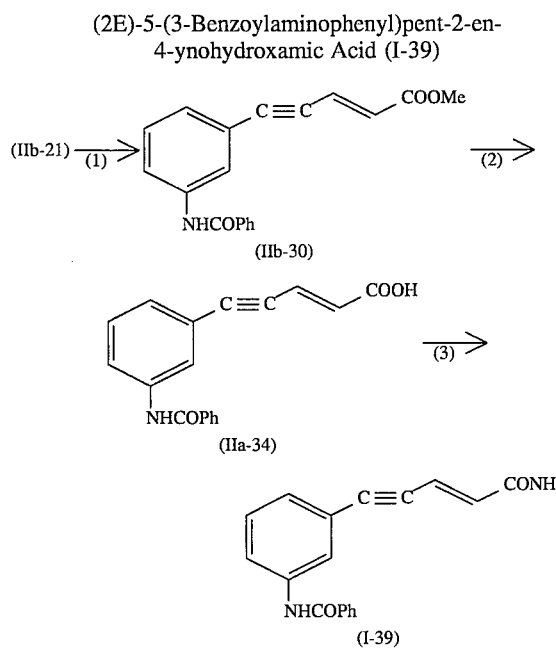

(1) Compound (IIb-21) is reacted in a manner similar to that set forth in Example 23 (2) using benzoylchloride to obtain the objective compound (IIb-30) (yield, 95%).

M.p.=144°–146° C. $^1$HNMR (CDCl$_3$) δ: 3.79 (s, 3H); 6.31 (d, J=15.8 Hz, 1H); 6.98 (d, J=15.8 Hz, 1H ); 7.23–7.71 (m, 6H); 7.80–7.93 (m, 4H). IR (Nujol): 3240, 2200, 1711, 1653, 1619, 1580, 1537, 1175 cm$^{-1}$. Elementary analysis (%) for C$_{19}$H$_{15}$NO$_3$. Calc.(%): C,74.74; H,4.95; N,4.59. Found(%): C,74.62; H,4.98; N,4.55.

(2) Compound (IIb-30) is hydrolyzed in a manner analogous to that set forth in Example 7 (2) to obtain the objective compound (IIa-34) (yield, 96%).

M.p.=232°–234° C. $^1$HNMR (DMSO) δ: 6.36 (d, J=15.8 Hz, 1H); 6.94 (J=15.8 Hz, 1H); 7.24–7.68 (m, 5H); 7.78–8.07 (m, 4H); 10.39 (s, 1H). IR (Nujol): 3305, 2190, 1680, 1652, 1612, 1600, 1578, 1530, 1205 cm$^{-1}$. Elementary analysis (%) for C$_{18}$H$_{13}$NO$_3$·0.2H$_2$O. Calc.(%): C,73.31; H,4.58; N,4.75. Found(%): C,73.49; H,4.60; N,4.79.

(3) Compound (IIa-34) is treated in a manner analogous to that set forth in Example 3 (3) (a) to obtain the objective compound (I-39) (yield, 23%).

M.p.=142° C. (decomp.). $^1$HNMR (CD$_3$OD) δ: 6.33 (d, J=15.4 Hz, 1H); 6.89 (d, J=15.4 Hz, 1H); 7.22–7.76 (m, 6H); 7.88–7.98 (m, 3H). IR (Nujol): 3275, 2195, 1648, 1618, 1580, 1538 cm$^{-1}$.

EXAMPLE 32

(2E)-5-(3-Benzyloxycarbonylaminophenyl)pent-2-en-4-ynohydroxamic Acid (I-40)

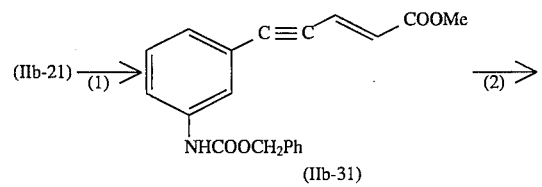

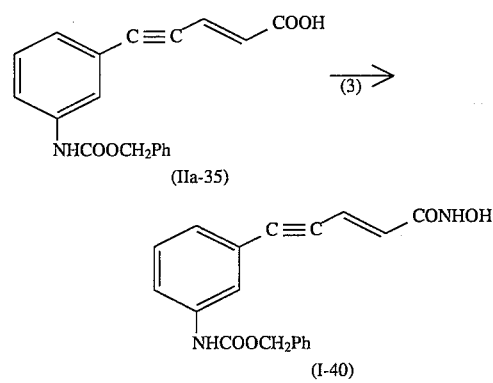

(1) A mixture of 51 mg (250 μmol) of the compound (IIb-21), 80 mg (1 mmol) of dimethylaminopyridine and 1 ml (7.5 mmol) of benzyloxycarbonyl chloride is stirred for 30 min under ice-cooling. The reaction mixture is partitioned between ethyl acetate and water. The organic layer is washed with water and concentrated. The residue, when purified by chromatography on silica gel, gives 71 mg (212 μmol; yield, 84%) of the objective compound (IIb-31).

$^1$HNMR (CDCl$_3$) δ: 3.78 (s, 3H); 5.21 (s, 2H); 6.31 (d, J=16 Hz, 1H); 6.96 (d, J=16 Hz, 1H); 7.18–7.57 (m, 9H).

(2) Compound (IIb-31) is hydrolyzed in a manner analogous to that set forth in Example 7 (2) to obtain the objective compound (IIa-35) (yield, 96%).

M.p.=190.0°–190.5° C. $^1$HNMR (CDCl$_3$) δ: 5.22 (s, 2H); 6.32 (d, J=16 Hz, 1H); 7.05 (d, J=16 Hz, 1H); 7.20–7.58 (m, 9H). Elementary analysis (%) for C$_{19}$H$_{15}$NO$_4$·0.1H$_2$O. Calc.(%): C,71.02; H,4.71; N,4.36. Found(%): C,70.60; H,4.82; N,4.61.

(3) Compound (IIa-35) is treated in a manner analogous to that set forth in Example 3 (3) (a) to obtain the objective compound (I-40) (yield, 54%).

M.p.=139°–144° C. $^1$HNMR (DMSO) δ: 5.16 (s, 2H); 6.34 (d, J=16 Hz, 1H); 6.74 (d, J=16 Hz, 1H); 7.14–7.64 (m, 9H).

EXAMPLE 33

(2E)-5-[3'-[3''-(3''', 4''''-Dimethoxyphenyl)propenoylamino]phenyl]pent-2-en-4-ynohydroxamic Acid (I-41)

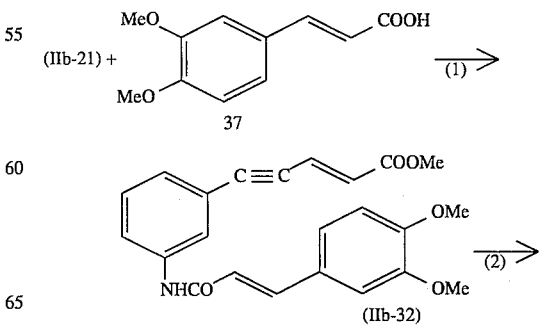

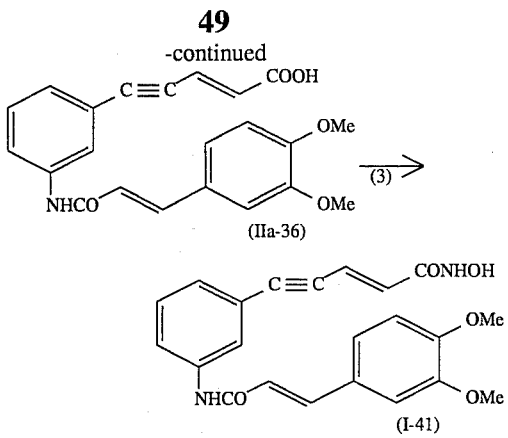

To a 25 ml solution of 1.286 g (6.17 mmol) of compound 37 in methylene chloride is added 1.89 ml (21.6 mmol) of oxalyl chloride. The mixture is stirred for 30 min at room temperature and concentrated under reduced pressure to obtain the acid chloride. In an another vessel, 30 ml of a solution of 0.400 g (1.27 mmol) of compound (IIb-21) in dioxane is prepared. To the solution are added 200 ml of 0.627 mmol/l $NaHCO_3$ solution and 18 ml of the previously prepared solution of the acid chloride in dioxane and the mixture is stirred overnight at room temperature. The reaction mixture is partitioned between ethyl acetate and 2N HCl. The organic layer is washed with water, a 5% $NaHCO_3$ solution, water, and a saline successively, dried and concentrated. The crude product, when purified by chromatography on silica gel and recrystallized from ethyl acetate/ether/hexane, gives 0.3585 g (0.916 mmol; yield, 72%) of the objective compound (IIb-32).

M.p.=127°–129° C. $^1$HNMR ($CDCl_3$) δ: 3.79 (s, 3H); 3.92 (s, 6H); 6.31 (d, J=15.5 Hz, 1H); 6.42 (d, J=15.5 Hz, 1H); 6.82–7.47 (m, 7H); 7.60–7.87 (m, 3H). IR (KBr): 3660–3100, 3370, 3000, 2945, 2840, 2195, 1725, 1672, 1652, 1618, 1595, 1580, 1538, 1512. Elementary analysis (%) for $C_{23}H_{21}NO_5$. Calc.(%): C,70.58; H,5.41; N,3.58. Found(%): C,70.36; H,5.59; N,3.72.

(2) Compound (IIb-32) is hydrolyzed in a manner analogous to that set forth in Example 7 (2) to obtain the objective compound (IIa-36) (yield, 96%).

M.p.=121°–122° C. $^1$HNMR (DMSO) δ: 3.81 (s, 3H); 3.83 (s, 3H); 6.36 (d, J=15.8HZ, 1H); 6.68 (d, J=15.6 Hz, 1H); 6.94 (d, J=15.8 Hz, 1H); 7.02 (d, J=8.4 Hz, 1H); 7.15–7.29 (m, 3H); 7.40 (t, J=8.0 Hz, 1H); 7.55 (d, J=15.6 Hz, 1H); 7.62–7.72 (m, 1H); 7.94 (brs, 1H); 10.28 (brs, 1H). IR (KBr): 3640–2000, 3360, 2960, 2200, 1690, 1660, 1618, 1548, 1512. Elementary analysis (%) for $C_{22}H_{19}NO_5 \cdot 0.2H_2O$. Calc.(%): C,69.36; H,5.13; N,3.68. Found(%): C,69.24; H,5.17; N,3.67.

(3) To a solution of 90 mg (0.229 mmol) of compound (IIa-36) in 20 ml of DMF solution are added 35 μl (0.252 mmol) of triethylamine, 48 mg (0.252 mmol) of WSCD•HCl (1-ethyl-3-(3-dimethylaminopropyl)carbodiimide hydrochloride) and 26.4 mg (0.229 mmol) of HO-Su (N-hydroxysuccinimide) and the mixture is stirred for 1 hr at room temperature. To the reaction mixture are added 224 μl (1.61 mmol) of triethylamine and 80.5 mg (1.16 mmol) of hydroxylamine hydrochloride. After stirring for overnight at room temperature, the reaction mixture is partitioned between ethyl acetate and 2N HCl. The organic layer is washed with water and a saturated saline, dried, filtered and concentrated. Because there still remains about half the amount of the starting materials in the reaction mixture, the same procedures are repeated. Thus, to a solution of the reaction mixture in DMF are added 35 μl (0.251 mmol) of triethylamine, 48.4 mg (0.252 mmol) of WSCD•HCl and 26.9 mg (0.234 mmol) of HO-Su and the mixture is stirred for 1 hr at room temperature. To the reaction mixture are added 224 μl (1.61 mmol) of triethylamine and 80.5 mg (1.17 mmol) of hydroxylamine hydrochloride. After stirring overnight at room temperature, the reaction mixture is partitioned between ethyl acetate and 2N HCl. The organic layer is washed with water and a saturated saline, dried, filtered and concentrated. The residue is washed with water several times to obtain 16.2 mg (0.041 mmol; purity, 84%; yield, about 15%) of the objective compound (I-41).

$^1$HNMR (DMSO) δ: 3.81 (s, 3H); 3.83 (s, 3H); 6.36 (d, J=15.8 Hz, 1H); 6.60–6.87 (m, 2H); 7.02 (d, J=8.4 Hz, 1H); 7.14–7.30 (m, 3H); 7.38 (t, J=7.7 Hz, 1H); 7.45–7.73 (m, 2H); 7.96 (brs, 1H); 9.22 (brs, 1H); 10.26 (brs, 1H); 10.88 (brs,1H). Mass analysis: LSIMS m/z=393 [M+H].

REFERENCE EXAMPLE 1

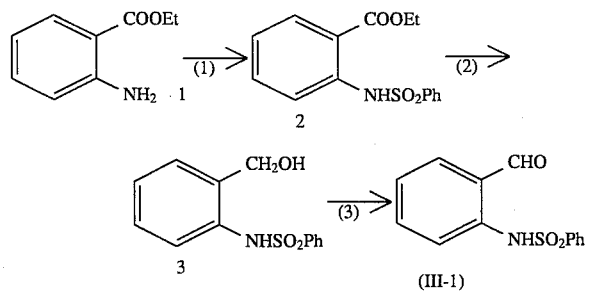

(1) To a solution of 25.20 g (0.153 mol) of the starting compound 1 in 600 ml of dioxane are added 800 ml of 5% $NaHCO_3$ solution and 15 g of $NaHCO_3$ and the mixture is stirred vigorously. An 80 ml solution of 48.7 ml (0.382 mol) of benzenesulfonyl chloride in dioxane is added gradually at room temperature and the resultant mixture is stirred for about 7 hr. The reaction mixture is partitioned between ethyl acetate and 2N HCl. The organic layer is washed with water and a saturated saline, dried over $MgSO_4$ and concentrated to obtain a crude compound 2. Recrystallization from toluene/hexane gives 29.24 g (0.0958 mol; yield, 63%) of the compound 2.

M.p.=90°–92° C. $^1$HNMR ($CDCl_3$) δ: 1.36 (t, J=7.2 Hz, 3H); 4.33 (q, J=7.2 Hz, 2 H); 6.98–7.10 (m, 1H); 7.32–7.58 (m,4H); 7.64–7.74 (m, 1H); 7.77–7.98 (m, 3H); 10.7 (brs, 1H). IR (KBr): 2980, 1678, 1601, 1588. Elementary analysis (%) for $C_{15}H_{15}NO_4S$. Calc.: C,59.00; H,4.95; N,4.59; S,10.50. Found: C,58.88; H,5.00; N,4.58; S,10.20.

(2) To a 300 ml solution of 28.85 g (0.0945 mol) of compound 2 in THF is carefully added 5.32 g (0.140 mmol) of lithium aluminum hydride and the mixture is stirred for about 1 hr at room temperature. To the reaction mixture was added ethyl acetate and water under ice-cooling to decompose the excess of reducing agents. It was then partitioned between ethyl acetate and 2N HCl. The organic layer is washed with water and a saline, dried over $MgSO_4$, filtered and concentrated under reduced pressure to obtain a crude product. Recrystallization from methylene chloride/ether gives 22.34 g (0.0848 mol; yield, 90%) of the compound 3.

M.p.=127°–128° C. $^1$HNMR ($CDCl_3$) δ: 2.05–2.21 (brm, 1H); 4.37 (d, J=5.0 Hz, 2H); 7.03–7.15 (m, 2H); 7.17–7.33(m, 1H); 7.33–7.59 (m, 4H); 7.70–7.81 (m, 2H); 7.94 (brs, 1H). IR (KBr): 3440, 3070, 2805, 1583. Elementary analysis (%) for $C_{13}H_{13}NO_3S$. Calc.: C,59.30; H,4.98; N,5.32; S,12.18. Found: C,59.06; H,4.94; N,5.52; S,11.89.

(3) To a 1500 ml solution of 22.06 g (83.8 mmol) of compound 3 in methylene chloride are added 44 g of molecular sieve 4A (powder) and 32.5 g (151 mmol) of pyridinium chlorochromate and the mixture is stirred for 70 min at room temperature. The reaction mixture is purified by column chromatography on silica gel eluting with methylene chloride to yield 20.46 g (78.3 mmol; yield, 94 of the compound (III-1).

M.p.=120°–122° C. $^1$HNMR (CDCl$_3$) δ: 7.10–7.24 (m, 1H); 7.40–7.65 (m, 5H); 7.71 (d, J=8.4 Hz, 1H); 7.84–7.98 (m, 2H); 9.83 (s, 1H); 10.83 (brs, 1H). IR (KBr): 3130, 2840, 2755, 1678, 1603, 1581. Elementary analysis (%) for $C_{13}H_{12}NO_3S$. Calc.: C,59.76; H,4.24; N,5.36; S,12.27. Found: C,59.59; H,4.30; N,5.34; S,11.99.

REFERENCE EXAMPLE 2

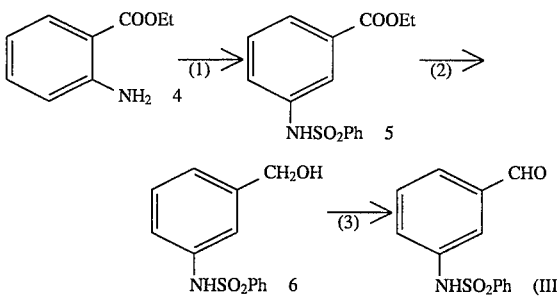

(1) Compound 4 was reacted in a manner analogous to that set forth in Reference Example 1 (1) to give the compound 5 (yield, 90%).

M.p.=75°–78° C. $^1$HNMR (CDCl$_3$) δ: 1.36 (t, J=7.1 Hz, 3H); 4.36 (d, J=7.1 Hz, 2 H); 7.12 (brs, 1H); 7.27–7.62 (m, 5H); 7.66–7.74 (m, 1H); 7.74–7.88 (m, 3H). IR (KBr): 3230, 2980, 1692, 1610, 1590, 1472, 1345, 1295, 1180, 1163, 1092, 759, 718, 685, 582, 553. Elementary analysis (%) for $C_{15}H_{15}NO_4S$. Calc.: C,59.00; H,4.95; N,4.59; S,10.50. Found: C,58.74; H,4.99; N,4.54; S,10.45.

(2) Compound 5 was reacted in a manner analogous to that set forth in Reference Example 1 (2) to give the crude compound 6 (yield, quantitative). The crude product was subjected to the next reaction process without purification.

$^1$HNMR(CDCl$_3$) δ (crude product): 1.90 (brs, 1H); 4.60 (s, 2H); 6.83–7.31 (m, 4H); 7.08 (brs, 1H); 7.35–7.60 (m, 3H); 7.70–7.85 (m, 2H).

(3) Compound 6 was reacted in a manner analogous to that set forth in Reference Example 1 (3) to give the objective compound (III-2) (yield, 83%).

M.p.=104°–105° C. $^1$HNMR (CDCl$_3$) δ: 7.17 (brs, 1H ); 7.26–7.70 (m, 7H); 7.76–7.88(m, 2H); 9.92 (s, 1H). IR (KBr): 3180, 2910, 1678, 1610, 1590, 1448, 1428, 1392, 1346, 1168, 1148, 1091, 728, 685, 588 , 552. Elementary analysis (%) for $C_{13}H_{11}NO_3S$. Calc.: C,59.76; H,4.24; N,5.36; S,12.27. Found: C,59.53; H,4.16; N,5.23; S,12.28.

REFERENCE EXAMPLE 3

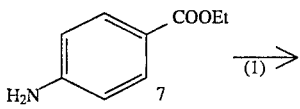

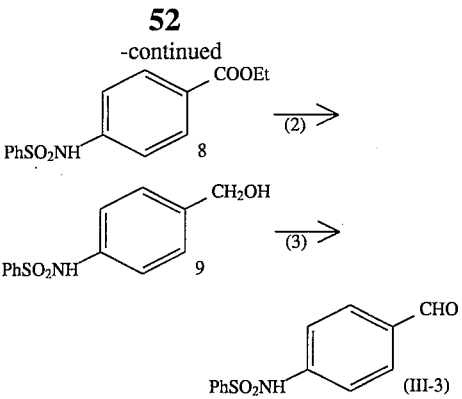

(1) Compound 7 is subjected to the sulfonylation in a manner analogous to that set forth in Reference Example 1 (1) to give the compound 8 (yield, 86%).

M.p.=182°–183° C. $^1$HNMR (CDCl$_3$) δ: 1.36 (t, J=7.2 Hz, 3H); 4.33 (q, J=7.2 Hz, 2H); 7.09–7.19 (m, 2H); 7.23 (brs, 1H); 7.40–7.62 (m, 3H); 7.80–7.98 (m, 4H). IR (KBr): 3235, 2990, 1692, 1610, 1513, 1411, 1343, 1318, 1292, 1158, 1092, 923, 765, 720, 688, 582, 567. Elementary analysis (%) for $C_{15}H_{15}NO_4S$. Calc.: C,59.00; H,4.95; N,4.59; S,10.50. Found: C,59.19; H,5.06; N,4.58; S,10.22.

(2) To a 100 ml suspension of 3.93 g (0.104 mol) of lithium alminium hydride in THF is added dropwise and gradually a 140 ml solution of 15.44 g (0.0506 mol) of compound 8 in THF. After stirring for 40 min at room temperature, the reaction mixture is treated in a manner similar to that set forth in Reference Example 1 (2). Recrystallization from ether/hexane/ethyl acetate gives 13.31 g (0.0506 mol; yield, 100%) of the compound 9.

M.p.=69.5°–71.5° C. $^1$HNMR (CDCl$_3$) δ: 1.78 (brs, 1H); 4.62 (s, 2H); 6.92 (brs, 1H); 7.00–7.12 (m,2H); 7.18–7.30 (m, 2H); 7.35–7.60 (m, 3H); 7.73–7.84 (m, 2H). IR (KBr): 3420, 3150, 2940, 2870, 1613, 1515, 1340, 1312, 1155, 1092, 688, 582. Elementary analysis (%) for $C_{13}H_{13}NO_3S$. Calc.: C,59.30; H,4.98; N,5.32; S,12.18. Found: C,59.41; H,5.05; N,5.48; S,12.07.

(3) Compound 9 is reacted in a manner analogous to that set forth in Reference Example 1 (3) to give the compound (III-3) (yield, 66%).

M.p.=135.5°–137° C. $^1$HNMR (CDCl$_3$) δ: 7.20–7.29 (m, 2H); 7.43–7.64 (m, 4H); 7.72–7.83 (m, 2H); 7.85–7.94 (m, 2H); 9.88 (s, 1H). IR (KBr): 3235, 2845, 1688, 1599, 1582, 1342, 1311, 1290, 1219, 1155, 1088, 910, 829, 721, 682, 628, 582, 563. Elementary analysis (%) for $C_{13}H_{11}NO_3S$. Calc.: C,59.76; H,4.24; N,5.36; S,12.27. Found: C, 60.00; H,4.39; N,5.35; S,12.05.

REFERENCE EXAMPLE 4

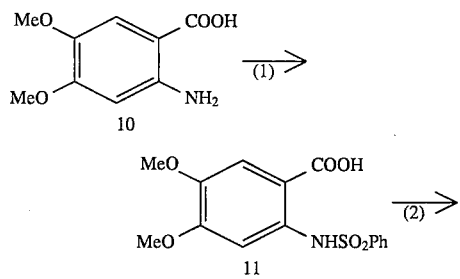

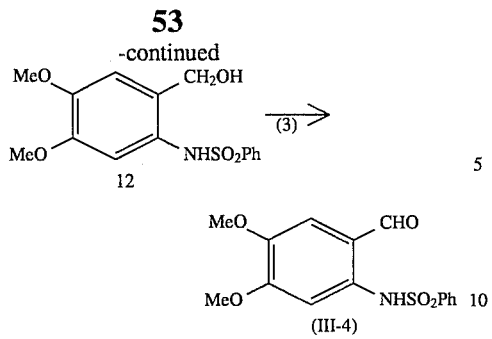

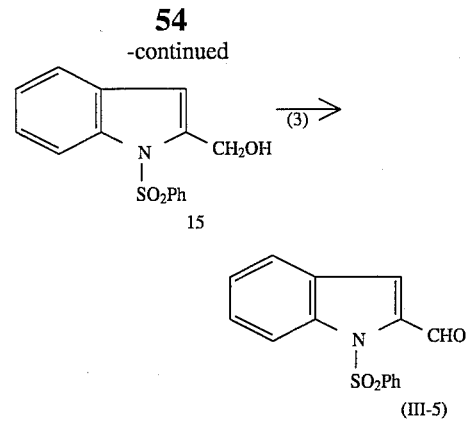

(1) To 19.7 g (0.30 mol) of compound 10 is added a solution of 25.2 g (0.30 mol) of sodium hydrogen carbonate in 300 ml of water and the mixture is stirred for 30 min at room temperature. To the mixture is added 50 ml of dioxane to obtain a complete solution, which was added with a 50 ml solution of 15.3 ml (0.12 mol) of benzenesulfonyl chloride in dioxane. After stirring for 1 hr at room temperature, the mixture is partitioned between ethyl acetate and conc. HCl. The organic layer is washed with water and a saturated saline, dried, filtered and concentrated to obtain 33.6 g (0.099 mol; yield, 100%) of the crude compound 11, which is used in the next reducing reaction without further purification.

(2) To a 300 ml solution of 31.3 g (92.8 mmol) of compound 11 in THF is added 3.53 g (93.0 mmol) of lithium aluminium hydride over a period of more than 1 hr. After stirring for 30 min at room temperature, to the mixture is added 1.77 g (46.6 mmol) of lithium aluminium hydride again. Temperature of reaction mixture is elevated gradually and the reaction is carried out for 30 min at 40° C., for 30 min at 45° C. and for 4 hr at 55° C. After cooling down to 0° C., ethyl acetate and 2N HCl are carefully added to the mixture in this order to decompose the excess of reagents. The organic layer is washed with water (×2) and a saturated saline (×1), dried, filtered and concentrated. The resultant crude crystalline compound 12, when washed 2-3 times with ether, gives 28.0 g (86.6 mmol; yield, 93%) of the compound 12 with relative high purity. The product is used in the next reaction without further purification.

M.p.=112°–114° C. $^1$HNMR (CDCl$_3$) δ (crude crystal): 3.74 (s, 3H); 3.83 (s, 3H);4.26 (s, 2H); 6.66 (s, 1H); 6.74 (s, 1H); 7.34 (brs, 1H); 7.38–7.64 (m, 3H); 7.66–7.80 (m, 2H).

(3) Compound 12 is reacted in a manner analogous to that set forth in Reference Example 1 (3) to give the objective compound (III-4) (yield, 54%).

M.p.=140°–142° C. $^1$HNMR (CDCl$_3$) δ: 3.87 (s, 3H); 3.95 (s, 3H); 1H); 6.94 (s, 1H); 7.32 (s, 1H); 7.37–7.60 (m, 3H); 7.76–7.90 (m, 2H); 9.64 (s, 1H). IR (Nujol): 3130, 1650, 1604, 1580, 1519. Elementary analysis (%) for C$_{15}$H$_{15}$NO$_5$S. Calc.: C,56.06; H,4.71; N,4.36; S,9.98. Found: C,55.93; H,4.72; N,4.39; S,10.02.

REFERENCE EXAMPLE 5

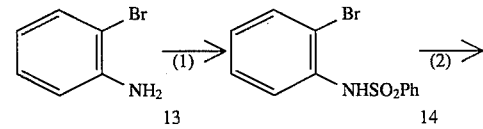

(1) Compound 13 is reacted in a manner analogous to that set forth in Reference Example 1 (1) to give the compound 14 (yield, 48%).

M.p.=129°–131° C. $^1$HNMR (CDCl$_3$) δ: 6.90–7.04 (m, 1H); 6.97 (brs, 1H); 7.23–7.34 (m, 1H); 7.36–7.60 (m, 4H); 7.68 (dd, J=8.2,1.0 Hz, 1H); 7.72–7.82 (m, 2H). IR (KBr): 3260, 3060, 1582, 1472, 1449, 1400, 1334, 1168, 1158, 1091, 902, 758, 723, 688, 588, 550. Elementary analysis (%) for C$_{12}$H$_{10}$NO$_2$S. Calc.: C,46.17; H,3.23; N,4.49; S,10.27; Br, 25.60. Found: C,46.12; H,3.20; N,4.51; S,10.23; Br, 25.72.

(2) To a 300 ml solution of 29.79 g (95.4 mmol) of compound 14 in benzene are added 80 ml of triethylamine, 0.671 g (0.956 mmol) of palladium bistriphenylenephosphine dichloride, 0.091 g (0.478 mmol) of copper iodide and 16.7 ml (287 mmol) of propargyl alcohol and the mixture is heated to reflux overnight. The reaction mixture is concentrated under reduced pressure. The residue is combined with ether and filtered to remove insoluble materials. Purification by chromatography on silica gel gives 5.19 g (18.1 mmol; yield, 19%) of the objective compound 15 as an oil. Although it contains a little solvent, it is used in the next reaction as it is.

$^1$HNMR (CDCl$_3$) δ: 3.11 (t, J=7.3 Hz, 1H); 4.92 (d, J=7.3 Hz, 2H); 6.67 (s, 1H); 7.17–7.63 (m, 6H); 7.77–7.90 (m, 2H); 8.07 (d, J=8.0 Hz, 1H).

(3) Compound 15 is reacted in a manner analogous to that set forth in Reference Example 1 (3) to give the compound (III-5) (yield, 82%).

M.p.=108°–109° C. $^1$HNMR (CDCl$_3$) δ: 7.20–7.70 (m, 7H); 7.70–7.86 (m, 2H); 8.25 (d, J=8.6 Hz, 1H); 10.53 (s,1H). IR (KBr): 3060, 2920, 1668, 1605, 1575, 1525, 1365, 1238, 1180, 1151, 1130, 1089, 1051, 751, 745, 719, 588, 578, 562, 549. Elementary analysis (%) for C$_{15}$H$_{11}$NO$_3$S. Calc.: C,63.15; H,3.89; N,4.91; S,11.24. Found: C,62.95; H,3.94; N,4.93; S,11.09.

REFERENCE EXAMPLE 6

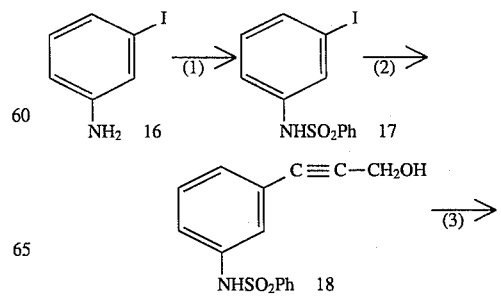

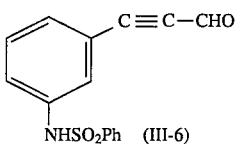

(1) Compound 16 is reacted in a manner analogous to that set forth in Reference Example 1 (1) to give the compound 17 (yield, 83%).

M.p.=101°–102° C. $^1$HNMR (CDCl$_3$) δ: 6.92 (brs, 1H); 6.93–7.14 (m, 2H); 7.35–7.64 (m, 5H); 7.73–7.88 (m, 2H). IR (KBr): 3241, 3280, 1590, 1479, 1395, 1330, 1157, 1091, 928, 778, 721, 685, 550. Elementary analysis (%) for C$_{12}$H$_{10}$NIO$_2$S. Calc.: C,40.13; H,2.81; N,3.90; I,35.33; S,8.93. Found: C,39.93; H,2.88; N,3.94; I,35.46; S,8.71.

(2) Compound 17 is reacted in a manner analogous to that set forth in Reference Example 5 (2) (reaction is carried out for 2 hr by heating to reflux) to obtain the compound 18 (yield, 63%) as an oil. The product, which contains a little solvent, is used in the next reaction as it is.

$^1$HNMR (CDCl$_3$) δ: 1.94–2.03 (m, 1H); 4.47 (d, J=5.8 Hz, 1H); 7.00–7.04 (m, 4H); 7.15 (s, 1H); 7.56–7.60 (m, 3H); 7.72–7.85 (m, 2H).

(3) Compound 18 is subjected to the oxidation in a manner analogous to that set forth in Reference Example 1 (3) to give the objective compound (III-6) (yield, 26%).

M.p.=136°–138° C. $^1$HNMR (CDCl$_3$) δ: 7.10 (brs, 1H); 7.17–7.40 (m, 4H); 7.40–7.65 (m, 3H); 7.75–7.88 (m, 2H); 9.40 (s, 1H). $^{13}$CNMR (CDCl$_3$) δ: 88.45, 93.69, 120.62, 123.95, 125.15, 127.18, 129.31, 129.88, 129.97, 133.45, 137.11, 138.63, 176.71. IR (KBr): 3190, 2180, 1628, 1580, 1504, 1415, 1349, 1172, 1152, 1021, 938, 781, 758, 721, 689, 676, 585, 552. Elementary analysis (%) for C$_{15}$H$_{11}$NO$_3$S•0.1H$_2$O. Calc.: C,62.75; H,3.93; N,4.88; S,11.17. Found: C,62.69; H,3.88; N,4.90; S,11.10.

REFERENCE EXAMPLE 7

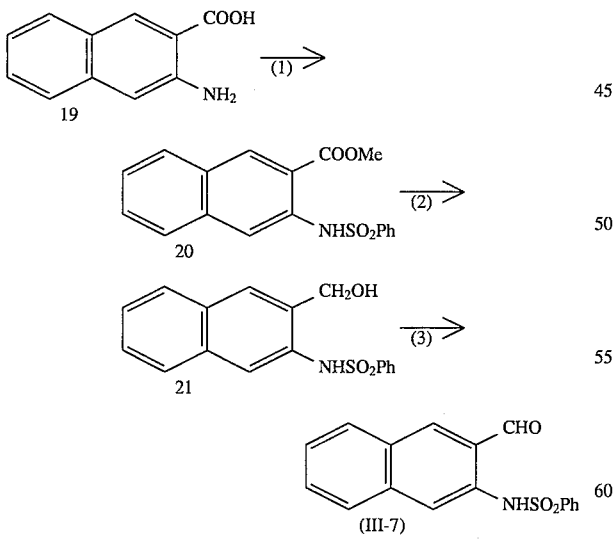

(1) Under an atmosphere of nitrogen, 25.2 g (80% purity, 108 mmol) of 3-amino-2-naphtoic acid is suspended in 250 ml of methanol. The suspension is gently heated to reflux for 7 hr with stirring while dry chlorine gas is being bubbled into it and concentrated. To the residue is added benzene and the resultant solution is concentrated again to yield the hydrochloride of methyl ester, which is suspended in 450 ml of methylene chloride. To the suspension are added 120 ml (108 mmol×8) of triethylamine and 27.6 ml (108 mmol×2) of benzenesulfonyl chloride at 0° C. and the mixture is stirred for 4 hr at room temperature. The reaction mixture is partitioned between ethyl acetate and 2N HCl. The organic layer is washed with water, a saturated saline and 2N HCl and concentrated. Purification by column chromatography on silica gel and recrystallization from methylene chloride/ether give 11.78 g (34.5 mmol; yield, 32%) of the compound 20.

M.p.=170°–172° C. $^1$HNMR (CDCl$_3$) δ: 3.91 (s, 3H); 7.32–7.62 (m, 5H); 7.75–7.90(m, 4H); 8.09 (s, 1H); 8.50 (s, 1H); 10.40 (s, 1H). IR (Nujol): 3130, 1680, 1513. Elementary analysis (%) for C$_{18}$H$_{15}$NO$_4$S. Calc.: C,63.33; H,4.43; N,4.10; S,9.39. Found: C,63.08; H,4.48; N,3.89; S,9.19.

(2) Compound 20 is reduced in a manner analogous to that set forth in Reference Example 1 (2) to obtain a crude product. Recrystallization from ethyl acetate/hexane gives the compound 21 (yield, 85%).

M.p.=145°–146° C. $^1$HNMR (CDCl$_3$) δ: 2.15–2.23 (m, 1H ); 4.49 (d, J=5.2 Hz, 2H ); 7.32–7.57 (m, 6H); 7.68–7.84 (m, 4H); 7.95 (s, 1H); 8.16 (s, 1H). IR (Nujol): 3450, 3075. Elementary analysis (%) for C$_{17}$H$_{15}$NO$_3$S. Calc.: C,65.16; H,4.82; N,4.47; S,10.23. Found: C,65.09; H,4.94; N,4.46; S,10.07.

(3) Compound 21 is oxidized in a manner analogous to that set forth in Reference Example 1 (3) to obtain a crude product. Recrystallization from methylene chloride/hexane gives the objective compound (III-7) (yield, 87%).

M.p.=205°–207° C. $^1$ HNMR (CDCl$_3$) δ: 7.35–7.54 (m, 4H); 7.59–7.69 (m, 1H); 7.77–7.94 (m, 4H); 8.06 (s, 1H) ;8.14 (s, 1H); 9.96 (s, 1H); 10.47 (s, 1H). IR (Nujol): 3175, 1667, 1511, 1409. Elementary analysis (%) for C$_{17}$H$_{13}$NO$_3$S. Calc.: C,65.58; H,4.21; N,4.50; S,10.30. Found: C,65.51; H,4.24; N,4.39; S,10.21.

REFERENCE EXAMPLE 8

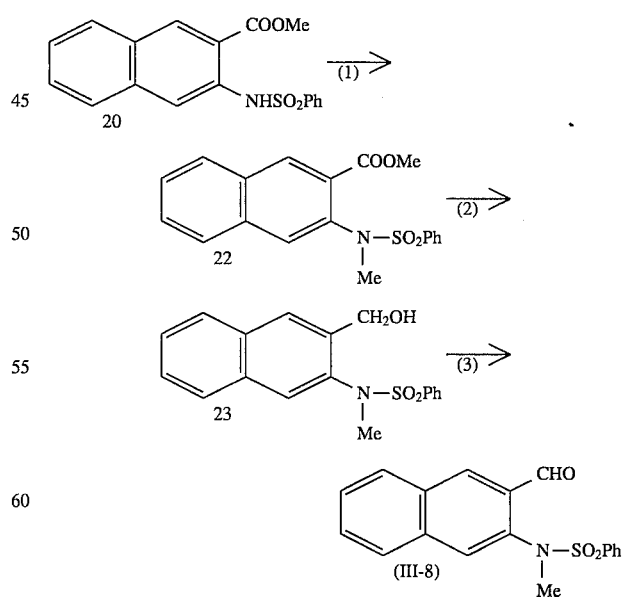

(1) Compound 20 prepared in Reference Example 7 (1) is subjected to N-methylation in a manner analogous to that set forth in Example 14 (1) to give a crude product. Recrystallization from ether/hexane gives the compound 22 (yield, 92%).

M.p.=124°–125° C. $^1$HNMR (CDCl$_3$) δ: 3.38 (s, 3H); 3.90 (s, 3H); 7.34 (s, 1H); 7.42–7.71 (m, 8H); 7.88–7.96 (m, 1H); 8.42 (s, 1H). IR (Nujol): 1715, 1350. Elementary analysis (%) for C$_{19}$H$_{17}$NO$_4$S. Calc.: C,64.21; H,4.82; N,3.94; S,9.02. Found: C,64.10; H,4.86; N,3.87; S,8.85.

(2) Compound 22 is reduced in a manner analogous to that set forth in Reference Example 1 (2) to give a crude product. Recrystallization from ether/hexane gives the compound 23 (yield, 95%).

M.p.=125°–126° C. $^1$HNMR (CDCl$_3$) δ: 3.05 (brs, 1H); 3.27 (s, 3H); 4.88 (brs, 1H); 5.09 (brs, 1H); 6.86 (s, 1H); 7.38–7.62 (m, 5H); 7.65–7.75 (m, 4H); 7.87 (d, J=8.0 Hz, 1H); 8.06 (s, 1H). IR (Nujol): 3540, 1334, 1160. Elementary analysis (%) for C$_{18}$H$_{17}$NO$_3$S. Calc.: C,66.04; H,5.23; N,4.28; S,9.79. Found: C,66.08; H,5.25; N,4.33; S,9.70.

(3) Compound 23 is oxidized in a manner analogous to that set forth in Reference Example 1 (3) to obtain a crude product. Recrystallization from methylene chloride/hexane gives the objective compound (III-8) (yield, 98%).

M.p.=185°–187° C. $^1$HNMR (CDCl$_3$) δ: 3.36 (s, 3H); 7.12 (s, 1H); 7.42–7.70 (m, 8H); 7.98–8.04 (m, 1H); 8.56 (s, 1H); 10.56 (s, 1H). IR (Nujol): 1685, 1626, 1350. Elementary analysis (%) for C$_{18}$H$_{15}$NO$_3$S. Calc.: C,66.44; H,4.65; N,4.30; S,9.85. Found: C,66.24; H,4.60; N,4.39; S,9.81.

REFERENCE EXAMPLE 9

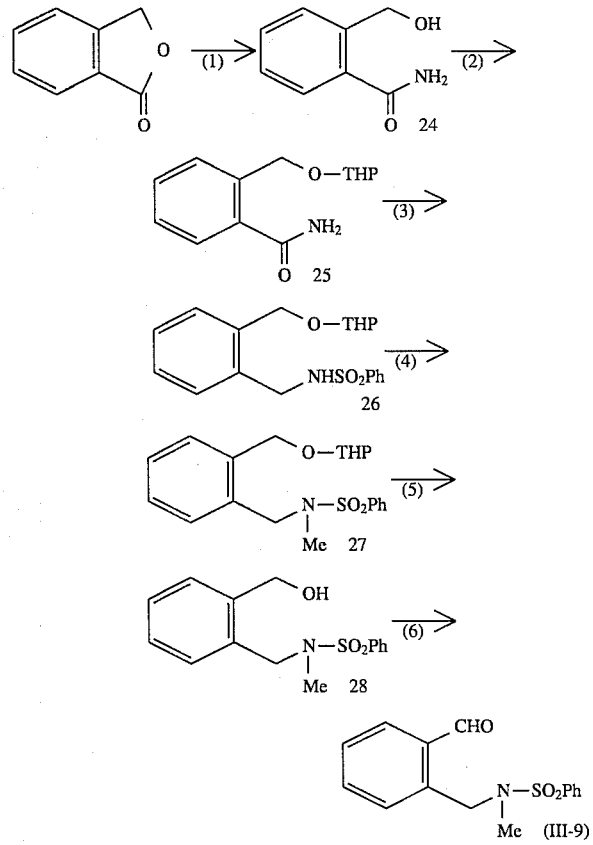

THP: tetrahydrofuran.

(1) Ammonia gas is bubbled into a solution of 10 g (74.6 mmol) of phthalide in 60 cc of methanol and 4 cc of methylene chloride for 30 min. The reaction solution is allowed to stand for 6 days at room temperature and concentrated to yield a crude crystalline product. Recrystallization from methylene chloride gives 2.31 g (15.3 mmol; yield, 20%) of the compound 24.

M.p.=147°–149° C. $^1$HNMR (DMSO) δ: 4.62 (d, J=5.4 Hz, 2H); 5.28 (t, J=5.4 Hz, 1H); 7.25–7.58 (m, 5H); 7.88 (brs, 1H). Elementary analysis (%) for C$_8$H$_9$NO$_2$. Calc.: C,63.56; H,6.00; N,9.27. Found: C,63.26; H,5.99; N,9.22.

(2) To a suspension of 2.10 g (13.9 mmol) of compound 24 in 20 ml of THF and 14 ml of DMF are added 11.25 ml (13.9 mmol×8.9) of 3,4-dihydro-2H-pyrane, which is distilled at room temperature, and 200 mg (13.9 mmol×0.076) of p-toluenesulfonic acid•1 hydrate and the mixture is stirred overnight at room temperature. After the reaction completes, the reaction mixture is partitioned between ethyl acetate and 5% aqueous NaHCO$_3$ solution. The organic layer is washed with water, a saturated saline, dried and concentrated. The residue, when purified by column chromatography on silica gel and recrystallized from ether/hexane, gives 1.49 g (6.3 mmol; yield, 46%) of the compound 25.

M.p.=92°–94° C. IR (Nujol): 3380, 3185, 1647, 1625, 1400, 1388, 1127, 1033. Elementary analysis (%) for C$_{13}$H$_{17}$NO$_3$. Calc.: C,66.36; H,7.28; N,5.95. Found: C,66.33; H,7.28; N,6.08. $^1$HNMR (CDCl$_3$) δ: 1.28–1.87 (m, 6H); 3.49–3.62 (m, 1H); 3.80–3.94 (m, 1H); 4.69 (d, J=11.8 Hz, 1H); 4.75 (brs, 1H); 4.94 (d, J=11.8 Hz, 1H); 5.96 (brs, 1H); 7.27 (brs, 1H); 7.34–7.52 (m, 3H); 7.74–7.83 (m, 1H).

(3) To a solution of 1.45 g (6.16 mmol) of compound 25 in 15 ml of THF is added dropwise a 15 ml suspension of 468 mg (6.16 mmol×2) of lithium aluminium hydride in THF at room temperature and the mixture is stirred for 3 hr at room temperature. To the reaction mixture are added slowly ethyl acetate and water in this order at 0° C. to decompose the excess of reagents, which is followed by the extraction by decantation with ethyl acetate. The organic layer is washed with water and concentrated. The residue is dissolved in 25 ml of methylene chloride. To the solution are added 2.56 ml (6.16 mmol×3) of triethylamine and 789 μl (6.16 mmol) of benzenesulfonyl chloride at 0° C. and the mixture is stirred for 1 hr at 0° C. The reaction mixture is partitioned between ethyl acetate and a chilled dilute aqueous solution of oxalic acid. The organic layer is washed with water, a 5% aqueous NaHCO$_3$ solution, water, a saturated saline successively, dried and concentrated. The residue, when purified by column chromatography on silica gel, gives 1.34 g (3.71 mmol; yield, 60%) of the compound 26 as an oil.

$^1$HNMR (CDCl$_3$) δ: 1.49–1.90 (m, 6H); 3.48–3.60 (m, 1H); 3.80–3.92 (m, 1H); 4.20 (d, J=6.4 Hz, 2H); 4.43 (d, J=11.4 Hz, 1H); 4.58–4.68 (m, 1H); 4.71 (d, J=11.4 Hz, 1H); 5.84 (t, J=6.4 Hz, 1H); 7.09–7.31 (m, 4H); 7.39–7.59 (m, 3H); 7.79–7.90 (m, 2H).

(4) The compound 26 (1.34 g) is subjected to N-methylation in a manner analogous to that set forth in Example 14 (1) to give a crude product. Purification by column chromatography on silica gel gives 1.17 g (3.11 mmol; yield, 84%) of the compound 27 as an oil.

$^1$HNMR (CDCl$_3$) δ: 1.46–1.92 (m, 6H); 2.58 (s, 3H); 3.46–3.57 (m, 1H); 3.78–3.91 (m, 1H); 4.14 (d, J=14.0 Hz, 1H); 4.36 (d, J=14.0 Hz, 1H); 4.58 (d, J=12.0 Hz, 1H); 4.66–4.72 (m, 1H); 4.80 (d, J=12.0 Hz, 1H); 7.24–7.43 (m, 4H); 7.51–7.68 (m, 3H); 7.83–7.91(m, 2H).

(5) To a solution of 0.17 g (3.11 mmol) of compound 27 in 20 ml of THF is added 4 ml of 2N HCl and the mixture is stirred for 24 hr. The reaction mixture is partitioned between ethyl acetate and water. The organic layer is washed with a 5% aqueous NaHCO$_3$ solution, water, a saturated saline, dried and concentrated. Purification by column chromatography on silica gel gives the compound 28 as an oil, which is crystallized from ethyl acetate/hexane to give 693 mg (2.38 mmol; yield, 76%) of the compound 28 as a colorless crystal.

M.p.=79°–80° C. IR (Nujol): 3530, 1165, 1089, 1008, 574. Elementary analysis (%) for $C_{15}H_{17}NO_3S$. Calc.: C,61.83; H,5.88; N,4.81; S,11.00. Found: C,61.65; H,5.87; N,4.80; S,10.75. $^1$HNMR (CDCl$_3$) δ: 2.55 (s, 3H); 4.23 (s, 2H); 4.86 (s, 2H); 7.15–7.48 (m, 4H); 7.55–7.72 (m, 3H); 7.82–7.91 (m, 2H).

(6) Compound 28 is oxidized in a manner analogous to that set forth in Reference Example 1 (3) to obtain a crude product. Recrystallization from ethyl acetate/hexane gives the compound (III-9) (yield, 96%).

M.p.=105°–107° C. $^1$HNMR (CDCl$_3$) δ: 2.70 (s, 3H); 4.70 (s, 2H); 7.48–7.94 (m, H); 10.20 (s, 1H). IR (Nujol): 1685, 1600, 1206, 1168, 1157, 923. Elementary analysis (%) for $C_{15}H_{15}NO_3S$. Calc.: C,62.27; H,5.23; N,4.84; S,11.08. Found: C,62.18; H,5.24; N,4.95; S,11.05.

REFERENCE EXAMPLE 10

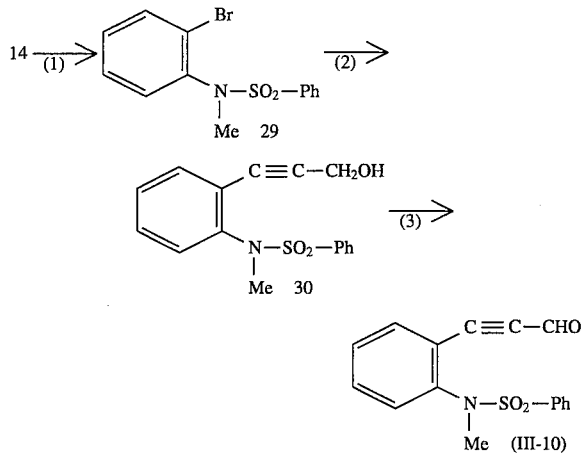

(1) Compound 14 is reacted in a manner analogous to that set forth in Example 14 (1) to give the compound 29 (yield, 70%).

M.p.=74°–75° C. $^1$HNMR (CDCl$_3$) δ: 3.21 (s, 3H); 7.11–7.34 (m, 3H); 7.46–7.67 (m, 4H); 7.76–7.87 (m,2H). IR (KBr): 3060, 2970, 2930, 1581. Elementary analysis (%) for $C_{13}H_{12}BrNO_2S$. Calc.: C,47.87; H,3.71; Br,24.49; N,4.29; S,9.83. Found: C,47.69; H,3.76; Br,24.23; N,4.30; S,9.89.

(2) Compound 29 is reacted in a manner analogous to that set forth in Reference Example 5 (2) to give the crude compound 30 (yield, 63%). The product, though it contained a little amount of solvent, was subjected to the next process as it is.

$^1$HNMR (CDCl$_3$) δ: 3.26 (s, 3H); 4.16–4.29 (brm, 2H); 7.14–7.67 (m, 7H); 7.74–7.83 (m, 2H).

(3) Compound 30 is reacted in a manner analogous to that set forth in Reference Example 1 (3) to give the objective compound (III-10) (yield, 55%).

$^1$HNMR (CDCl$_3$) δ: 3.31 (s, 3H); 7.10–7.66 (m, 7H); 7.68–7.80 (m, 2H); 9.12 (s, 1H). $^{13}$CNMR (CDCl$_3$) δ: 38.57, 90.88, 91.75, 119.74, 127.80, 128.39, 129.15, 130.72, 132.13, 132.95, 135.21, 138.08, 143.98, 175.98.

REFERENCE EXAMPLE 11

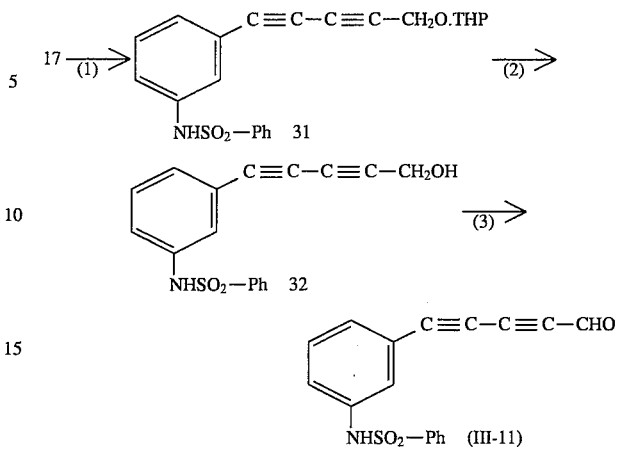

(1) Compound 17 is reacted with tetrahydropyranyloxy-pent-2,4-diyne in a manner analogous to that set forth in Reference Example 5 (2) to give the compound 31 (yield, 18%). The product, which contains a little solvent, is used as it is in the next reaction.

$^1$HNMR (CDCl$_3$) δ: 1.44–1.95 (m, 6H); 3.48–3.63 (m, 1H); 3.76–3.92 (m, H); 4.40 (s, 2H); 4.84 (t, J=3.0 Hz, 1H); 6.95 (brs, 1H); 7.07–7.30 (m, 4H); 7.40–7.63 (m, 3H); 7.75–7.87 (m, 2H).

(2) To a 19 ml solution of 11.67 g (2.95 mmol) of compound 31 in THF is added 4.8 ml of 2N HCl and the mixture is stirred overnight at room temperature. The reaction mixture is partitioned between 5% sodium hydrogen carbonate solution and ethyl acetate. The organic layer is washed with water, a saturated saline, dried over MgSO$_4$ and concentrated. The crude product, when purified by column chromatography and recrystallized from methylene chloride/hexane, gives 0.690 g (2.22 mmol; yield, 75%) of the compound 32 (yield, 75%).

M.p.=116°–117° C. $^1$HNMR (CDCl$_3$) δ: 1.60–2.00 (brm, 1H); 4.42 (s, 2H); 7.00 (brs, 1H); 7.05–7.30 (m, 4H); 7.40–7.63 (m, 3H); 7.72–7.85 (m, 2H). $^3$CNMR (CDCl$_3$) δ: 51.66, 70.16, 73.91, 77.37, 80.98, 122.44, 122.60, 124.98, 127.15, 129.20, 129.54, 129.58, 133.32, 136.59, 138.68. IR (KBr): 3420, 3160, 2950, 2860, 2230, 1600, 1580, 1505. Elementary analysis (%) for $C_{17}H_{13}NO_3S$. Calc.: C,65.58; H,4.21; N,4.50; S,10.30. Found: C,65.42; H,4.23; N,4.32; S,10.10.

(3) Compound 32 is reacted in a manner analogous to that set forth in Reference Example 1 (3) to give the compound (III-11). As the product is labile, it is used without further treatment to the next process (in this case, that is described in Example 20).

REFERENCE EXAMPLE 12

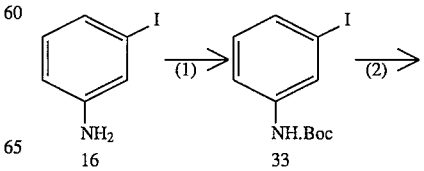

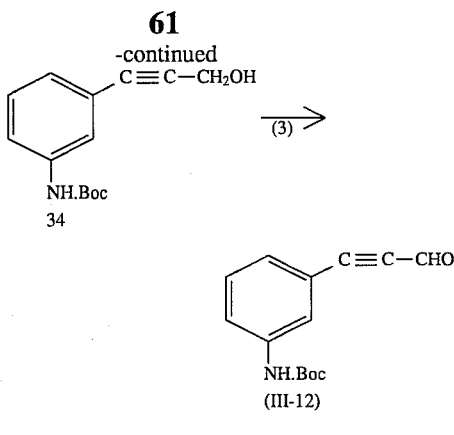

(1) In an atmosphere of nitrogen, to a 300 ml solution of 38.27 g (175 mmol) of m-iodoaniline 16 in methanol is added 47.7 ml (208 mmol) of di-t-butyldicarbonate under ice-cooling. The mixture is stirred overnight at room temperature and the reaction is completed by an additional 4-hour-stirring at 35° C. The reaction mixture is partitioned between ethyl acetate and 2N HCl. The organic layer is washed with water, a 5% aqueous $NaHCO_3$ solution, water, a saturated saline successively, dried, filtered and concentrated. The crude product, when recrystallized from hexane, gives 50.62 g (159 mmol; yield, 92%) of the objective compound 33.

M.p.=73°–74° C. $^1$HNMR ($CDCl_3$) δ: 1.51 (s, 9H); 6.43 (brs, 1H); 6.99 (t, J=8.0 Hz, 1H); 7.21–7.30 (m, 1H); 7.32–7.40 (m, 1H); 7.83 (t, J=2.0 Hz, 1H). IR (Nujol): 3290, 2930, 2850, 1712, 1688, 1595, 1530. Elementary analysis (%) for $C_{11}H_{14}NO_2I$. Calc.(%): C,41.40; H,4.42; N,4.39; I,39.76. Found(%): C,41.35; H,4.43; N,4.57; I,39.76.

(2) Compound 33 is reacted in a manner analogous to that set forth in Reference Example 5 (2) using tetrakistriphenylphosphine palladium as a catalyst to obtain a crude product, which is then roughly purified by column chromatography on silica gel to yield the objective compound 34 containing a small amount of impurity (yield, 52%).

$^1$HNMR ($CDCl_3$) δ: 1.52 (s, 9H); 4.47 (s, 2H); 6.53 (brs, 1H); 7.10 (dt, J=7.4, 1.4 Hz, 1H); 7.14–7.35 (m, 2H); 7.46–7.54 (brm, 1H).

(3) A solution of 606 ml (85.4 mmol) of dimethyl sulfoxide in 50 ml of methylene chloride is cooled to −50° C. in a dry-ice/acetone bath. To the solution is added dropwise and gradually 3.73 ml (42.8 mmol) of oxalyl chloride and the mixture is stirred for 40 min while maintaining the temperature at −55° C. To the reaction mixture is added a 100 ml solution of 8.80 g (35.6 mmol) of compound 34 in methylene chloride over a period of more than 20 min and the stirring is continued for another 40 min at −55° C. Finally, 14.88 ml (107 mmol) of triethylamine is added gradually and, five minutes later, the dry-ice/acetone bath is removed. The reaction mixture is stirred for 45 min to warm up to room temperature and partitioned between ethyl acetate and 2N HCl. The organic layer is washed with water, a 5% $NaKCO_3$ solution, a saturated saline, dried, filtered and concentrated. The crude product, when purified by chromatography on silica gel and recrystallized from ethyl acetate/ hexane, gives 7.88 g (32.1 mmol; yield, 90%) of the objective compound (III-12).

M.p.=154°–156° C. $^1$HNMR ($CDCl_3$) δ: 1.53 (s, 9H); 6.55 (brs, 1H); 7.22–7.30 (m, 2H); 7.34 (dd, J=7.4, 0.5 Hz, 1H); 7.44 (dt, J=7.4, 2.1 Hz, 1H); 7.68–7.76 (brm, 1H); 9.41 (s,1H). IR (Nujol): 3320, 2930, 2180, 1728, 1658, 1590, 1551. Elementary analysis (%) for $C_{14}H_{15}NO_3 \cdot 0.3H_2O$. Calc. (%): C,67.08; H,6.27; N,5.59. Found (%): C, 67.21; H,6.19; N,5.50.

REFERENCE EXAMPLE 13

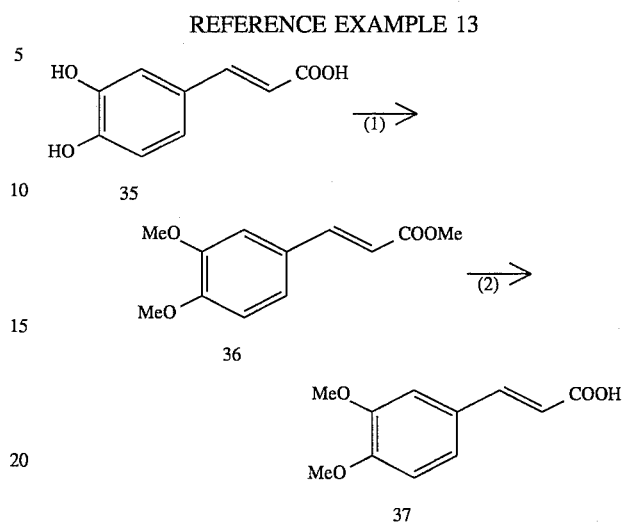

(1) To an 800 ml solution of 10.0 g (55.5 mmol) of starting material 35 in acetone are added 122.74 g (88.8 mmol) of potassium carbonate and 42.0 ml (444 mmol) of dimethyl sulfate and the mixture is heated to reflux for 2.5 hr. After cooling, potassium carbonate is removed by filtration and the filtrate is concentrated. The residue is partitioned between ethyl acetate and 2N HCl. The organic layer is washed with water and a saturated saline. The crude product, when purified by chromatography on silica gel and recrystallized from ethyl acetate/hexane, gives 10.06 g (45.3 mmol; yield, 82%) of the objective compound 36.

M.p.=68°–69° C. $^1$HNMR ($CDCl_3$) δ: 3.80 (s, 3H); 3.92 (s, 6H); 1.32 (d, J=15.9 Hz, 1H); 6.87 (d, J=8.2 Hz, 1H); 7.03–7.15 (m, 2H); 7.64 (d, J=15.9 Hz, 1H). IR (KBr): 2950, 2840, 1696, 1626, 1598, 1590, 1511. Elementary analysis (%) for $C_{12}H_{14}O_4$. Calc.(%): C,64.85; H,6.35. Found(%): C,64.66; H,6.41.

(2) Compound 36 is hydrolyzed in a manner analogous to that set forth in Example 7 (2) to obtain the objective compound 37 (yield, 96%).

M.p.=183° C. $^1$HNMR ($CDCl_3$) δ: 3.92 (s, 6H); 6.33 (d, J=15.9 Hz, 1H); 6.89 (d, J=8.2 Hz, 1H); 7.05–7.20 (m, 2H); 7.74 (d, J=15.9 Hz, 1H). IR (KBr): 3680–2000, 2930, 2830, 2560, 1680, 1625, 1598, 1582, 1513. Elementary analysis (%) for $C_{11}H_{12}O_4$. Calc.(%): C,63.45; H,5.81. Found(%): C,63.36; H,5.80.

The activity of the compounds prepared in the foregoing Examples was evaluated using the method described in the following experimental examples.

EXPERIMENT 1

Assay of Inhibition Against the Cell Growth of Vascular Endothelial Cells of Human Umbilical Vein Human vascular endothelial cells used had been obtained from human umbilical vein by perfusion method using an enzyme solution of collagenase and have been maintained by subculturing in a culture solution, i.e., M199 medium (Gibco, Inc.) supplemented with 20% fetal bovine serum (FBS; Gibco, Inc.), 100 μg/ml endothelial mitogen (Funakoshi), 90 μg/ml heparin, 50 IU/ml Penicillin and 50 μg/ml Streptomycin. A 100 μl suspension of 1×10⁴ human vascular endothelial cells in M199 medium containing 20% FBS was seeded in 96-well plate (Sumitomo Bakelite, MS-9096F) and cells were grown in a gas thermostat. On the next day, to each well was added 10 μl of a medium containing a sample at various concentrations. The sample was prepared by dissolving a test compound in dimethyl sulfoxide (DMSO) and diluting the solution with the medium so as to make the final concentration of DMSO less than 0.25%. After 3-day-incubation, to the mixture was added 50 μl of 3 mg/ml MTT solution (a solution of 3-(4,5-dimethyl-2-thiazolyl)-2,5-diphenyl-2 H-tetrazolium bromide dissolved in a culture solution) and the incubation was continued for 4 hr. Cells and MTT pigment were solubilized by the addition of 50 μl of 20% SDS solution (sodium dodecylsulfate dissolved in 0.02N HCl) and the incubation continued for 1 hr, which was followed by the determination of $OD_{570}$ value on spectrophotometer. Each sample was evaluated as to the inhibition activity against the cell growth of endothelial cells by assuming the OD value obtained in the control experiment, which was carried out in the same manner in the absence of a sample, to be 100%, calculating the concentration ($IC_{50}$) of each compound which gives 50% OD value of that obtained in control group and comparing the $IC_{50}$ values. The results are shown in Table 1 below.

TABLE 1

| Compound Number | MTT Method ($IC_{50}$ μM) |
| --- | --- |
| I-9 | 25.6 |
| I-10 | 20.4 |
| I-18 | 13.8 |
| I-19 | 26.7 |

EXPERIMENT 2

Assay of Inhibition Activity Against Cell Adhesion of Leukocytes onto Vascular Endothelial Cells of Human Umbilical Vein Human vascular endothelial cells used had been obtained from human umbilical vein by perfusion method using an enzyme solution of collagenase and have been maintained by subculturing in a culture solution, i.e., M199 medium (Gibco, Inc.) supplemented with 20% fetal bovine serum (FBS; Gibco, Inc.), 100 μg/ml endothelial mitogen (Funakoshi), 90 μg/ml heparin, 50 IU/ml Penicillin and 50 μg/ml Streptomycin. HL60 cells (human myelocytic leukemia cells) were purchased from Flow, Inc. and have been maintained by subculturing in RPMI1640 medium containing 10% FBS.

A 200 μl suspension of 1×10⁴ human vascular endothelial cells suspended in Dulbecco's Modified Essential Medium (DMEM) was seeded in 96-well plate (Sumitomo Bakelite, MS-9096F) and cells were grown in a gas thermostat. Four hours later, to each well was added 4 μl of a medium containing a sample at various concentrations. The sample was prepared by dissolving a test compound in DMSO and diluting the solution with a medium so as to make the final concentration of DMSO less than 0.25%. After 16-hour-incubation, 4 μl of 1×10⁴ μ/ml TNF solution (tumor necrosis factor dissolved in a medium solution) was added and the incubation was continued for 4 hr. The resultant medium solution containing the sample was then filtered with suction and washed (×3) with DMEM solution containing 10% FBS, which was followed by the addition of 200 μl suspension of 3×10⁵ HL-60 cells suspended in DMEM containing 10% FBS. The incubation was carried out at 37° C. for 30 min.

The supernatant was removed by aspiration, which was followed by washing (×2) with DMEM solution containing 10% FBS and the addition of 100 μl of 0.25% Rose Bengal solution (dissolved in phosphate-buffered physiological saline). After being allowed to stand for 5 min at room temperature, the supernatant was removed by aspiration, which was followed by washing (×2) with DMEM solution containing 10% FBS. A mixture of ethanol/phosphate-buffered physiological saline (1:1) was added and the resultant mixture was allowed to stand for 30 min to solubilize Rose Bengal pigment, which was followed by the determination of $OD_{570}$ value on spectrophotometer. The inhibition activity against the cell adhesion of leukocytes to endothelial cells was evaluated by assuming the OD value obtained in the control experiment, which was carried out in the same manner in the absence of a sample, to be 100%, calculating the concentration ($IC_{50}$) of each compound which gives 50% OD value of that obtained in control group and comparing the $IC_{50}$ values. The results are shown in Table 2 below.

TABLE 2

| Compound Number | $IC_{50}$ (μM) |
| --- | --- |
| I-7 | 4.5 |
| I-9 | 6.5 |
| I-10 | 5.3 |
| I-11 | 6.4 |
| I-17 | 8.3 |
| I-18 | 2.5 |
| I-19 | 6.3 |

Medium used: 9.5 g of Dulbecco's Eagle MEM medium (Nissui Seiyaku) solution, 20 ml of 7% sodium hydrogen carbonate solution are added to distilled water and a fetal bovine serum (Flow Laboratories, Inc.) was added to a final concentration of 10 v/v % to obtain the medium. The medium (100 μl) was added to a 96-well plate (Sumitomo Bakelite) and NIH3T3 cells transformed by ras gene (5×10³ cells/well) were seeded. The plate was incubated for 24 hr in a 5% carbon dioxide gas incubator. Then a sample to be tested was added in such a manner as to give 2-fold serial dilutions. After 24 hours, cells were observed morphologically to evaluate the detransformation activity. The results are shown in Table 3 below.

TABLE 3

Minimum Concentration Required for the Detransformation of Cells Transformed by Ras Gene

TABLE 3

Minimum Concentration Required for the Detransformation of Cells Transformed by Ras Gene

| Compound Number | MTC (μM) |
| --- | --- |
| I-4 | 1.6 |
| I-7 | 0.20 |
| I-9 | 3.2 |
| I-10 | 0.30 |
| I-11 | 0.60 |
| I-12 | 3.1 |
| I-17 | 3.2 |
| I-18 | 0.039 |
| I-19 | 0.30 |
| I-20 | 0.60 |

Industrial Utility

As can be seen from the above, the compounds of the present invention possess the inhibitory activities against the growth of vascular endothelial cells and the expression of lymphocyte adhesive factors and the detransforming activity of cells transformed by ras gene, and inhibit the cell growth and are effective on inflammation and tumor.

I claim:

1. A compound of the formula (Ia)

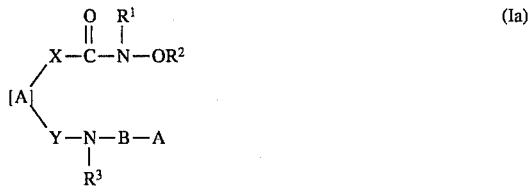

wherein

[A] represents a benzene ring, which is unsubstituted or substituted by one or more substituents selected from the group consisting of alkyl, hydroxy, alkoxy, aryloxy, carboxy, hydroxyamino, alkoxyamino, halogen, nitro, formyl, alkanoyl, aroyl, sulfonamide, halogenoalkyl, hydroxyalkyl, alkoxyalkyl, nitroalkyl and carboxyalkyl;

A represents phenyl, naphthyl, anthryl or phenanthryl, each of which is unsubstituted or substituted by one or more substituents selected from the group consisting of alkyl, hydroxy, alkoxy, aryloxy, carboxy, hydroxyamino, alkoxyamino, halogen, nitro, formyl, alkanoyl, aroyl, sulfonamide, halogenoalkyl, hydroxyalkyl, alkoxyalkyl, nitroalkyl and carboxyalkyl;

B represents a single bond or a bivalent group of the formula —$B_1$—$B_2$—, wherein $B_1$ represents —$SO_2$— and $B_2$ represents $C_1$–$C_8$ alkylene, $C_2$–$C_8$ alkenylene, $C_1$–$C_8$ alkyleneoxy or $C_2$–$C_8$ alkenyleneoxy; or —B—A represents (1) —$SO_2$— optionally substituted phenyl wherein the optional substituent is nitro, methyl, bromo, methoxy or fluoro, (2) —$SO_2$— naphthyl or (3) —CO-phenyl;

X represents $C_2$–$C_{10}$ alkylene which optionally contains an unsaturated bond(s);

Y represents a single bond;

$R^1$, $R^2$ and $R^3$ each independently represents (1) hydrogen, (2) $C_1$–$C_8$ alkyl which is unsubstituted or substituted by one or more substituents selected from the group consisting of alkyl, hydroxy, alkoxy, carboxy, hydroxyamino, alkoxyamino, halogen, nitro, formyl, alkanoyl, aroyl, sulfonamide, halogenoalkyl, hydroxyalkyl, alkoxyalkyl, nitroalkyl and carboxyalkyl, or (3) phenyl, naphthyl, anthryl or phenanthryl which is unsubstituted or substituted by one or more substituents selected from the group consisting of alkyl, hydroxy, alkoxy, aryloxy, carboxy, hydroxyamino, alkoxyamino, halogen, nitro, formyl, alkanoyl, aroyl, sulfonamide, halogenoalkyl, hydroxyalkyl, alkoxyalkyl, nitroalkyl and carboxyalkyl; or a pharmaceutically acceptable salt thereof.

2. An antitumor agent which contains the compound or salt as claimed in claim 1 together with a pharmaceutically acceptable carrier therefor.

3. An anti-inflammatory agent which contains the compound (I) as claimed in claim 1 together with a pharmaceutically acceptable carrier therefor.

* * * * *